US012747302B2

(12) United States Patent
Stupp et al.

(10) Patent No.: US 12,747,302 B2
(45) Date of Patent: Sep. 29, 2026

(54) AQUEOUS PEPTIDE PROGRAMMING OF THE VINYLIDENE FLUORIDE FERROELECTRIC PHASE

(71) Applicant: Northwestern University, Evanston, IL (US)

(72) Inventors: Samuel I. Stupp, Evanston, IL (US); Yang Yang, Evanston, IL (US)

(73) Assignee: Northwestern University, Evanston, IL (US)

(*) Notice: Subject to any disclaimer, the term of this patent is extended or adjusted under 35 U.S.C. 154(b) by 86 days.

(21) Appl. No.: 18/413,417

(22) Filed: Jan. 16, 2024

(65) Prior Publication Data

US 2025/0230263 A1 Jul. 17, 2025

Related U.S. Application Data

(60) Provisional application No. 63/480,083, filed on Jan. 16, 2023.

(51) Int. Cl.

| | |
|---|---|
| ***C07K 17/02*** | (2006.01) |
| ***B82Y 25/00*** | (2011.01) |
| ***C07K 5/103*** | (2006.01) |
| ***C07K 5/113*** | (2006.01) |

(52) U.S. Cl.

CPC .............. *C07K 17/02* (2013.01); *B82Y 25/00* (2013.01); *C07K 5/101* (2013.01); *C07K 5/1021* (2013.01)

(58) Field of Classification Search

CPC ...... C07K 17/02; C07K 5/1021; C07K 5/101; B82Y 25/00

See application file for complete search history.

(56) References Cited

PUBLICATIONS

Seidel et al, Shedding light on nanoscale ferroelectrics, Current Applied Physics, 2014, 14, pp. 1083-1091.*

Noisier et al, Late-Stage Functionalization of Histidine in Unprotected Peptides, Angew. Chem. Int. Ed., 2019, 58, pp. 19096-19102.*

Chen, X. et al. Relaxor ferroelectric polymer exhibits ultrahigh electromechanical coupling at low electric field. Science. Mar. 25, 2022;375(6587):1418-1422.

Collet E. et al. Laser-induced ferroelectric structural order in an organic charge-transfer crystal. Science. Apr. 25, 2003;300(5619):612-5.

Cui, H. et al. Amino acid sequence in constitutionally isomeric tetrapeptide amphiphiles dictates architecture of one-dimensional nanostructures. J Am Chem Soc. Sep. 3, 2014;136(35):12461-8.

Fu, D. et al. Diisopropylammonium bromide is a high-temperature molecular ferroelectric crystal. Science. Jan. 25, 2013;339(6118):425-8.

Fujiwara, K., et al. Dependence of α-helical and β-sheet amino acid propensities on the overall protein fold type. BMC Struct Biol. Aug. 2, 2012:12:18.

Furukawa, T. Ferroelectric properties of vinylidene fluoride copolymers. Phase Trans. 1989, 18, 143-211.

Garcia-Iglesias, M. et al. A Versatile Method for the Preparation of Ferroelectric Supramolecular Materials via Radical End-Functionalization of Vinylidene Fluoride Oligomers. J Am Chem Soc. May 18, 2016;138(19):6217-23.

Guo, M. et al. Toroidal polar topology in strained ferroelectric polymer. Science. Mar. 5, 2021;371(6533):1050-1056.

Horiuchi, S. et al. Ferroelectricity near room temperature in co-crystals of nonpolar organic molecules. Nat Mater. Feb. 2005;4(2):163-6.

Lovinger, A.J. Ferroelectric polymers. Science. Jun. 10, 1983;220(4602):1115-21.

Pan, H. et al. Ultrahigh energy storage in superparaelectric relaxor ferroelectrics. Science. Oct. 2021;374(6563):100-104.

Tayi, A.S. et al. Room-temperature ferroelectricity in supramolecular networks of charge-transfer complexes. Nature. Aug. 23, 2012;488(7412):485-9.

Yang, L. et al. Novel polymer ferroelectric behavior via crystal isomorphism and the nanoconfinement effect. Polymer vol. 54, Issue 7, Mar. 22, 2013, pp. 1709-1728.

Ye, H. et al. Metal-free three-dimensional perovskite ferroelectrics. Science. Jul. 13, 2018;361(6398):151-155.

Zhang, QM. et al. Giant electrostriction and relaxor ferroelectric behavior in electron-irradiated poly(vinylidene fluoride-trifluoroethylene) copolymer. Science. Jun. 26, 1998;280(5372):2101-4.

* cited by examiner

*Primary Examiner* — Li N Komatsu

(74) *Attorney, Agent, or Firm* — Casimir Jones, S.C.; Rikki A. Hullinger

(57) ABSTRACT

Provided herein are peptide amphiphiles comprising a β-sheet forming peptide sequence conjugated to two or more vinylidene fluoride (VDF) monomers, and nanoscale ferroelectric structures comprising the same.

20 Claims, 46 Drawing Sheets

Specification includes a Sequence Listing.

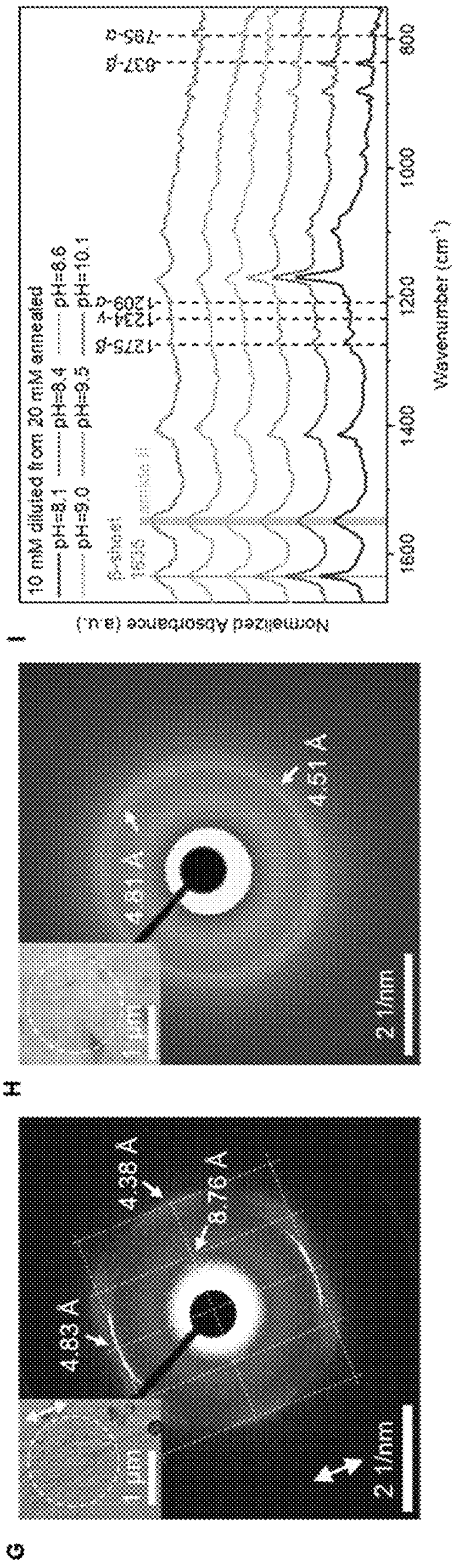
FIGS. 2G-I

AQUEOUS PEPTIDE PROGRAMMING OF THE VINYLIDENE FLUORIDE FERROELECTRIC PHASE

PRIORITY STATEMENT

This application claims priority to U.S. Provisional Application No. 63/480,083, filed Jan. 16, 2023, the entire contents of which are incorporated herein by reference for all purposes.

STATEMENT REGARDING FEDERAL FUNDING

This invention was made with government support under grant number DE-SC0020884 awarded by the Department of Energy. The government has certain rights in the invention.

SEQUENCE LISTING

The text of the computer readable sequence listing filed herewith, titled "41626-202_SQL", created Jan. 16, 2024, having a file size of 8,812 bytes, is hereby incorporated by reference in its entirety.

BACKGROUND

Poly(vinylidene fluoride) (PVDF) is the leading organic ferroelectric material and has generated great interest due to its applications in electronics and electromechanical devices. To obtain the electroactive polymorph requires mechanical drawing of the polymer at low temperatures or random copolymerization with additional monomers. Drawing and chemical disorder induced by copolymerization make it difficult to precisely control nanoscale ferroelectric structure and consequent properties. Accordingly, what is needed are approaches to form functional ferromagnetic structures at the nanoscale.

SUMMARY

The ability to precisely control ferroelectric domains in polymers on the nanoscale would enable novel ferroelectrics and relaxor ferroelectrics with potential applications for memory, sensing, electromechanical and electrocaloric energy conversion, among others. Described herein is the use of peptides to direct the supramolecular assembly of oligomeric vinylidene fluoride (VDF) into ferroelectric and relaxor ferroelectric structures, which have never been reported by existing approaches on VDF-based polymers. The intrinsic matching of the lattice constants of crystalline VDF and the β-sheet hydrogen bonding of the peptide region results in a thermodynamically stable ferroelectric VDF phase with the Curie transition temperature of 110° C., higher than the commonly used VDF-based ferroelectric copolymers. Using a peptide sequence with weaker hydrogen bonding leads to highly twisted and loosely packed assemblies with weaker ferroelectricity but higher electromechanical energy conversion. This work offers a versatile approach to tune the nanoscale structure and functionalities of organic ferroelectrics at room temperature for specific applications using simple chemical modifications in water.

In some aspects, provided herein are peptide amphiphiles comprising a β-sheet forming peptide sequence conjugated to two or more vinylidene fluoride (VDF) monomers. In some embodiments, the β-sheet forming peptide sequence has a total propensity for forming β-sheets of at least 5. In some embodiments, the β-sheet forming peptide sequence is 4-10 amino acid residues in length. In some embodiments, each of the 4-10 amino acid residues is independently selected from valine (V), glutamic acid (E), and aspartic acid (D). In some embodiments, at least 50% of the amino acid residues are valine residues. In some embodiments, the β-sheet forming peptide sequence comprises 4 amino acids and has a total propensity for forming β-sheets of at least 5. In some embodiments, the β-sheet forming peptide sequence comprises VVEE (SEQ ID NO: 1), VEVE (SEQ ID NO: 2), or EVEV (SEQ ID NO: 3).

In some embodiments, the β-sheet forming peptide sequence is conjugated to 3 to 10 VDF monomers. For example, in some embodiments the β-sheet forming peptide sequence is conjugated to three VDF monomers (VDF3), four VDF monomers (VDF4), five VDF monomers (VDF5), or six VDF monomers (VDF6). In some embodiments, the peptide amphiphile comprises VDF6-EVEV (SEQ ID NO: 3), VDF6-VEVE (SEQ ID NO: 2), or VDF6-VVEE (SEQ ID NO: 1).

In some aspects, provided herein are nanoscale ferroelectric structures comprising a plurality of self-assembled peptide amphiphiles described herein. In some embodiments, provided herein is a nanoscale ferroelectric structure comprising a plurality of self-assembled peptide amphiphiles, wherein each peptide amphiphile comprises a β-sheet forming peptide sequence conjugated to two or more vinylidene fluoride (VDF) monomers. In some embodiments, the β-sheet forming peptide sequence of each peptide amphiphile has a total propensity for forming β-sheets of at least 5. In some embodiments, the β-sheet forming peptide sequence of each peptide amphiphile is 4-10 amino acid residues in length. In some embodiments, each of the 4-10 amino acid residues is independently selected from valine (V), glutamic acid (E), and aspartic acid (D). In some embodiments, at least 50% of the amino acid residues are valine residues. In some embodiments, the β-sheet forming peptide sequence of each peptide amphiphile comprises 4 amino acids and has a total propensity for forming β-sheets of at least 5. In some embodiments, the β-sheet forming peptide sequence of each peptide amphiphile comprises VVEE (SEQ ID NO: 1), VEVE (SEQ ID NO: 2), or EVEV (SEQ ID NO: 3).

In some embodiments, the β-sheet forming peptide sequence of each peptide amphiphile is conjugated to 3 to 10 VDF monomers. In some embodiments, the β-sheet forming peptide sequence of each peptide amphiphile is conjugated to three VDF monomers (VDF3), four VDF monomers (VDF4), five VDF monomers (VDF5), or six VDF monomers (VDF6). In some embodiments, each peptide amphiphile is independently selected from VDF6-EVEV (SEQ ID NO: 3), VDF6-VEVE (SEQ ID NO: 2), or VDF6-VVEE (SEQ ID NO: 1).

BRIEF DESCRIPTION OF THE DRAWINGS

(FIG. 1A) Molecular structures of the VDF-PAs containing hydrophobic tails with three to six VDF repeat units and peptide sequences of VVEE (SEQ ID NO: 1), VEVE (SEQ ID NO: 2) and EVEV (SEQ ID NO: 3). (FIGS. 1B-1D) Liquid AFM images of (FIG. 1B) VDF6-VVEE (SEQ ID NO: 1), (FIG. 1C) VDF6-VEVE (SEQ ID NO: 2) and (FIG. 1D) VDF6-EVEV (SEQ ID NO: 3) cast from 20 mM aqueous solutions after annealing. Corresponding height profiles were measured along the arrows. (FIGS. 1E-G) Schematic illustration of the supramolecular architectures of (FIG. 1E) VDF6-VVEE (SEQ ID NO: 1), (FIG. 1F) VDF6-VEVE (SEQ ID NO: 2) and (FIG. 1G) VDF6-EVEV (SEQ ID NO: 3) assemblies.

FIGS. 2A-2I show crystal structures of the VDF-PA assemblies. (FIGS. 2A-C) ATR-FTIR spectra of (FIG. 2A) VVEE (SEQ ID NO: 1), (FIG. 2B) VEVE (SEQ ID NO: 2) and (FIG. 2C) EVEV (SEQ ID NO: 3) PA assemblies dried from 10 mM annealed solution with the indexing of amide I in β-sheet peptides and α, β, and γ phase VDF. (FIG. 2D) X-ray scattering patterns of VDF6-VVEE (SEQ ID NO: 1), VDF6-VEVE (SEQ ID NO: 2) and VDF6-EVEV (SEQ ID NO: 3) assemblies in solutions in MAXS and WAXS regions. Reflections of inter-β-sheet and hydrogen bonding (H-bonding) spacings are indexed by dashed black lines and scattering of α- and β-phase VDF are labeled by purple lines. (FIGS. 2E-H) Selected-area electron diffraction (SAED) of the VDF6-PA assemblies. (FIG. 2E) Azimuthally integrated SAED patterns of dry state (FIG. 2F) VDF6-VVEE (SEQ ID NO: 1), (FIG. 2G) VDF6-VEVE (SEQ ID NO: 2) and (FIG. 2H) VDF6-EVEV (SEQ ID NO: 3) assemblies with indexing of hydrogen bonding in β-sheets and α, β phase VDF. (FIG. 2I) ATR-FTIR spectra of VDF6-VEVE (SEQ ID NO: 2) liquid samples during pH titration. The intensities in (FIGS. 2A-E and FIG. 2I) were offset vertically for clarity. Insets in (FIGS. 2F-H) show the corresponding electron micrograph of the partially aligned supramolecular assemblies and the dashed white circles denote the selected areas' aperture.

(FIGS. 3A-C) DSC thermograms of the annealed (FIG. 3A) VDF6-VVEE (SEQ ID NO: 1), (FIG. 3B) VDF6-VEVE (SEQ ID NO: 2) and (FIG. 3C) VDF6-EVEV (SEQ ID NO: 3) in the first cooling cycle. The heat capacity curves were offset vertically for clarity. (FIGS. 3D-F) VT-WAXS patterns of 20 mM annealed (FIG. 3D) VDF6-VVEE (SEQ ID NO: 1), (FIG. 3E) VDF6-VEVE (SEQ ID NO: 2) and (FIG. 3F) VDF6-EVEV (SEQ ID NO: 3) with the peak positions indicated: 020 plane at q=1.30 $Å^{-1}$ and 110/200 plane at q=1.43 $Å^{-1}$ for α-phase VDF, 110/200 plane at q=1.46 $Å^{-1}$ for β-phase VDF, q=1.34 $Å^{-1}$ for hydrogen bond spacing of β-sheet peptide and its second order reflection at q=2.59 $Å^{-1}$. The scattering intensities were offset vertically for clarity. (FIG. 3G, FIG. 3F, FIG. 3I) The scattering intensity obtained from Gaussian fitting of the scattering patterns in (FIGS. 3D-F) show the crystallinity of as a function of temperature.

(FIGS. 4A-C) Polarization-electric field (P-E) loops of (FIG. 4A) VDF6-VVEE (SEQ ID NO: 1), (FIG. 4B) VDF6-VEVE (SEQ ID NO: 2) and (FIG. 4C) VDF6-EVEV (SEQ ID NO: 3) dry-state coatings. (FIG. 4D) Summary of coercive field and the ratio $P_r/P_s$ of the VDF6 PA samples under different applied maximum voltages. (FIGS. 4E-G) The variable-temperature dielectric constant of (FIG. 4E) VDF6-VVEE (SEQ ID NO: 1), (FIG. 4F) VDF6-VEVE (SEQ ID NO: 2) and (FIG. 4G) VDF6-EVEV (SEQ ID NO: 3) PA thin films under different frequencies. The gray arrows show the dependence of the dielectric constant peak on the frequency of the applied electric field upon heating. The inset in (FIG. 4G) shows the fitting of the measured dielectric constant peaks with the Vogel-Folcher law. (FIG. 4H) Illustration of PFM butterfly loop measurement on the PA samples prepared on porous anodic aluminum oxide film with a conductive substrate. (FIG. 4I) PFM amplitude and phase hysteresis loops of the VDF6-PA samples.

(FIG. 5A) VDF3-VVEE (SEQ ID NO: 1), (FIG. 5B) VDF3-VEVE (SEQ ID NO: 2), (FIG. 5C) VDF3-EVEV (SEQ ID NO: 3), (FIG. 5D) VDF4-VVEE (SEQ ID NO: 1), (FIG. 5E) VDF4-VEVE (SEQ ID NO: 2), (FIG. 5F) VDF4-EVEV (SEQ ID NO: 3), (FIG. 5G) VDF5-VVEE (SEQ ID NO: 1), (FIG. 5H) VDF5-VEVE (SEQ ID NO: 2), (FIG. 5I) VDF5-EVEV (SEQ ID NO: 3), (FIG. 5J) VDF6-VVEE (SEQ ID NO: 1), (FIG. 5K) VDF6-VEVE (SEQ ID NO: 2) and (FIG. 5L) VDF6-EVEV (SEQ ID NO: 3).

(FIG. 6A) VDF4-VVEE (SEQ ID NO: 1), (FIG. 6B) VDF4-VEVE (SEQ ID NO: 2), (FIG. 6C) VDF4-EVEV (SEQ ID NO: 3), (FIG. 6D) VDF5-VVEE (SEQ ID NO: 1), (FIG. 6E) VDF5-VEVE (SEQ ID NO: 2), (FIG. 6F) VDF5-EVEV (SEQ ID NO: 3), (FIG. 6G) VDF6-VVEE (SEQ ID NO: 1), (FIG. 6H) VDF6-VEVE (SEQ ID NO: 2), (FIG. 6I) VDF6-EVEV (SEQ ID NO: 3).

(FIG. 7A) VDF6-VVEE (SEQ ID NO: 1), (FIG. 7B) VDF6-VEVE (SEQ ID NO: 2), (FIG. 7C) VDF6-EVEV (SEQ ID NO: 3).

(FIG. 8A) VDF4-VVEE (SEQ ID NO: 1), (FIG. 8B) VDF4-VEVE (SEQ ID NO: 2), (FIG. 8C) VDF4-EVEV (SEQ ID NO: 3), (FIG. 8D) VDF5-VVEE (SEQ ID NO: 1), (FIG. 8E) VDF5-VEVE (SEQ ID NO: 2) and (FIG. 8F) VDF5-EVEV (SEQ ID NO: 3). No height measurement was performed on VDF4-EVEV because nearly no fibers but aggregations of micelles left after the washing during sample preparation. The baselines of the measured height curves were shifted to 0 nm for comparison.

(FIG. 15A-15C) AFM images of the aligned (FIG. 15A) VDF6-VVEE (SEQ ID NO: 1), (FIG. 15B) VDF6-VEVE (SEQ ID NO: 2) and (FIG. 15C) VDF6-EVEV (SEQ ID NO: 3) fibers prepared by solution embossing on a Germanium wafer. (FIG. 15D-15F) Non-polarized and polarized transmission FTIR spectrum on the aligned (FIG. 15D) VDF6-VVEE (SEQ ID NO: 1), (FIG. 15E) VDF6-VEVE (SEQ ID NO: 2) and (FIG. 15F) VDF6-EVEV (SEQ ID NO: 3) fibers with the electric field of the incident IR is parallel (p-polarized as indicated by the vertical arrow in (FIG. 15A)) or perpendicular (s-polarized as indicated by the horizontal arrow in (FIG. 15A)) to the elongation axis of the PA assemblies. The absorbance intensities of the spectrum were normalized to the characteristic band of isotropic bending of $CH_3$ group $\delta(CH_3)$ at 1261 $cm^{-1}$. The absorption band of amide C═O stretching vibration ν(C═O) near 1635 $cm^{-1}$, with the transition dipole moment parallel to hydrogen bond, and $CF_2$ rocking $r(CF_2)$ at 837 $cm^{-1}$, with the dipole transition moment perpendicular to the polar b axis of β-phase VDF, were indexed.

(FIG. 20A) A picture and schematic of the testing chip showing the dimensions of the photolithographically patterned platinum electrodes on the $SiO_2$ insulating layer. (FIG. 20B) Frequency domain capacitance of the gap under different amplitudes of AC voltage. (FIG. 20C) Capacitance of the gap under different frequencies as a function of voltage amplitude. (FIG. 20D) Leakage current of the gap as a function of time under different DC voltages. (FIG. 20E) Resistance of the gap according to the leakage current under different voltage.

(FIG. 28C) Summary of coercive field and the ratio $P_r/P_s$ of the VDF-VEVE PA samples under different applied maximum voltages.

(FIG. 29A) Frequency domain capacitance under different amplitudes of AC voltage. (FIG. 29B) Capacitance of the VDF6-COOH sample under different frequencies as a function of voltage amplitude. (FIG. 29C) Leakage current of the VDF6-COOH as a function of time under different DC voltages. (FIG. 29D) Resistance of the gap according to the leakage current measured under different voltage. (FIG. 29E) P-E loops of the VDF-COOH sample under different applied maximum voltages.

(FIG. 32C) Summary of coercive field and the ratio $P_r/P_s$ of the VDF-VVEE PA samples under different applied maximum voltages. P-E loops of (FIG. 32D) VDF4-EVEV (SEQ ID NO: 3) and (FIG. 32E) VDF5-EVEV (SEQ ID NO: 3) under different applied maximum voltages. (FIG. 32F) Summary of coercive field and the ratio $P_r/P_s$ of the VDF-EVEV PA samples under different applied maximum voltages. For the cigar-shaped lossy loops, the measured coercive field and remanent polarization are also contributed by conduction loss.

(FIG. 33A) Solution casting on the gold-plated silicon wafer clinging to a waterproof acrylic tape (3M, 300 LSE) with punctured round holes of 4 mm diameter to hold the liquid before evaporation. (FIG. 33B) Sample cell with Ar intake, micro thermocouple and the sample fixed nearby on the heating bottom and a spring probe as the top electrode.

(FIG. 38A) AFM morphologies of the AAO substrate filled with annealed VDF6-VEVE (SEQ ID NO: 2) assemblies in dry state. (FIG. 38B, FIG. 38C, FIG. 38D) PFM phase and amplitude of VDF6-VEVE (SEQ ID NO: 2) assemblies at point a, b, c and the AAO wall at point a', b', c'. (FIG. 38E) PFM phase and amplitude of VDF6-VEVE (SEQ ID NO: 2) assemblies at point d under different amplitude of driving voltages showing constant switching voltage.

(FIG. 39A) AFM morphologies of the AAO substrate filled with annealed VDF6-VVEE (SEQ ID NO: 1) assemblies in dry state. (FIG. 39B, FIG. 39C, FIG. 39E) PFM phase and amplitude of VDF6-VVEE (SEQ ID NO: 1) assemblies at point a, b, c, d and the AAO wall at point a', b', c', d'.

(FIG. 40A) AFM morphologies of the AAO substrate filled with annealed VDF6-EVEV (SEQ ID NO: 3) assemblies in dry state. (FIG. 40B, FIG. 40C, FIG. 40E) PFM phase and amplitude of VDF6-EVEV (SEQ ID NO: 3) assemblies at point a, b, c, d and the AAO wall at point c', d'.

(FIG. 41A) AFM morphologies of the AAO substrate filled with annealed VDF6-EVEV assemblies in dry state. PFM phase and amplitude at the point on AAO wall as labeled by "+" in (A) using (FIG. 41B) different contact forces and (FIG. 41C) sweeping frequencies of tip bias.

DEFINITIONS

Figures 1A, 1B, 1C, 1D:
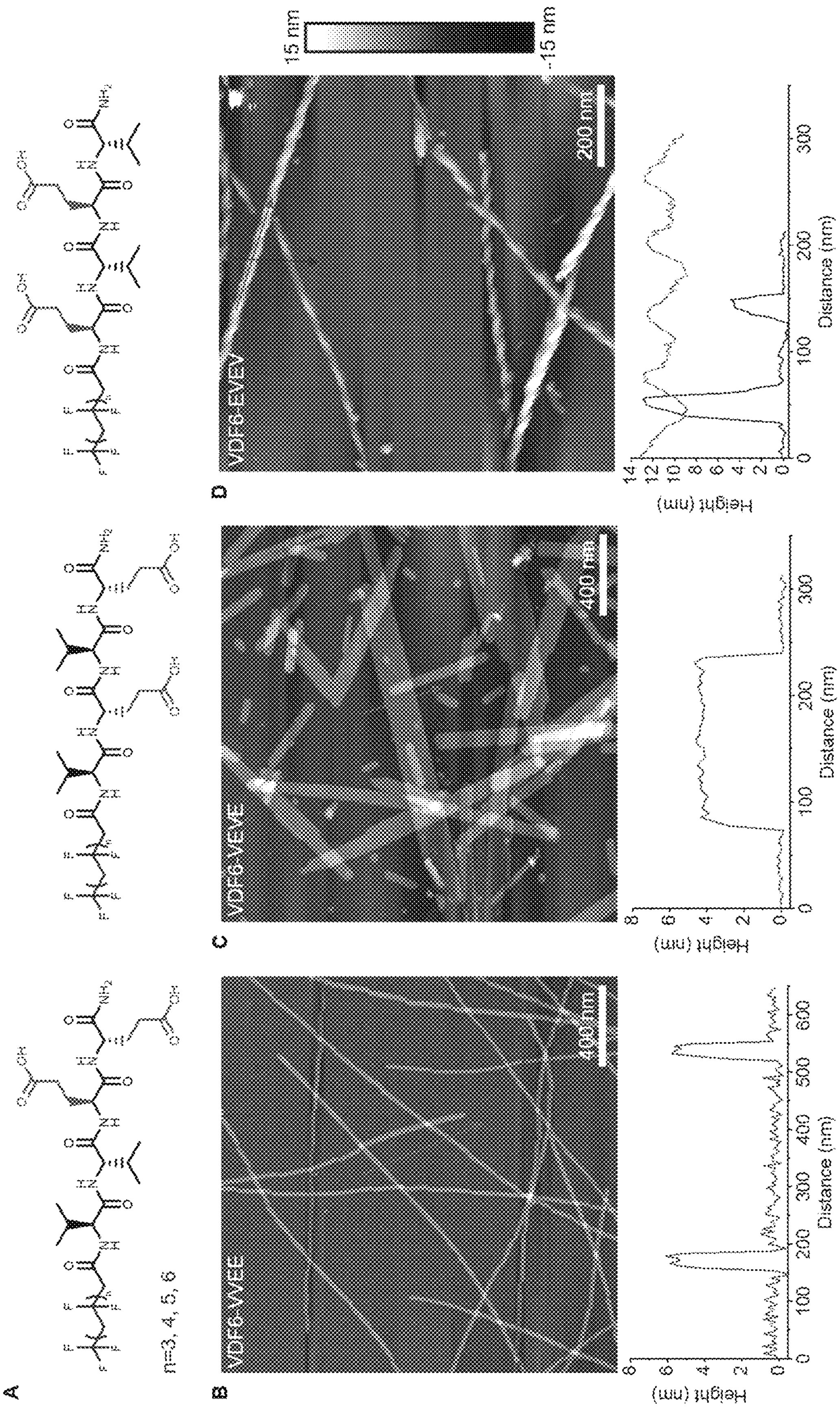
FIGS. 1A-1G show molecular structures, morphologies, and supramolecular architectures of the VDF-PA assemblies.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

The term "amino acid" refers to natural amino acids, unnatural amino acids, and amino acid analogs, all in their D and L stereoisomers, unless otherwise indicated, if their structures allow such stereoisomeric forms.

Natural amino acids include alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), Lysine (Lys or K), methionine (Met or M), phenylalanine (Phe or F), proline (Pro or P), serine (Ser or S), threonine (Thr or T), tryptophan (Trp or W), tyrosine (Tyr or Y) and valine (Val or V).

Unnatural amino acids include, but are not limited to, azetidinecarboxylic acid, 2-aminoadipic acid, 3-aminoadipic acid, beta-alanine, naphthylalanine ("naph"), aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine ("(BuG"), 2,4-diaminoisobutyric acid, desmosine, 2,2'-diaminopimelic acid, 2,3-diaminopropionic acid, N-ethylglycine, N-ethylasparagine, homoproline ("hPro" or "homoP"), hydroxylysine, allo-hydroxylysine, 3-hydroxyproline ("3Hyp"), 4-hydroxyproline ("4Hyp"), isodesmosine, allo-isoleucine, N-methylalanine ("MeAla" or "Nime"), N-alkylglycine ("NAG") including N-methylglycine, N-methylisoleucine, N-alkylpentylglycine ("NAPG") including N-methylpentylglycine. N-methylvaline, naphthylalanine, norvaline ("Norval"), norleucine ("Norleu"), octylglycine ("OctG"), ornithine ("Orn"), pentylglycine ("pG" or "PGly"), pipecolic acid, thioproline ("ThioP" or "tPro"), homoLysine ("hLys"), and homoArginine ("hArg").

The term "amino acid analog" refers to a natural or unnatural amino acid where one or more of the C-terminal carboxy group, the N-terminal amino group and side-chain bioactive group has been chemically blocked, reversibly or irreversibly, or otherwise modified to another bioactive group. For example, aspartic acid-(beta-methyl ester) is an amino acid analog of aspartic acid; N-ethylglycine is an amino acid analog of glycine; or alanine carboxamide is an amino acid analog of alanine. Other amino acid analogs include methionine sulfoxide, methionine sulfone, S-(carboxymethyl)-cysteine, S-(carboxymethyl)-cysteine sulfoxide and S-(carboxymethyl)-cysteine sulfone.

As used herein, the term "peptide" refers an oligomer to short polymer of amino acids linked together by peptide bonds. In contrast to other amino acid polymers (e.g., proteins, polypeptides, etc.), peptides are of about 50 amino acids or less in length. A peptide may comprise natural amino acids, non-natural amino acids, amino acid analogs, and/or modified amino acids. A peptide may be a subsequence of naturally occurring protein or a non-natural (artificial) sequence.

As used herein, the term "artificial" refers to compositions and systems that are designed or prepared by man, and are not naturally occurring. For example, an artificial peptide, peptoid, or nucleic acid is one comprising a non-natural sequence (e.g., a peptide without 100% identity with a naturally-occurring protein or a fragment thereof).

As used herein, a "conservative" amino acid substitution refers to the substitution of an amino acid in a peptide or polypeptide with another amino acid having similar chemical properties, such as size or charge. For purposes of the present disclosure, each of the following eight groups contains amino acids that are conservative substitutions for one another:

1) Alanine (A) and Glycine (G);
2) Aspartic acid (D) and Glutamic acid (E);
3) Asparagine (N) and Glutamine (Q);
4) Arginine (R) and Lysine (K);
5) Isoleucine (I), Leucine (L), Methionine (M), and Valine (V);
6) Phenylalanine (F), Tyrosine (Y), and Tryptophan (W);
7) Serine(S) and Threonine (T); and
8) Cysteine (C) and Methionine (M).

Naturally occurring residues may be divided into classes based on common side chain properties, for example: polar positive (or basic) (histidine (H), lysine (K), and arginine (R)); polar negative (or acidic) (aspartic acid (D), glutamic acid (E)); polar neutral (serine(S), threonine (T), asparagine (N), glutamine (Q)); non-polar aliphatic (alanine (A), valine (V), leucine (L), isoleucine (I), methionine (M)); non-polar aromatic (phenylalanine (F), tyrosine (Y), tryptophan (W)); proline and glycine; and cysteine. As used herein, a "semi-conservative" amino acid substitution refers to the substitution of an amino acid in a peptide or polypeptide with another amino acid within the same class.

In some embodiments, unless otherwise specified, a conservative or semi-conservative amino acid substitution may also encompass non-naturally occurring amino acid residues that have similar chemical properties to the natural residue. These non-natural residues are typically incorporated by chemical peptide synthesis rather than by synthesis in biological systems. These include, but are not limited to, peptidomimetics and other reversed or inverted forms of amino acid moieties. Embodiments herein may, in some embodiments, be limited to natural amino acids, non-natural amino acids, and/or amino acid analogs.

Non-conservative substitutions may involve the exchange of a member of one class for a member from another class.

As used herein, the term "sequence identity" refers to the degree of which two polymer sequences (e.g., peptide, polypeptide, nucleic acid, etc.) have the same sequential composition of monomer subunits. The term "sequence similarity" refers to the degree with which two polymer sequences (e.g., peptide, polypeptide, nucleic acid, etc.) differ only by conservative and/or semi-conservative amino acid substitutions. The "percent sequence identity" (or "percent sequence similarity") is calculated by: (1) comparing two optimally aligned sequences over a window of comparison (e.g., the length of the longer sequence, the length of the shorter sequence, a specified window, etc.), (2) determining the number of positions containing identical (or similar) monomers (e.g., same amino acids occurs in both sequences, similar amino acid occurs in both sequences) to yield the number of matched positions, (3) dividing the number of matched positions by the total number of positions in the comparison window (e.g., the length of the longer sequence, the length of the shorter sequence, a specified window), and (4) multiplying the result by 100 to yield the percent sequence identity or percent sequence similarity. For example, if peptides A and B are both 20 amino acids in length and have identical amino acids at all but 1 position, then peptide A and peptide B have 95% sequence identity. If the amino acids at the non-identical position shared the same biophysical characteristics (e.g., both were acidic), then peptide A and peptide B would have 100% sequence similarity. As another example, if peptide C is 20 amino acids in length and peptide D is 15 amino acids in length, and 14 out of 15 amino acids in peptide D are identical to those of a portion of peptide C, then peptides C and D have 70% sequence identity, but peptide D has 93.3% sequence identity to an optimal comparison window of peptide C. For the purpose of calculating "percent sequence identity" (or "percent sequence similarity") herein, any gaps in aligned sequences are treated as mismatches at that position.

Any polypeptides described herein as having a particular percent sequence identity or similarity (e.g., at least 70%) with a reference sequence ID number, may also be expressed as having a maximum number of substitutions (or terminal deletions) with respect to that reference sequence. For example, a sequence having at least Y % sequence identity (e.g., 90%) with SEQ ID NO: Z (e.g., 100 amino acids) may have up to X substitutions (e.g., 10) relative to SEQ ID NO: Z, and may therefore also be expressed as "having X (e.g., 10) or fewer substitutions relative to SEQ ID NO:Z."

As used herein, the term "supramolecular" (e.g., "supramolecular complex," "supramolecular interactions," "supramolecular fiber," "supramolecular polymer," etc.) refers to the non-covalent interactions between molecules (e.g., polymers, macromolecules, etc.) and the multicomponent assemblies, complexes, systems, and/or fibers that form as a result.

As used herein, the terms "self-assemble" and "self-assembly" refer to formation of a discrete, non-random, aggregate structure from component parts; said assembly occurring spontaneously through random movements of the components (e.g. molecules) due only to the inherent chemical or structural properties and attractive forces of those components.

DETAILED DESCRIPTION

The structure of ferroelectric materials creates a spontaneous macroscopic polarization that can be externally inverted with an applied electric field. Organic ferroelectrics have desirable qualities including lightness, mechanical flexibility, minimal toxicity, and also the potential ability to interface with biological systems or integrate into soft electronics. Previously investigated organic ferroelectrics are based on small molecules include co-crystals where hydrogen bonding (*Nat. Mater.* 4, 163-166 (2005)) and charge transfer (*Science.* 300, 612-615 (2003), *Nature.* 488, 485-489 (2012)) help create the requisite non-centrosymmetric structures for spontaneous polarization.

The ferroelectricity in crystalline poly(vinylidene fluoride) (PVDF) arises from the all-trans conformation of the backbone containing strong $CF_2$ dipoles on every other carbon atom, known as the "β-phase" (*Science.* 220, 1115-1121 (1983)). This β-phase of the crystalline polymer is unique among organic ferroelectrics in that it generates multiaxial ferroelectricity in the cross-section of the backbone (*Science.* 371, 1050-1056 (2021)), which is useful for thin-film applications but is difficult to achieve in small molecule ferroelectrics (*Science.* 339, 425-428 (2013), *Science.* 361, 151-155 (2018)).

A major limitation of PVDF is the that the β-phase is not thermodynamically stable relative to non-polar crystal structures. As a result the β-phase is created in this ferroelectric material only by mechanical stretching or random copolymerization with trifluoroethylene. Given the emerging opportunities in organic ferroelectrics, an important scientific goal is to develop new approaches to create multiaxial forms of these functional structures at the nanoscale. There have been studies grafting VDF to synthetic aromatic cores (*J. Am. Chem. Soc.* 138, 6217-6223 (2016)), but programming of a thermodynamically stable ferroelectric phase has not been reported.

Described herein is the use of vinylidene fluoride oligomers conjugated to peptides to create self-assembled filaments in water that yield nanoscale ferroelectric structures. In these systems the β-sheet secondary structure commonly found in proteins programs pure VDF oligomers to select the highly coveted conformation present in the ferroelectric polymorph of PVDF. Variations in the peptide were found to yield "relaxor" phases in which small ferroelectric domains generate strong electromechanical actuation. This biomolecular approach can generate sustainable, water-processable ferroelectric structures for sensing, memory, and energy transduction.

In some aspects, provided herein are peptide amphiphiles comprising a β-sheet forming peptide sequence conjugated to two or more vinylidene fluoride (VDF) monomers. Vinylidene fluoride has the molecular formula $C_2H_2F_2$ and is also referred to as 1,1-Difluoroethylene. Poly(vinylidene) fluoride, or PVDF, is produced by the polymerization of vinylidene difluoride and has the chemical formula $(C_2H_2F_2)_n$. The structure of polyvinylidene fluoride is:

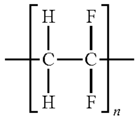

The β-sheet forming peptide sequence refers to a peptide segment that has a propensity to display β-sheet-like character (e.g., when analyzed by CD). In some embodiments, amino acids in a beta (β)-sheet-forming peptide sequence are selected for their propensity to form a beta-sheet secondary structure. Examples of suitable amino acid residues selected from the twenty naturally occurring amino acids include Met (M), Val (V), Ile (I), Cys (C), Tyr (Y), Phe (F), Gln (Q), Leu (L), Thr (T), Ala (A), and Gly (G) (listed in order of their propensity to form beta sheets). However, non-naturally occurring amino acids of similar beta-sheet forming propensity may also be used.

In some embodiments, the β-sheet forming peptide sequence has a total propensity for forming β-sheets of at least 4.5. In some embodiments, the β-sheet forming peptide sequence has a total propensity for forming β-sheets of at least 5. In some embodiments, the β-sheet forming peptide sequence has a total propensity for forming β-sheets of at least 5.3. The total propensity for forming β-sheet conformations may be calculated as the sum of the propensity for forming β-sheet conformations of each amino acid in the peptide sequence. The propensity of each amino acid for forming β-sheet conformations and methods for calculating the same are described in, for example, Fujiwara, K., Toda, H. & Ikeguchi, M. Dependence of α-helical and β-sheet amino acid propensities on the overall protein fold type. *BMC Struct Biol* 12, 18 (2012), the entire contents of which are incorporated herein by reference. Exemplary values are shown in Table 1, below. For the purposes of calculating the total propensity for forming β-sheet conformations of a peptide sequence, the value shown in the "total residues" column from table 1 for each amino acid is added together. For example, for a VVEE (SEQ ID NO: 1) peptide sequence, the total propensity for forming β-sheet conformations is 2+2+0.65+0.65=5.3.

TABLE 1

Amino acid Propensities for β-sheet conformations

| Amino Acid | Exposed Residues | Buried Residues | Total Residues |
|---|---|---|---|
| V | 2.31 | 1.57 | 2.00 |
| I | 2.02 | 1.39 | 1.79 |
| L | 1.18 | 0.93 | 1.15 |
| M | 1.01 | 0.84 | 1.01 |
| P | 0.49 | 0.42 | 0.40 |
| A | 0.48 | 0.72 | 0.75 |
| C | 1.24 | 1.07 | 1.36 |
| F | 1.50 | 1.10 | 1.4 |
| Y | 1.71 | 1.12 | 1.37 |
| W | 1.90 | 0.91 | 1.23 |
| Q | 0.96 | 0.82 | 0.72 |
| S | 0.86 | 0.85 | .081 |
| T | 1.58 | 1.08 | 1.21 |
| N | 0.71 | 0.76 | 0.63 |
| H | 1.15 | 0.98 | 0.99 |
| D | 0.61 | 0.76 | 0.55 |
| K | 1.14 | 0.98 | 0.76 |
| E | 0.89 | 0.86 | 0.65 |
| R | 1.27 | 0.82 | 0.85 |
| G | 0/41 | 0.81 | 0.67 |

In some embodiments, the total propensity for forming β-sheet conformations increases as the length of the β-sheet forming peptide sequence increases. For example, in some embodiments the β-sheet forming peptide sequence is exactly 4 amino acids in length and has a total propensity for forming β-sheet configurations of at least 4.5, at least 5, or at least 5.3. In some embodiments, the β-sheet forming peptide sequence is more than 4 amino acids in length and has a total propensity for forming β-sheet configurations of 5.5 or greater. For example, it can be envisioned that addition of an extra valine residue (V) to a sequence would increase the total propensity for forming β-sheet configurations of the β-sheet forming peptide sequence by 2.

In some embodiments, the β-sheet forming peptide sequence comprises 4-10 amino acids. In some embodiments, the β-sheet forming peptide sequence comprises 4-10 amino acids and has a total propensity for forming β-sheet configurations of at least 5, at least 6, at least 7, at least 8, at least 9, at least 10, at least 11, or at least 12.

In some embodiments, the β-sheet forming peptide sequence is at least 4 and no more than 10 amino acids in length. For example, in some embodiments the β-sheet forming peptide sequence is 4 amino acids, 5 amino acids, 6 amino acids, 7 amino acids, 8 amino acids, 9 amino acids, or 10 amino acids in length. In some embodiments, the β-sheet forming peptide sequence is exactly 4 amino acids in length and has a total propensity for forming β-sheet configurations of at least 5. In some embodiments, the β-sheet forming peptide sequence is exactly 5 amino acids in length and has a total propensity for forming β-sheet configurations of at least 5.5. In some embodiments, the β-sheet forming peptide sequence is exactly 5 amino acids in length and has a total propensity for forming β-sheet configurations of at least 7. In some embodiments, the β-sheet forming peptide sequence is exactly 6 amino acids in length and has a total propensity for forming β-sheet configurations of at least 6. In some embodiments, the β-sheet forming peptide sequence is exactly 6 amino acids in length and has a total propensity for forming β-sheet configurations of at least 8. In some embodiments, the β-sheet forming peptide sequence is exactly 7 amino acids in length and has a total propensity for forming β-sheet configurations of at least 6.5. In some embodiments, the β-sheet forming peptide sequence is exactly 7 amino acids in length and has a total propensity for forming β-sheet configurations of at least 9. In some embodiments, the β-sheet forming peptide sequence is exactly 8 amino acids in length and has a total propensity for forming β-sheet configurations of at least 7. In some embodiments, the β-sheet forming peptide sequence is exactly 8 amino acids in length and has a total propensity for forming β-sheet configurations of at least 10. In some embodiments, the β-sheet forming peptide sequence is exactly 9 amino acids in length and has a total propensity for forming β-sheet configurations of at least 7.5. In some embodiments, the β-sheet forming peptide sequence is exactly 9 amino acids in length and has a total propensity for forming β-sheet configurations of at least 11. In some embodiments, the β-sheet forming peptide sequence is exactly 10 amino acids in length and has a total propensity for forming β-sheet configurations of at least 8. In some embodiments, the β-sheet forming peptide sequence is exactly 10 amino acids in length and has a total propensity for forming β-sheet configurations of at least 12.

The β-sheet forming peptide sequence may comprise any suitable number and combination of amino acids to achieve a sufficient total propensity for forming β-sheet conformations. In some embodiments, the β-sheet forming peptide sequence is 4-10 amino acids in length and 50% of the amino acid residues are valine residues. In some embodiments, the β-sheet forming peptide sequence is 4-10 amino acids and length and each of the 4-10 amino acid residues is independently selected from valine (V), glutamic acid (E), and aspartic acid (D). In some embodiments, the β-sheet forming peptide sequence is 4-10 amino acids and length and comprises 50% valine residues in combination with D and/or E residues. Exemplary sequences for the β-sheet forming peptide sequence include: VVEE (SEQ ID NO: 1), VEVE (SEQ ID NO: 2), EVEV (SEQ ID NO: 3), VVVEEE (SEQ ID NO: 4), VEVEVE (SEQ ID NO: 5), EVEVEV (SEQ ID NO: 6), VVVVEEEE (SEQ ID NO: 7), VEVEVEVE (SEQ ID NO: 8), EVEVEVEV (SEQ ID NO: 9), and other sequences of 4-10 amino acids in length comprising a combination of V and E residues, or sequences of 4-10 amino acids in length comprising 50% valine residues in combination with E and/or D residues.

In some embodiments, the β-sheet forming peptide sequence comprises VVEE (SEQ ID NO: 1), VEVE (SEQ ID NO: 2), or EVEV (SEQ ID NO: 3).

In some embodiments, the β-sheet forming peptide sequence is conjugated to at least three vinylidene fluoride (VDF) monomers. In other words, in some embodiments the β-sheet forming peptide sequence is conjugated a PVDF comprising at least three VDF monomers. In some embodiments, the β-sheet forming peptide sequence is conjugated to 3-10 VDF monomers. In some embodiments, the β-sheet forming peptide sequence three VDF monomers (VDF3), four VDF monomers (VDF4), five VDF monomers (VDF5), or six VDF monomers (VDF6). In some embodiments, the β-sheet forming peptide sequence is directly conjugated to (e.g. covalently bound to) the two or more VDF monomers. In other words, in some embodiments the β-sheet forming peptide sequence is covalently bound to the two or more VDF monomers without requiring a linker.

In some embodiments, the peptide amphiphile comprises VDF6-EVEV (SEQ ID NO: 3). In some embodiments, the peptide amphiphile comprises VDF6-VEVE (SEQ ID NO: 2). In some embodiments, the peptide amphiphile comprises VDF6-VVEE (SEQ ID NO: 1). Exemplary peptide amphiphile structures are shown in FIGS. 1A, 1B, and 1C.

In some embodiments, the peptide amphiphile further comprises a terminal group. The terminal group is attached to the terminal amino acid in the β-sheet forming peptide sequence (e.g. the amino acid not attached at one end to either another amino acid or to a VDF monomer). In some embodiments, the terminal group comprises a carboxylic group. For example, in some embodiments the terminal group is carboxylic acid.

Figures 1E, 1F, 1G:
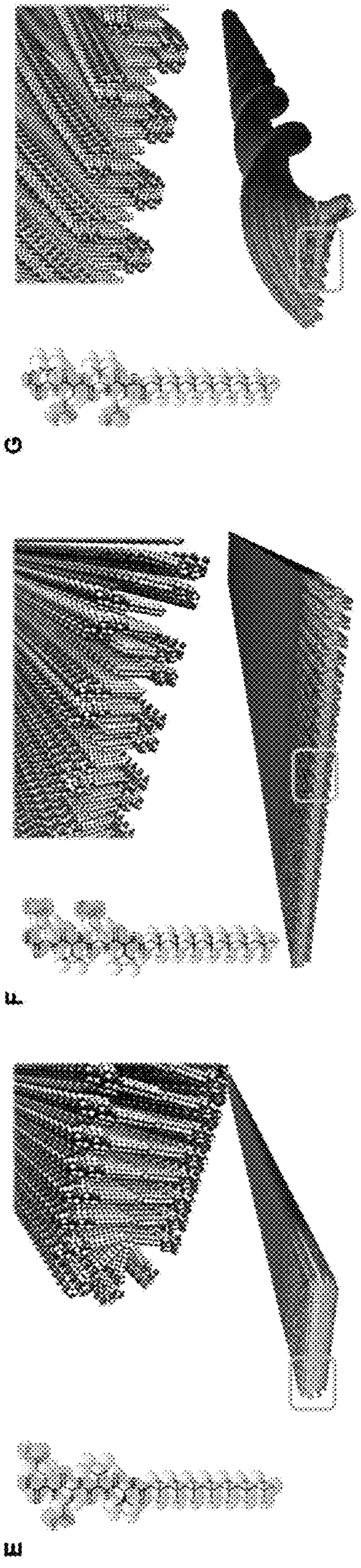

In some embodiments, provided herein are nanoscale ferroelectric structures comprising a plurality of self-assembled peptide amphiphiles described herein. In some embodiments, provided herein are nanoscale ferroelectric structures comprising a plurality of self-assembled peptide amphiphiles, each peptide amphiphile comprising a β-sheet forming peptide sequence conjugated to two or more vinylidene fluoride (VDF) monomers. The PAs described herein are shown to self-assemble into different conformations (e.g. narrow ribbons, flat ribbons, twisted ribbons) depending on the sequence of the β-sheet forming peptide. The nanoscale ferroelectric structure may display any suitable conformation depending on the precise PA used. Exemplary conformations are shown in FIG. 1E, FIG. 1F, and FIG. 1G.

In some embodiments, the PAs described herein self-assemble into a nanoscale ferroelectric structure (e.g. a ribbon) having a thickness of about 4 nm to about 6 nm. In some embodiments, the structure has a thickness of about 4 nm to about 5 nm. In some embodiments, the structure has a thickness of about 4.5 nm. In some embodiments, the structure has a thickness of about 5 nm to about 6 nm. In some embodiments, the structure has a thickness of about 5.5 nm.

In some embodiments, the β-sheet forming peptide sequence of each peptide amphiphile in the nanoscale ferroelectric structure has a total propensity for forming β-sheets of at least 4.5. In some embodiments, the β-sheet forming peptide sequence of each peptide amphiphile in the nanoscale ferroelectric structure has a total propensity for forming β-sheets of at least 5. As described above, the total propensity for forming β-sheets for each peptide amphiphile in the structure varies depending on the number of amino acids present in the β-sheet forming peptide sequence. Exemplary peptide amphiphiles for inclusion in a nanoscale ferroelectric structure are described above. Any of the above-described peptide amphiphiles may be used in a nanoscale ferroelectric structure.

In some embodiments, the β-sheet forming peptide sequence of each peptide amphiphile in the nanoscale ferroelectric structure comprises VVEE (SEQ ID NO: 1), VEVE (SEQ ID NO: 2), or EVEV (SEQ ID NO: 3). In some embodiments, the nanoscale ferroelectric structure comprises a plurality of PAs, wherein each PA has the same β-sheet forming peptide sequence and/or the same number of VDF monomers. In some embodiments, each PA in the nanoscale ferroelectric structure is identical (e.g. has the same β-sheet forming peptide sequence and the same number of VDF monomers). In some embodiments, each PA in the nanoscale ferroelectric structure not identical. For example, each PA in the nanoscale ferroelectric structure may comprise the same β-sheet forming peptide sequence but PAs may differ in the number of VDF monomers included. As another example, certain PAs in the nanoscale ferroelectric structure may have one β-sheet forming peptide sequence and certain other PAs in the nanoscale ferroelectric structure may have a different β-sheet forming peptide sequence.

In some embodiments, the nanoscale ferroelectric structure comprises a plurality of PAs, wherein the sequence of the β-sheet forming peptide sequence for each PA in the nanoscale ferroelectric structure is independently selected from SEQ ID NO: 1, SEQ ID NO: 2, and SEQ ID NO: 3. For example, in some embodiments a portion of the PAs in the nanoscale ferroelectric structure comprise β-sheet forming peptide sequence of VVEE (SEQ ID NO: 1) and a portion of the PAs in the nanoscale ferroelectric structure comprise a β-sheet forming peptide sequence of VEVE (SEQ ID NO: 2) or EVEV (SEQ ID NO: 3). As another example, in some embodiments a portion of the PAs in the nanoscale ferroelectric structure comprise a β-sheet forming peptide sequence of VEVE (SEQ ID NO: 2) and a portion of the PAs in the nanoscale ferroelectric structure comprise a β-sheet forming peptide sequence of VVEE (SEQ ID NO: 1) or EVEV (SEQ ID NO: 3). As another example, in some embodiments a portion of the PAs in the nanoscale ferroelectric structure comprise a β-sheet forming peptide sequence of EVEV (SEQ ID NO: 3) and a portion of the PAs in the nanoscale ferroelectric structure comprise a β-sheet forming peptide sequence of VVEE (SEQ ID NO: 1) or VEVE (SEQ ID NO: 2).

The number of VDF monomers may be the same in each PA in the structure, or may differ between PAs in the structure. PAs in the nanostructure may contain 3-10 VDF monomers. In some embodiments, PAs in the nanostructure contain 3, 4, 5, or 6 VDF monomers. In some embodiments, the β-sheet forming peptide sequence of each peptide amphiphile is conjugated to three VDF monomers (VDF3), four VDF monomers (VDF4), five VDF monomers (VDF5), or six VDF monomers (VDF6). In some embodiments, each peptide amphiphile comprises VDF6-EVEV (SEQ ID NO: 3), VDF6-VEVE (SEQ ID NO: 2), or VDF6-VVEE (SEQ ID NO: 1).

In some embodiments, the structure has a Curie temperature ($T_c$) of at least 80° C. In some embodiments, the structure has a Curie temperature ($T_c$) of at least 85° C., at least 90° C., at least 95° C., at least 100° C., at least 105° C., or about 110° C.

EXAMPLES

Example 1

Described herein is the use of supramolecular peptide chemistry to direct the crystal domain structures of VDF oligomers in water-soluble and biodegradable self-assembled filaments. Using VDF oligomers as hydrophobic tails, peptide amphiphiles (PA) were designed to form supramolecular nanostructures with different morphologies, since wider nanostructures should allow for larger ferroelectric crystal domains. β-sheet forming peptide sequences VVEE (SEQ ID NO: 1), VEVE (SEQ ID NO: 2) and EVEV (SEQ ID NO: 3) (V=valine, E=glutamic acid) can direct the formation of different morphologies such as fibers, ribbons and narrow twisted ribbons, respectively (*J. Am. Chem. Soc.* 136, 12461-12468 (2014)). These three different morphologies of nanostructures were chosen to program the ferroelectric phase and domain sizes of VDF crystals within the PA assemblies. It was hypothesized that the molecules would spontaneously crystallize with the polar axes aligned in the hydrogen bonding direction.

Morphology and Crystal Structures

Figures 5A, 5B, 5C, 5D, 5E, 5F, 5G, 5H, 5I, 5J, 5K, 5L:
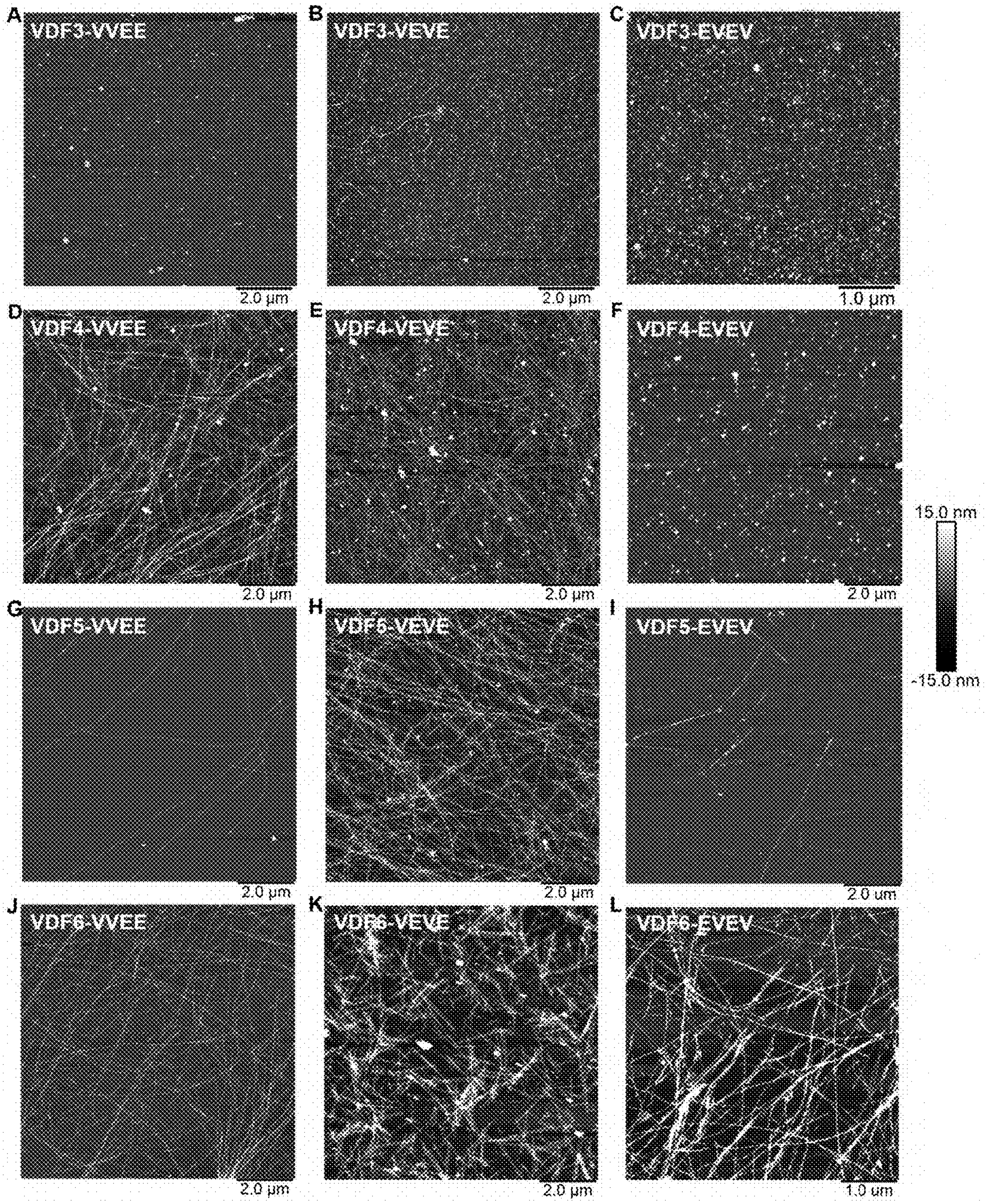
FIGS. 5A-5L show AFM morphology images on liquid samples of VDF-PA assemblies annealed in 20 mM solutions.
Figures 6A, 6B, 6C, 6D, 6E, 6F, 6G, 6H, 6I:
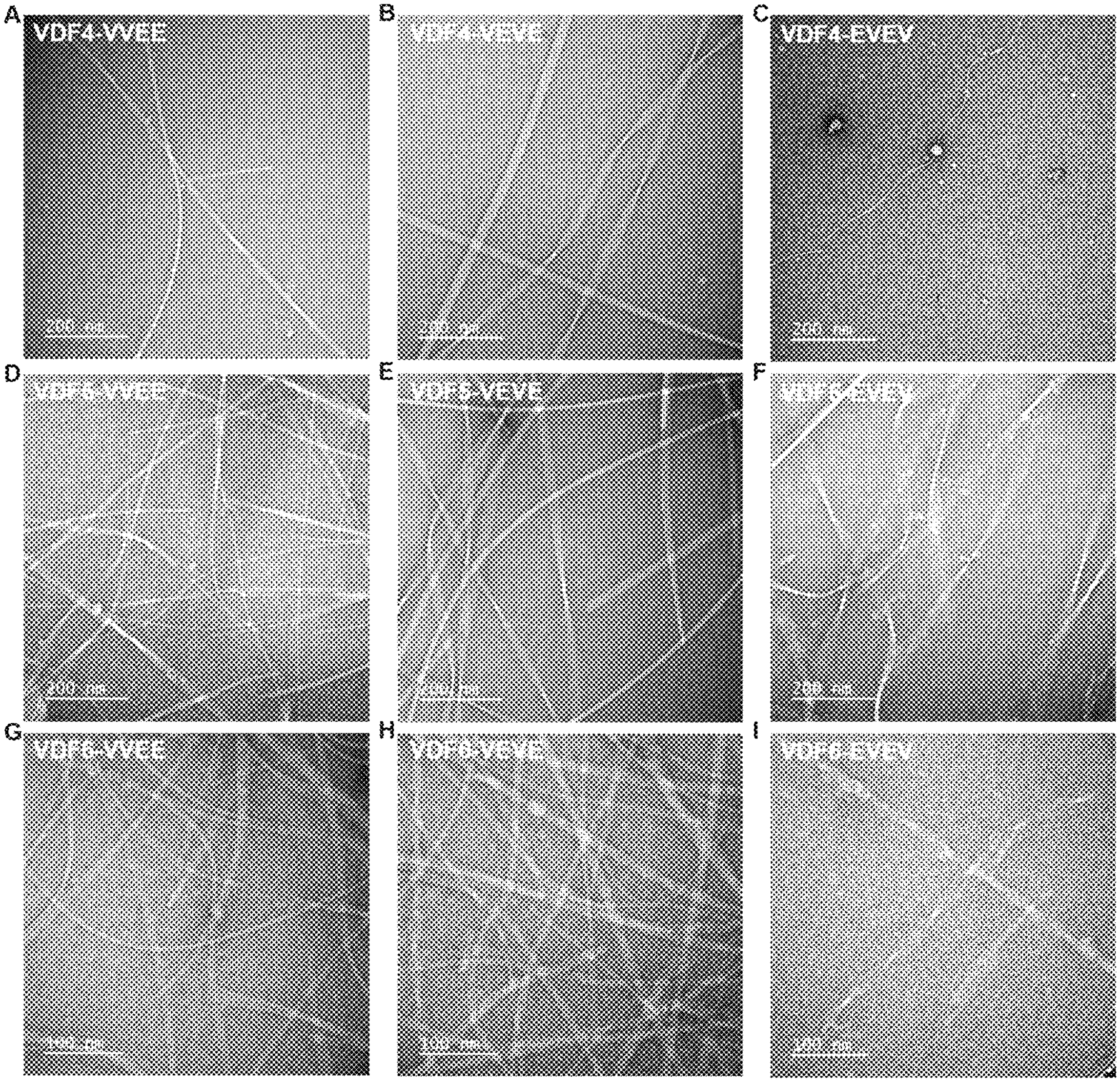
FIGS. 6A-6I show TEM images of the dry-state VDF-PA assemblies annealed in 10 mM solutions.
Figures 7A, 7B, 7C:
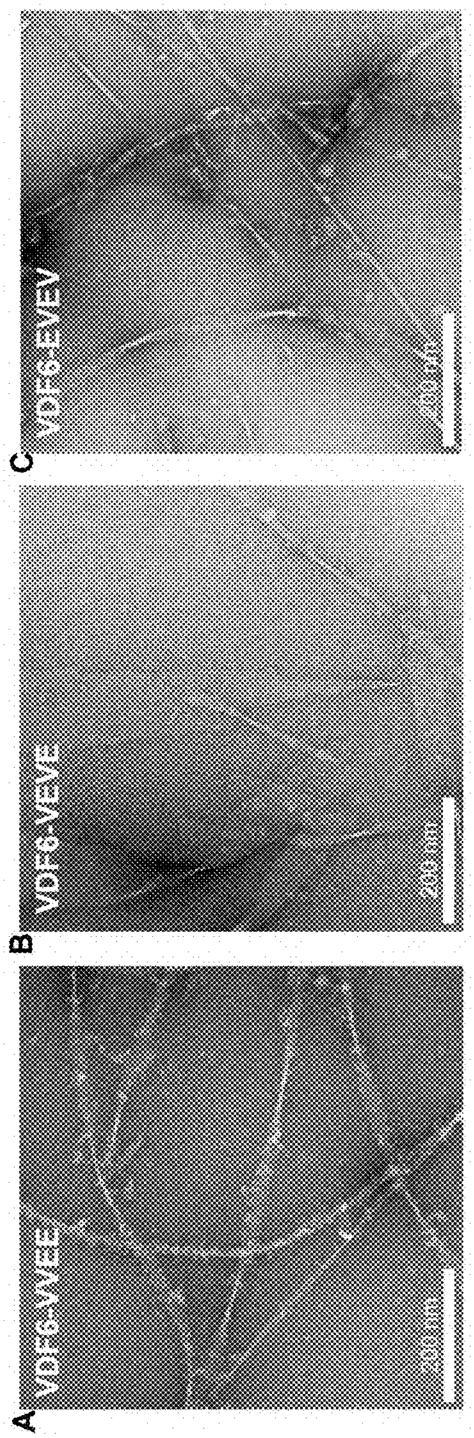
FIGS. 7A-7C show TEM images of the dry-state VDF-PA assemblies annealed in 20 mM solutions.
Figures 8A, 8B, 8C, 8D, 8E, 8F:
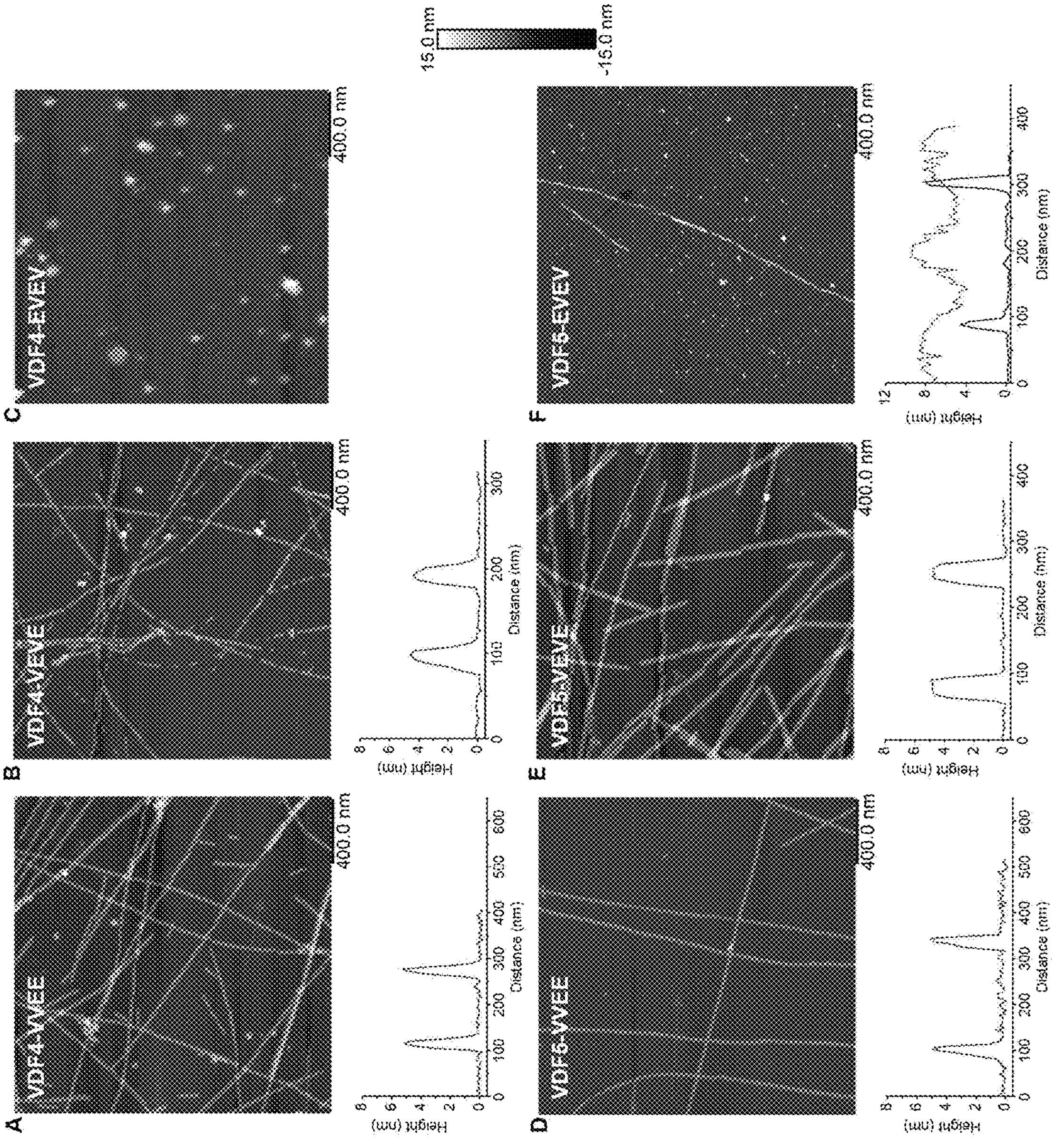
FIGS. 8A-8F show AFM morphology images coupled with height measurements along the arrows on liquid samples of VDF-PA assemblies annealed in 20 mM solutions.
Figures 9A, 9B, 9C:
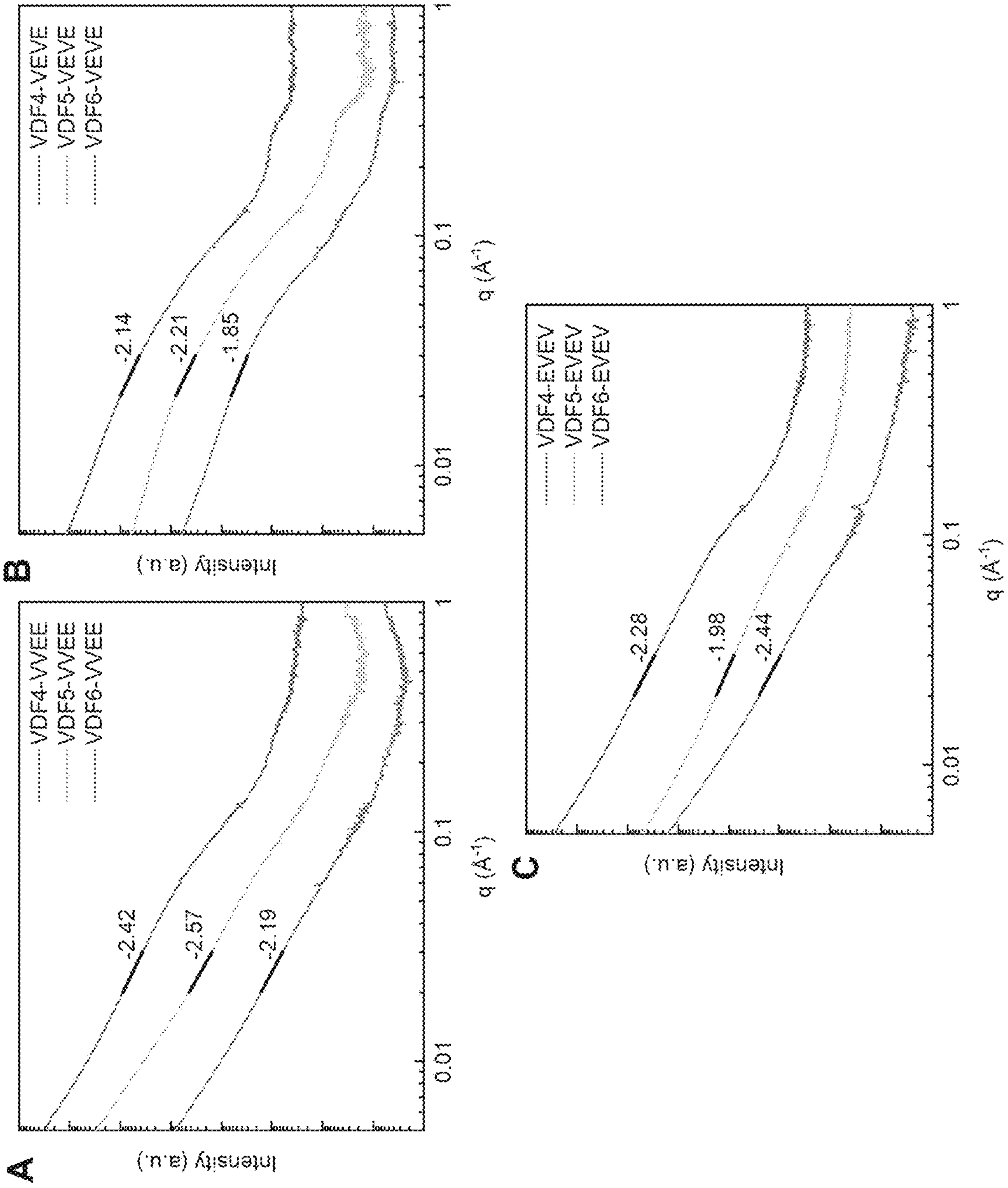
FIGS. 9A-9C show small angle X-ray scattering (SAXS) spectra of the 10 mM annealed VDF-PA solutions of (FIG. 9A) VDF-VVEE (SEQ ID NO: 1), (FIG. 9B) VDF-VEVE (SEQ ID NO: 2) and (FIG. 9C) VDF6-EVEV (SEQ ID NO: 3). The scattering intensities were offset vertically for clarity.

To create supramolecular nanostructures of different morphologies, β-sheet forming peptide sequences VVEE (SEQ ID NO: 1), VEVE (SEQ ID NO: 2) and EVEV (SEQ ID NO: 3) were synthesized and covalently attached to VDF oligomers to provide the 12 VDF-PAs illustrated in FIG. 1A (see Methods). The oligomers were prepared with three to six VDF repeat units (VDF3 to VDF6) and terminated with carboxylic acids. The three PAs were also prepared with nonfluorinated C16 tails as controls. After heating aqueous solutions of the VDF-PAs to 80° C. and slowly cooling to room temperature, they all form well-defined supramolecular structures with lengths on the order of microns, except for the VDF3-PAs and VDF4-EVEV (SEQ ID NO: 3) which mainly shows micelles by liquid state atomic force microscopy (AFM) (FIG. 5). Transmission electron microscopy (TEM) indicates that the supramolecular structures of the VDF-PA assemblies are retained in the dry state (FIG. 6). As shown by liquid state AFM in FIG. 1B, VDF6-VVEE (SEQ ID NO: 1) PA forms narrow ribbons with an average width of about 30 nm. In contrast, VDF6-VEVE (SEQ ID NO: 2) forms flat ribbons with widths greater than 100 nm (FIG. 1C and FIG. 7), suggesting the potential to form larger 2D crystals. Interestingly, as the charged glutamic acid side chains are moved closer to the hydrophobic tails in VDF6-EVEV (SEQ ID NO: 3), a highly twisted ribbon morphology is formed with an average width of 30 to 50 nm and pitch length of about 70 nm (FIG. 1D). The high repulsions between the EVEV (SEQ ID NO: 3) sequences limited the lateral growth of the loosely assembled structures in which the natural twisting of β-sheets can be easily accommodated. Height measurements by AFM indicate that VDF6-VVEE (SEQ ID NO: 1) assembles into thick ribbons (5.5 nm), suggesting a bilayer structure without interdigitation (FIG. 1E). In contrast, VDF6-VEVE (SEQ ID NO: 2) and VDF6-EVEV (SEQ ID NO: 3) show ribbons with a height of about 4.5 nm, consistent with interdigitation of the VDF tails, as illustrated in FIGS. 1F and G. These dimerized units favor the formation of flat morphology that eliminates the interfacial curvature between the peptide segments and the tail. The assemblies with VDF4 and VDF5 tails show packing analogous to the corresponding VDF6-PAs with the ribbon heights from 4.5 to 5.5 nm (FIG. 8). Small-angle X-ray scattering (SAXS) patterns of the VDF-PAs show slopes of around-2 (FIG. 9), consistent with the ribbon structures observed by TEM and AFM.

Fourier-transform infrared (FTIR) spectroscopy was performed to demonstrate the crystal phases of VDF regions in VDF-PA assemblies. As shown in the attenuated total reflectance (ATR) FTIR spectra (FIG. 2, A to C), all the annealed VDF-PAs with tails length longer than four VDF monomers show peaks characteristic of the VDF electroactive β-phase at 1275 $cm^{-1}$ ($CF_2$ symmetric stretching) and 837 $cm^{-1}$ ($CH_2$ rocking) and amide I band in-sheet peptides around 1622-1631 $cm^{-1}$ (C═O stretching). The absorption peaks of the β-sheet become sharper and exhibit a redshift as the length of the VDF tail increases, indicating elongation of the C═O bond and stronger hydrogen bonding in β-sheet. These results demonstrate that the β-sheet structures can accommodate the VDF crystallization. The vibration bands at 795 $cm^{-1}$ and 837 $cm^{-1}$ result exclusively from the rocking vibration of $CH_2$ in the α- and β-phases of VDF, respectively, and thus can be used to evaluate the fraction of α- and β-phases in the samples. VDF6-VEVE (SEQ ID NO: 3) shows the greatest β-phase VDF content but no α-phase VDF. VDF6-VVEE (SEQ ID NO: 1) also exhibits predominantly β-phase VDF crystallization with an absorption peak weaker than VDF6-VEVE (SEQ ID NO: 2). VDF6-EVEV (SEQ ID NO: 3) shows characteristic bands of both α- and β-phase VDF with low intensity, which may be attributed to large VDF crystal lamellae being unable to exist inside the highly twisted nanoribbon structures.

Figure 10:
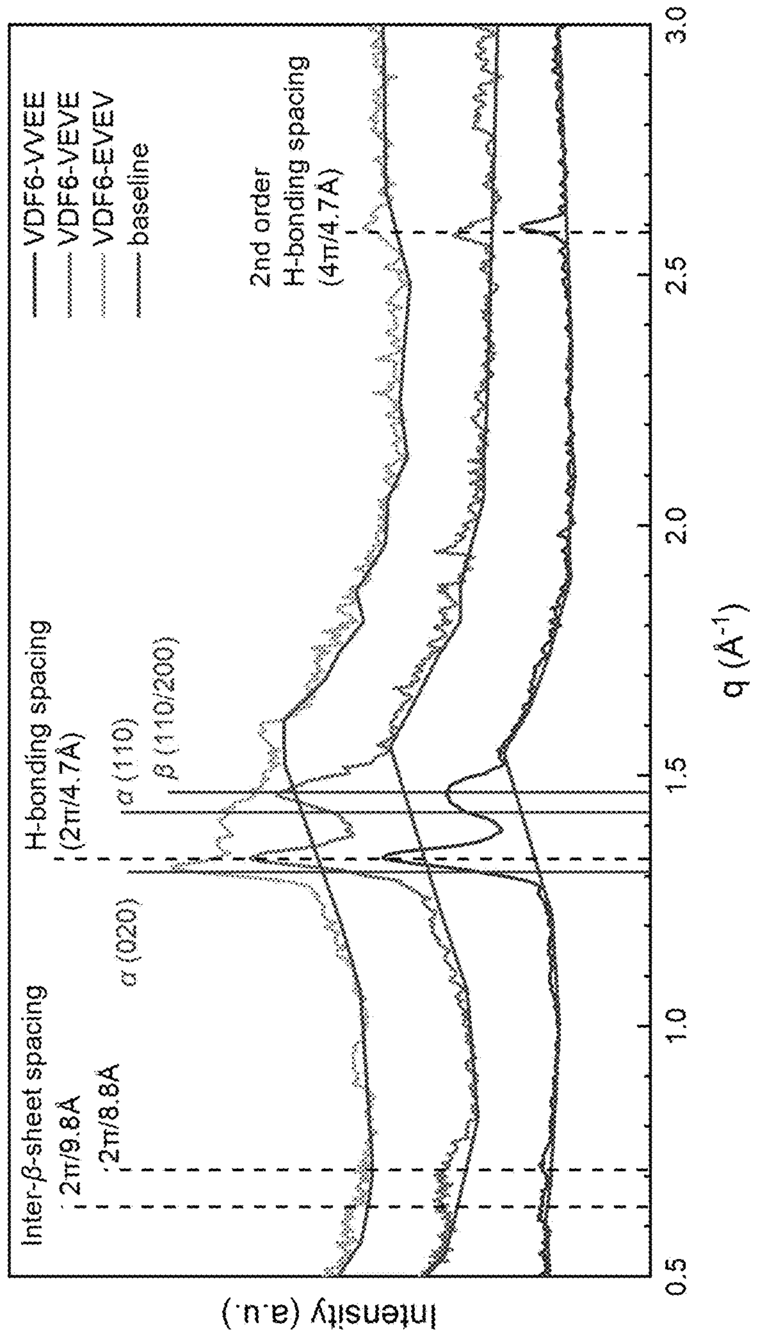
FIG. 10 shows baseline subtraction of X-ray scattering patterns of 10 mM annealed VDF6-VVEE (SEQ ID NO: 1), VDF6-VEVE (SEQ ID NO: 2) and VDF6-EVEV (SEQ ID NO: 3) solutions in MAXS and WAXS regions. The scattering intensities were offset vertically for clarity.
Figure 11:
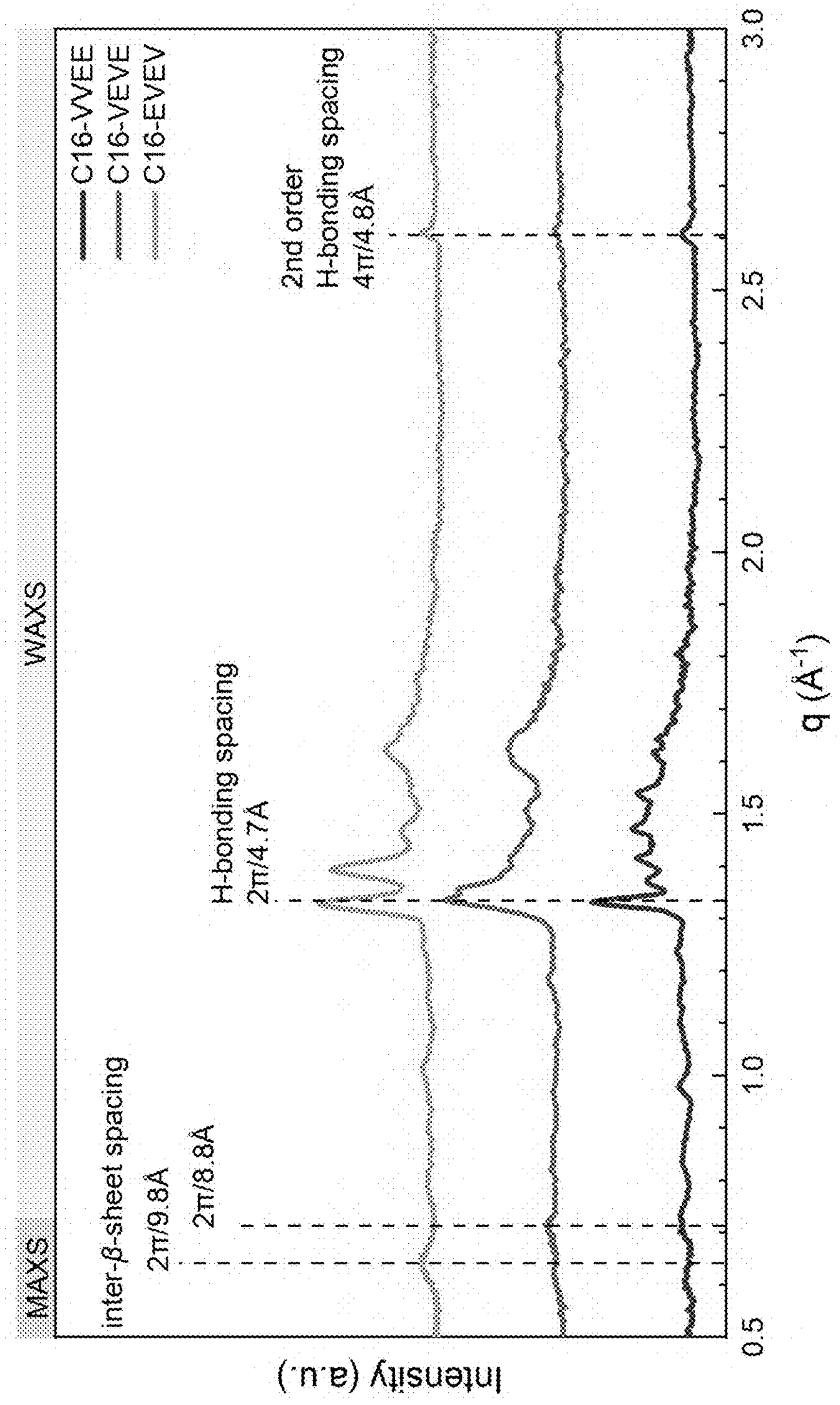
FIG. 11 shows X-ray scattering patterns of 10 mM annealed C16-VVEE (SEQ ID NO: 1), C16-VEVE (SEQ ID NO: 2) and C16-EVEV (SEQ ID NO: 3) solutions in MAXS and WAXS regions. The scattering intensities were offset vertically for clarity.

Given the above spectroscopic evidence of dominant β-phase VDF formation with VEVE (SEQ ID NO: 2) and VVEE (SEQ ID NO: 1) β-sheets and the mixture of weak α- and β-phase crystals in EVEV PA assemblies, these systems were further characterized by solution wide angle X-ray scattering (WAXS). For reference, the unit cells of the non-polar α-phase and polar β-phase VDF crystals are illustrated in FIG. 10. WAXS patterns of the VDF-PAs (FIG. 2D) and the C16-PAs with amorphous nonfluorinated tails show primary peaks around q=1.34 $Å^{-1}$ consistent with the intermolecular hydrogen bonding spacing of 4.7 Å expected for β-sheets. This indicates that the β-sheet formation dominates the crystal structures of the VDF-PA assemblies. Because the β-sheet hydrogen bonding spacing is close to the a axis spacing of the α-phase VDF crystal (4.96 Å) and the b axis spacing of the β-phase VDF crystal (4.91 Å) (FIG. 10), it was proposes that VDF crystallization is concomitant with the β-sheet formation. Different from the C16-PAs, VDF6-VVEE (SEQ ID NO: 1) and VDF6-VEVE (SEQ ID NO: 2) show strong scattering peaks at q=1.47 $Å^{-1}$ corresponding to the 110/200 reflection of β-phase VDF while VDF6-EVEV (SEQ ID NO: 3) shows scattering peaks of both α (110 and 020 reflections) and weak β (110/200) VDF crystals, consistent with the FTIR results. In the middle angle X-ray scattering (MAXS) region in FIG. 2D and VVEE (SEQ ID NO: 1) and VEVE (SEQ ID NO: 2) PA assemblies mainly show a lateral spacing of 8.8 Å between β-sheets while EVEV PA assemblies show larger inter-β-sheet spacing of around 9.8 Å, \matching the lateral a axis spacing of β VDF crystal (8.58 Å) and b axis spacing of a VDF crystal (9.64 Å), respectively.

Figures 2A, 2B, 2C, 2D, 2E, 2F:
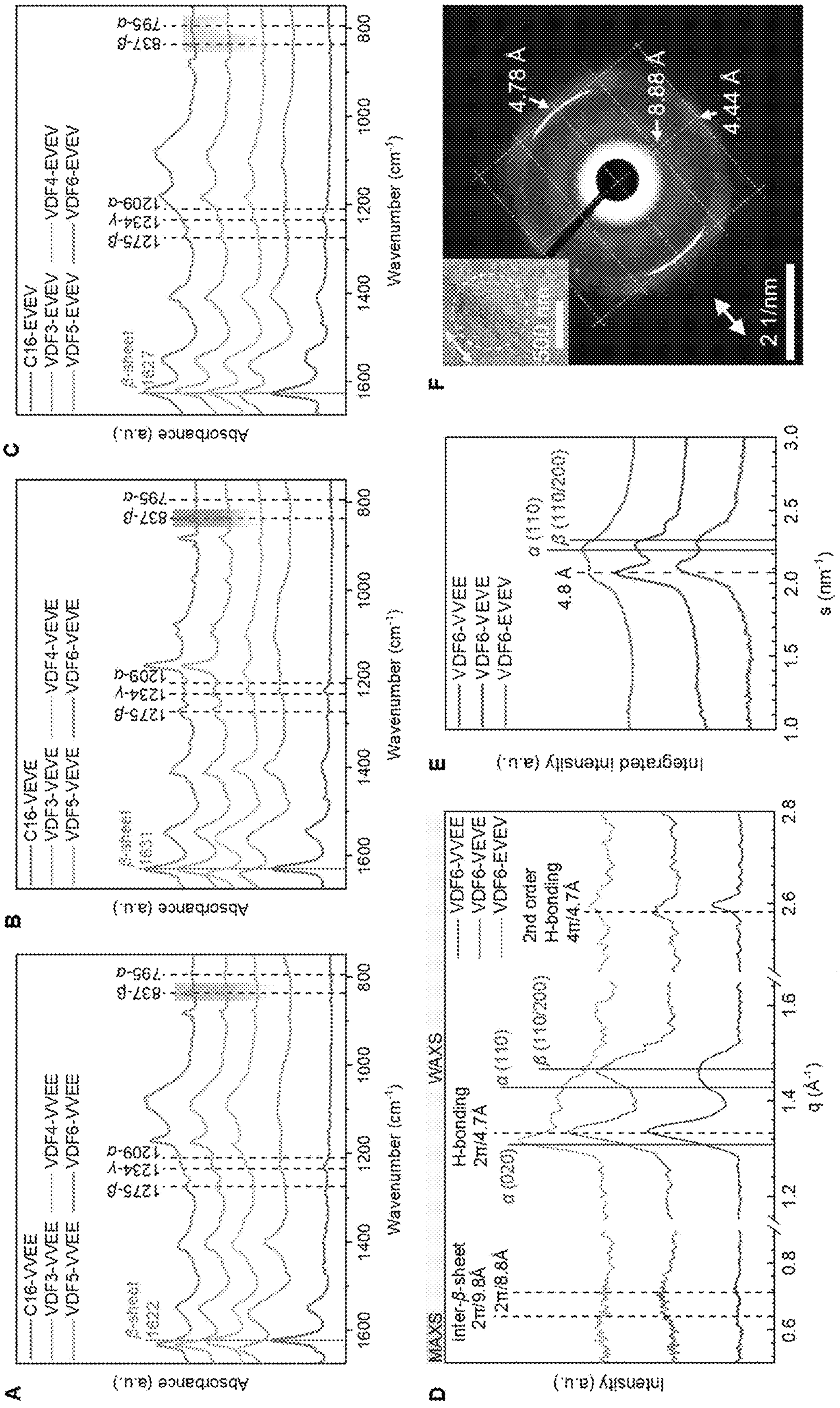

Selected-area electron diffraction (SAED) on dry-state samples with the partially aligned ensemble of the supramolecular assemblies was performed to reveal the orientation of the crystal structures. Azimuthally integrated SAED intensities from the 2D patterns show the diffraction features consistent with the WAXS patterns (FIG. 2D), indicating retained crystal structures of the VDF-PA assemblies in dry state. As shown in FIGS. 2F and G, the SAED patterns of VDF6-VVEE (SEQ ID NO: 1) and VDF6-EVEV (SEQ ID NO: 3) assemblies exhibit four-quadrant symmetry along and perpendicular to the direction of alignment. The innermost reflection corresponding to the spacing of 8.88 Å and the outermost peaks at 4.44 Å in FIG. 2F are assigned to the inter-β-sheet spacing (10) and its second order reflection (20) in the direction perpendicular to the fiber alignment of VDF6-VVEE (SEQ ID NO: 1). The strong diffraction arcs at 4.78 Å are assigned to the intermolecular hydrogen bonding spacing (01) along the elongation direction of the fibers while the nearby shoulders are indexed as (11) reflections at 4.21 Å. The SAED pattern of VDF6-VEVE (SEQ ID NO: 2) in FIG. 2G shows similar reflections of d spacing as VDF6-VVEE (SEQ ID NO: 1) that are consistent with the WAXS peak spacings. Because of the large amount of short filaments lack of orientation after the sample preparation, the SAED of VDF6-EVEV (SEQ ID NO: 3) shows more ring-like patterns at 4.85 Å and 4.51 Å corresponding to hydrogen bonding spacing and second order reflections of β-sheet structures.

Formation of VDF Crystals in PA Assemblies

Figure 12:
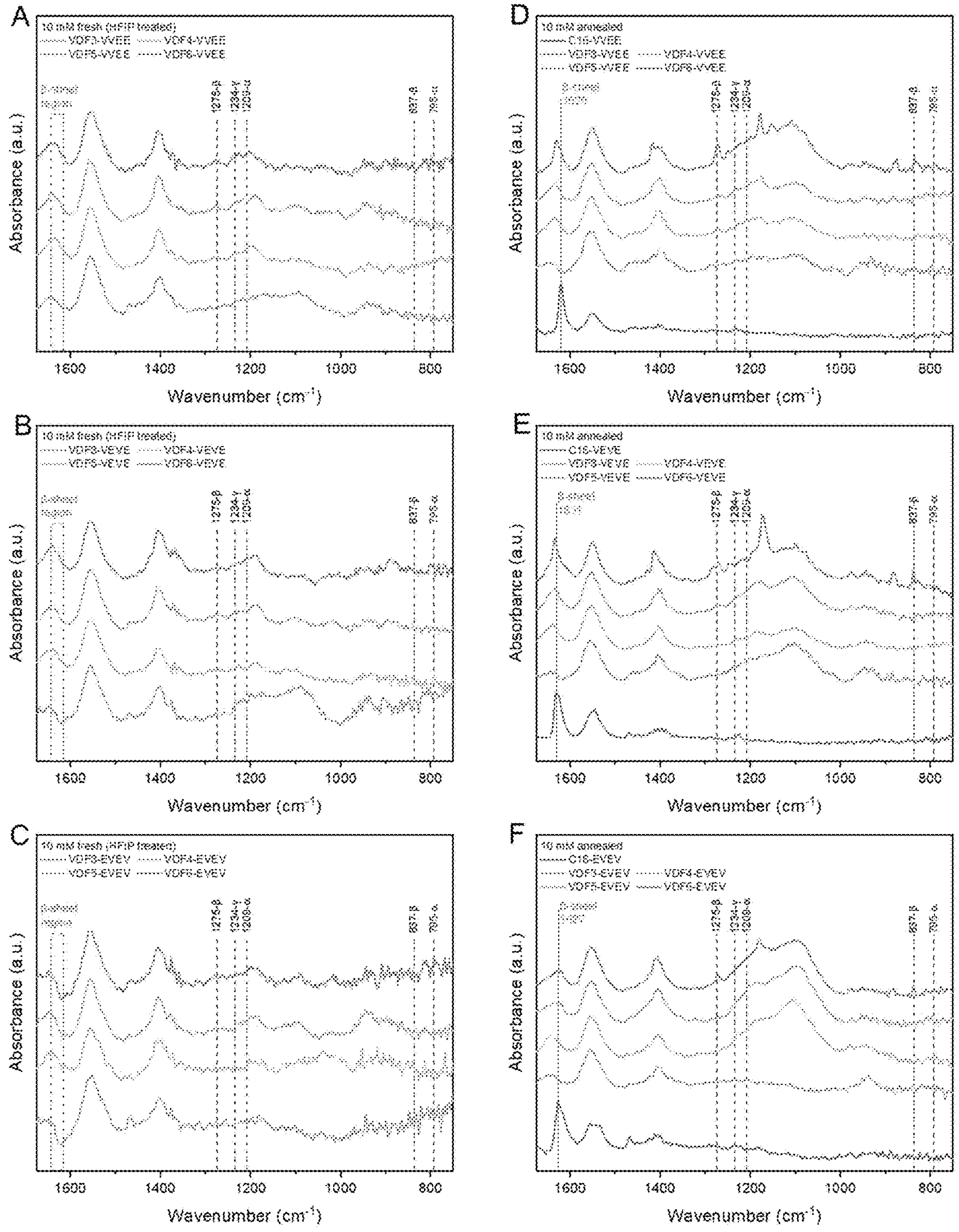
FIGS. 12A-12F show ATR-FTIR spectra of (FIG. 12A, FIG. 12D) VDF-VVEE (SEQ ID NO: 1), (FIG. 12B, FIG. 12E) VDF-VEVE (SEQ ID NO: 2) and (FIG. 12C, FIG. 12F) VDF-EVEV (SEQ ID NO: 3) samples in 10 mM fresh aqueous solution after HFIP treatment (FIG. 12A, FIG. 12B, FIG. 12C) then annealed at 80° C. for 1 h (FIG. 12D, FIG. 12E, FIG. 12F). The β-sheet bands in $H_2O$ (1643-1615 $cm^{-1}$) are highlighted in dashed box. The spectra of C16 PAs with the same peptide sequence heads are added for comparison. The absorbance intensities were offset vertically for clarity.
Figures 13A, 13B, 13C:
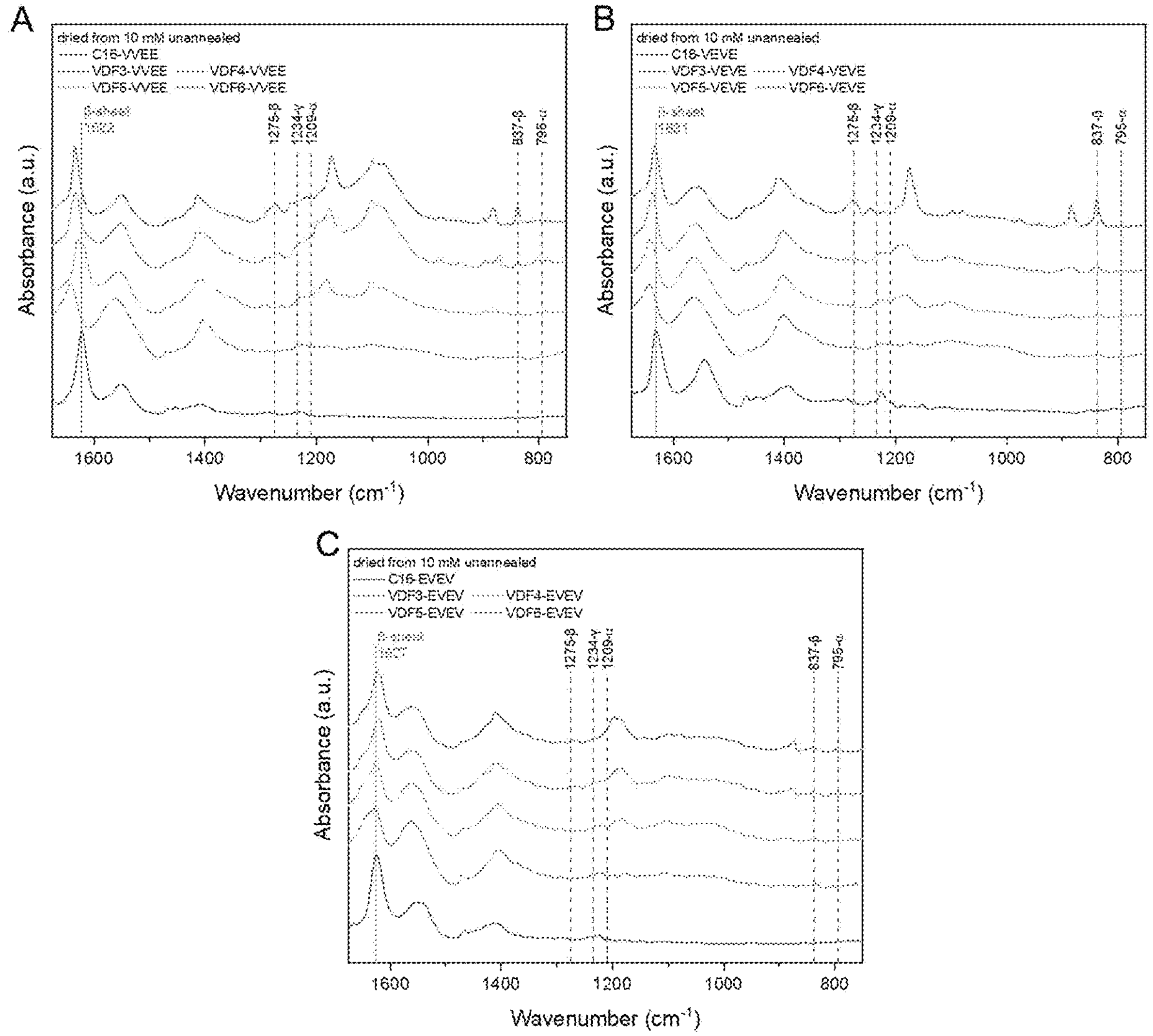
FIGS. 13A-13C show ATR-FTIR spectra of (FIG. 13A) VDF-VVEE (SEQ ID NO: 1), (FIG. 13B) VDF-VEVE (SEQ ID NO: 2) and (FIG. 13C) VDF-EVEV (SEQ ID NO: 3) samples dried from fresh aqueous solution after HFIP treatment. The spectra of C16 PAs with the same peptide sequence heads are added for comparison. The absorbance intensities were offset vertically for clarity.
Figure 14:
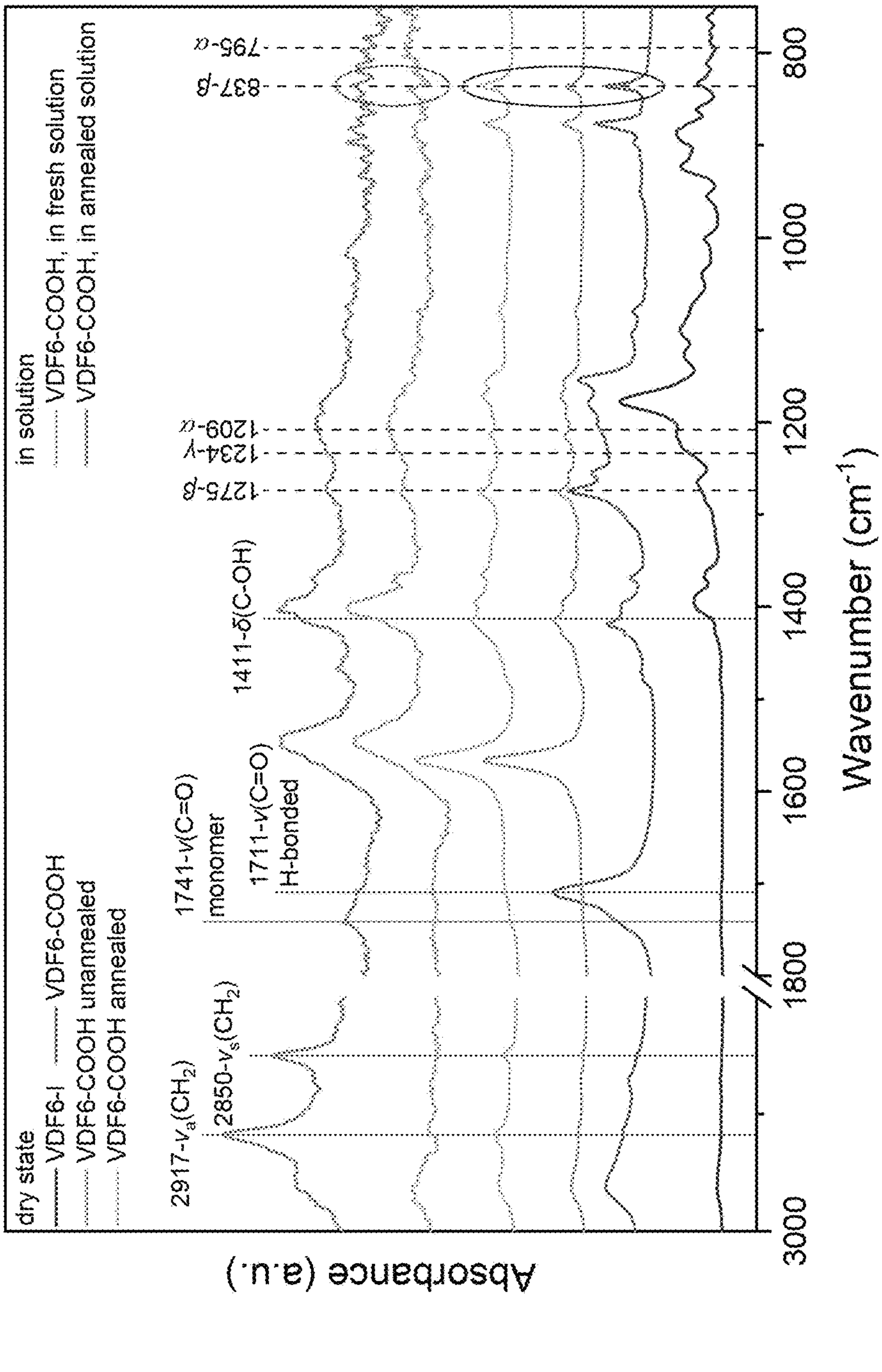
FIG. 14 shows ATR-FTIR spectra of VDF6-I and VDF6-COOH samples in dry state and solution. The lower circle highlights the observation of β-phase VDF in dry state VDF-COOH sample while the higher circle highlights the absence of β-phase VDF in aqueous solution of VDF-COOH. The vibration bands are labeled as: asymmetric stretching $\nu_a(CH_2)$ at 2917 $cm^{-1}$, symmetric stretching vs $(CH_2)$ at 2850 $cm^{-1}$, stretching of C═O in carboxyl monomer ν(C═O) at 1741 $cm^{-1}$, stretching of C═O in hydrogen bonded carboxyl ν(C═O) at 1711 $cm^{-1}$, bending of C—OH in carboxyl δ(C═OH) at 1411 $cm^{-1}$ and vibration peaks assigned to α-, β- and γ-phase VDF. The absorbance intensities were offset vertically for clarity.

To investigate the formation of β-phase VDF in VDF-PAs, freshly dissolved solution samples after HFIP treatment were prepared, in which β-sheet structures are destroyed and no absorption peak of β-phase VDF is observed (FIG. 12, A to C). After annealing at 80° C. for 1 h and cooling down to room temperature, β-phase VDF is formed in accompany by an enhanced β-sheet absorption band (FIG. 12, D to F). For the samples dried from fresh aqueous solution, evaporation-induced crystallization of β-phase VDF is also observed (FIG. 13). For the VDF tail without attaching peptides, the vibration of β-phase VDF appears together with the strong absorption peak of hydrogen-bonded carbonyl group in dry state after the hydrolysis and oxidation of VDF6-I to VDF6-COOH (FIG. 14). However, no VDF crystal phase is observed in the aqueous solution either before or after annealing (FIG. 14). Although the strong asymmetric and symmetric stretching vibration peaks of the $CH_2$ group at 2917 and 2850 $cm^{-1}$ suggest packing of the hydrophobic VDF chains in annealed solution, the carboxyl head shows the dominant vibration mode of free monomer (C═O stretching at 1741 $cm^{-1}$) and VDF crystallization is not observed (FIG. 14). pH titration was also performed on the VDF6-VEVE (SEQ ID NO: 2) samples to break the β-sheet structures and simultaneous decay of IR absorption peaks of β-sheet and β-phase VDF as the pH value approaches 9 was observed (FIG. 2I). As the pH value increases to 10, β-phase VDF is negligible while pronounced α-phase VDF emerges, consistent with the thermodynamically favorable α-phase crystallization nature of VDF. These results demonstrate that hydrogen bonding in β-sheet structures of the peptide region, either formed by annealing or evaporation of water, acts as the template for β-phase crystallization of VDF, which was only previously able to be achieved by mechanical extension and extreme electrical poling processes in PVDF polymers.

Figures 15A, 15B, 15C, 15D, 15E, 15F:
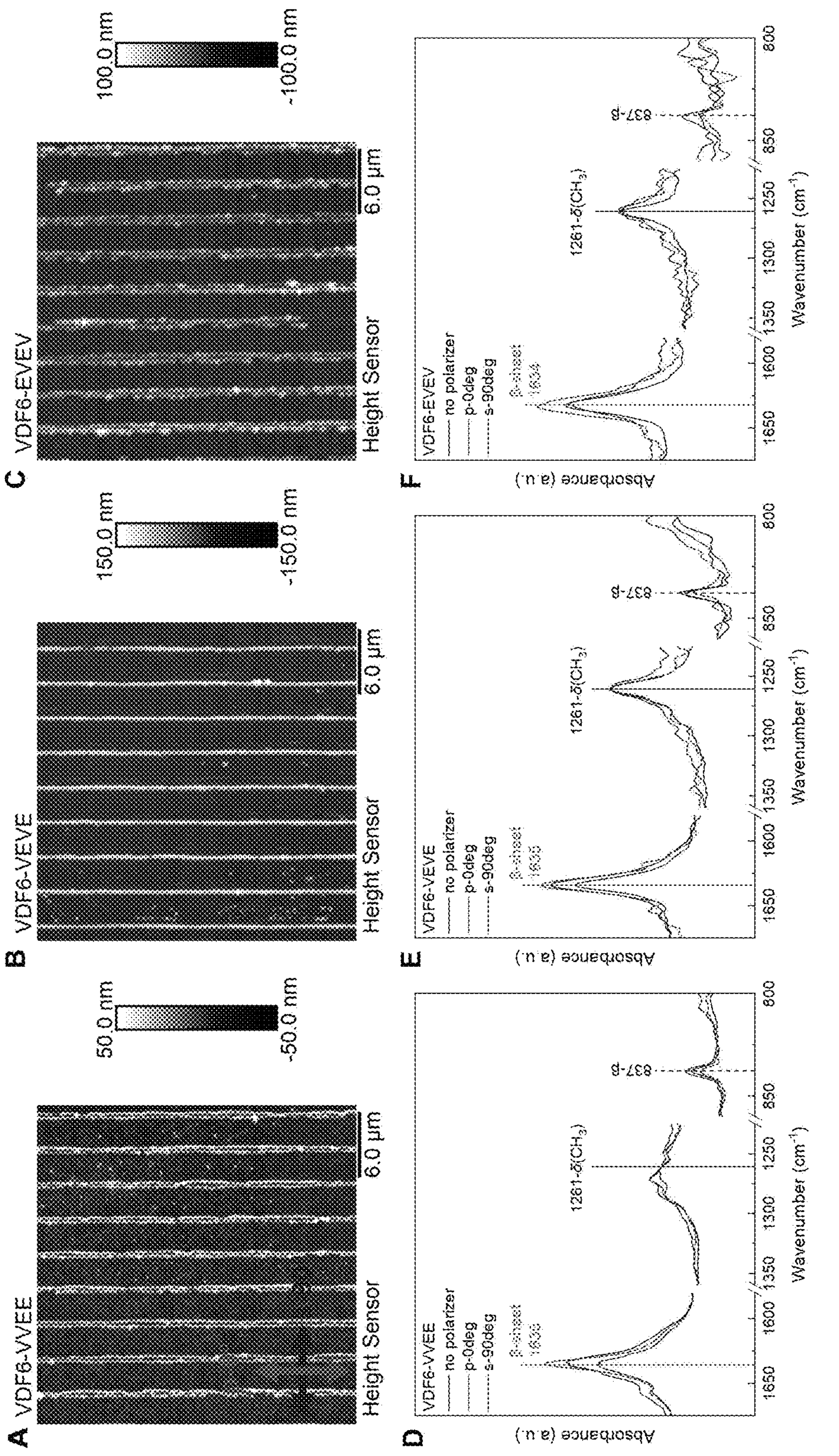
FIGS. 15A-15F show polarized transmission FTIR of the aligned VDF6-PA fibers.

To verify the lattice orientation of β-phase VDF crystals relative to the hydrogen bonding direction in β-sheet peptides, polarized FTIR was performed with the VDF6-PA nanofibers aligned by solution embossing on a Germanium wafer (see Methods and FIG. 15, A to C). Polarized transmission FTIR spectra show that the amide C═O stretching vibration (near 1635 $cm^{-1}$), with the transition dipole moment parallel to the hydrogen bond, is enhanced as the electric field of the incident IR is parallel to the elongation axis of the PA fibers and weakened in the other orthogonal polarization direction (FIG. 15, D to F). This indicates that the hydrogen bonding direction of the β-sheets is parallel to the long axis of the PA fibers. For the absorption peak of $CH_2$ rocking (837 $cm^{-1}$) vibration, with dipole transition moment perpendicular to the polar b axis of β-phase VDF, the intensity changes in an opposite trend indicating that the b axis of β-phase is parallel to the elongation axis or hydrogen bonding direction of the fibers.

Thermodynamics of the VDF-PA Assemblies

Figures 16A, 16B, 16C:
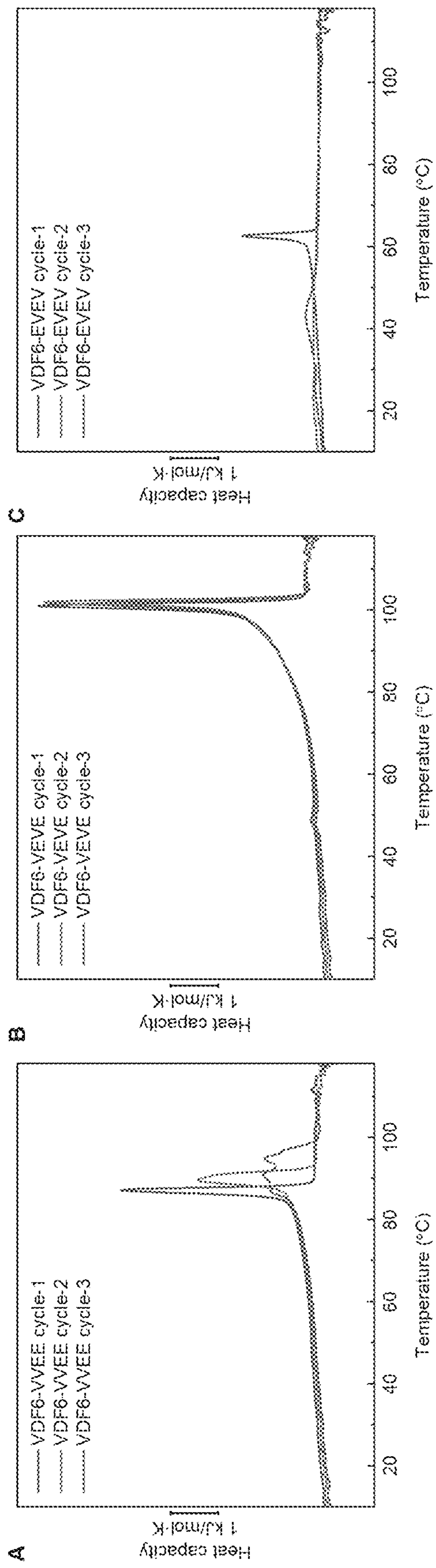
FIG. 16A, FIG. 16B, and FIG. 16C show DSC thermograms of the VDF6-PAs in three continuous heating-cooling cycles with the cooling data presented.
Figure 17:
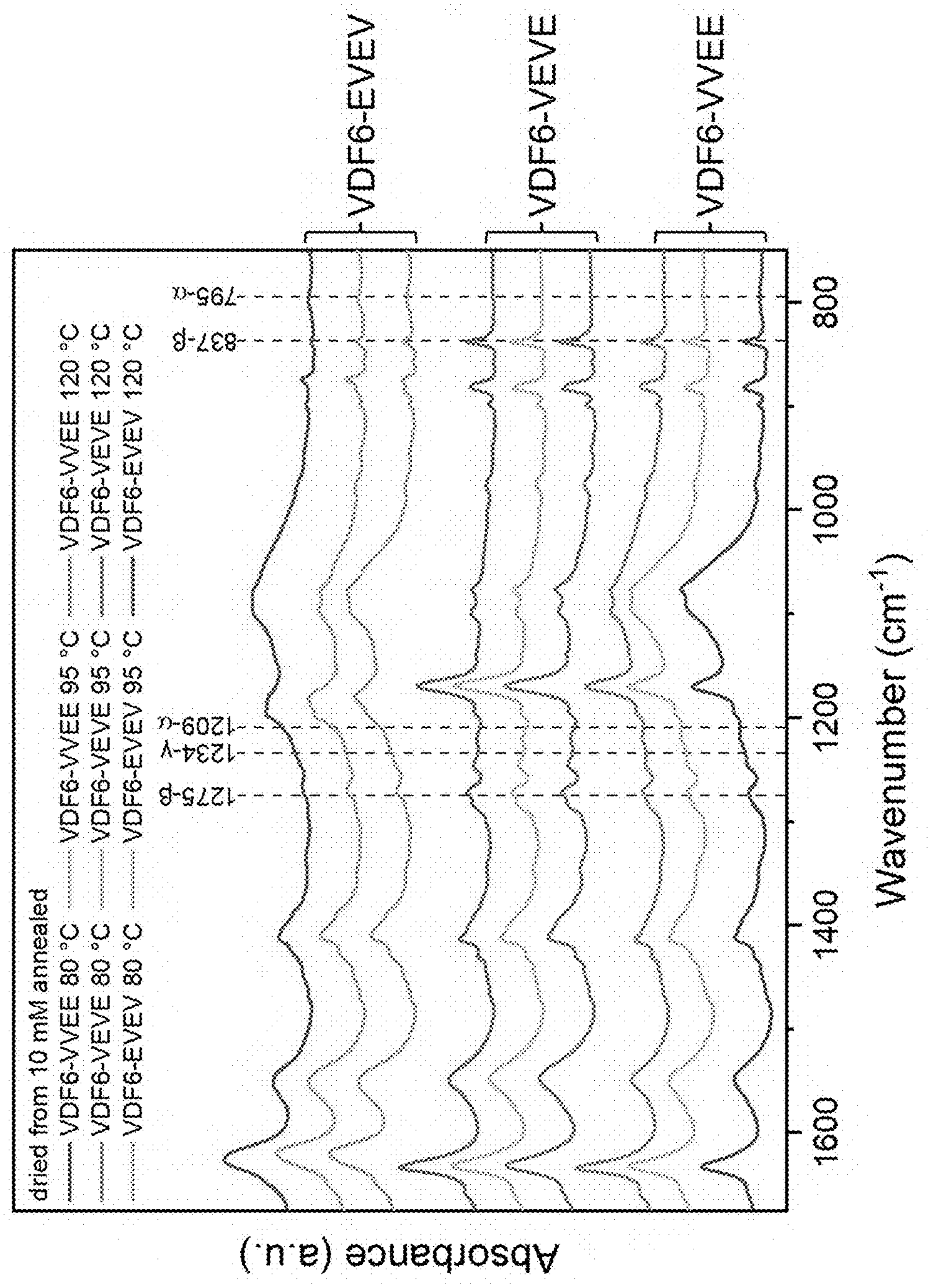
FIG. 17 shows ATR-FTIR spectra of VDF6 PAs dried from 10 mM solutions after annealing at 80° C., 95° C. and 120° C. (by DSC). The absorbance intensities were offset vertically for clarity.

Thermodynamic properties of the VDF-PA assemblies and the embedded β-phase VDF crystals were investigated. Differential scanning calorimetry (DSC) of the annealed VDF-PA solutions shows a huge increase of enthalpy and melting temperature as the tail length increase from 4 to 6 VDF monomers (FIG. 3, A to C), consistent with the increased VDF crystallinity demonstrated by the peak intensity of VDF crystals in FTIR. The single sharp exothermic DSC peak of VDF-PAs indicates that the VDF regions and β-sheets crystalize at the same time within a narrow temperature window, which is different from the slow crystallization process of the peptides themselves as indicated by the slow slopes in DSC curves of C16-PAs with amorphous alkane tail. These sharp phase transition properties together with the simultaneous dissolution of β-sheets and β-phase VDF in the pH titration experiments of the VDF-PA demonstrate the synergistic crystallization behavior of the two regions. In multi-cycle DSC scanning, VDF6-VEVE exhibits its repeatable crystallization behavior while VDF6-VVEE and VDF6-EVEV show decreased enthalpy (FIG. 16), indicating that VDF6-VEVE can crystalize more favorably upon fast cooling. Different from the β-phase crystals in PVDF polymer that usually show transformation to thermodynamically more stable but non-polar α and low-polar γ phases after high-temperature treatment above 90° C., the VDF-PAs show no increase of α or γ phases after annealing at 95° C., slightly below the melting point of VDF6-VEVE (SEQ ID NO: 2) assemblies, and 120° C. (by DSC), and β-phase absorption peaks in VDF6-VVEE (SEQ ID NO: 1) and VDF6-VEVE (SEQ ID NO: 2) are maintained (FIG. 17). Accordingly, the β-sheet structures in peptide regions not only favor the crystallization of β-phase VDF but also can stabilize the β-phase VDF crystals in VDF-PA assemblies.

Figures 3A, 3B, 3C:
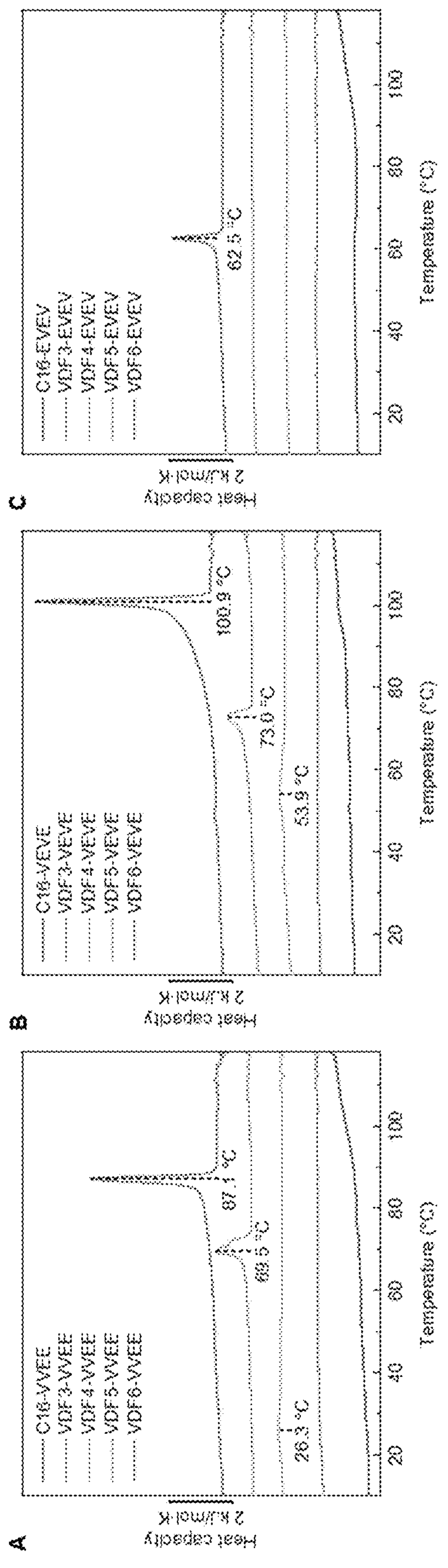
FIGS. 3A-3I show thermodynamic behaviors of the VDF-PA assemblies.
Figures 3D, 3E, 3F:
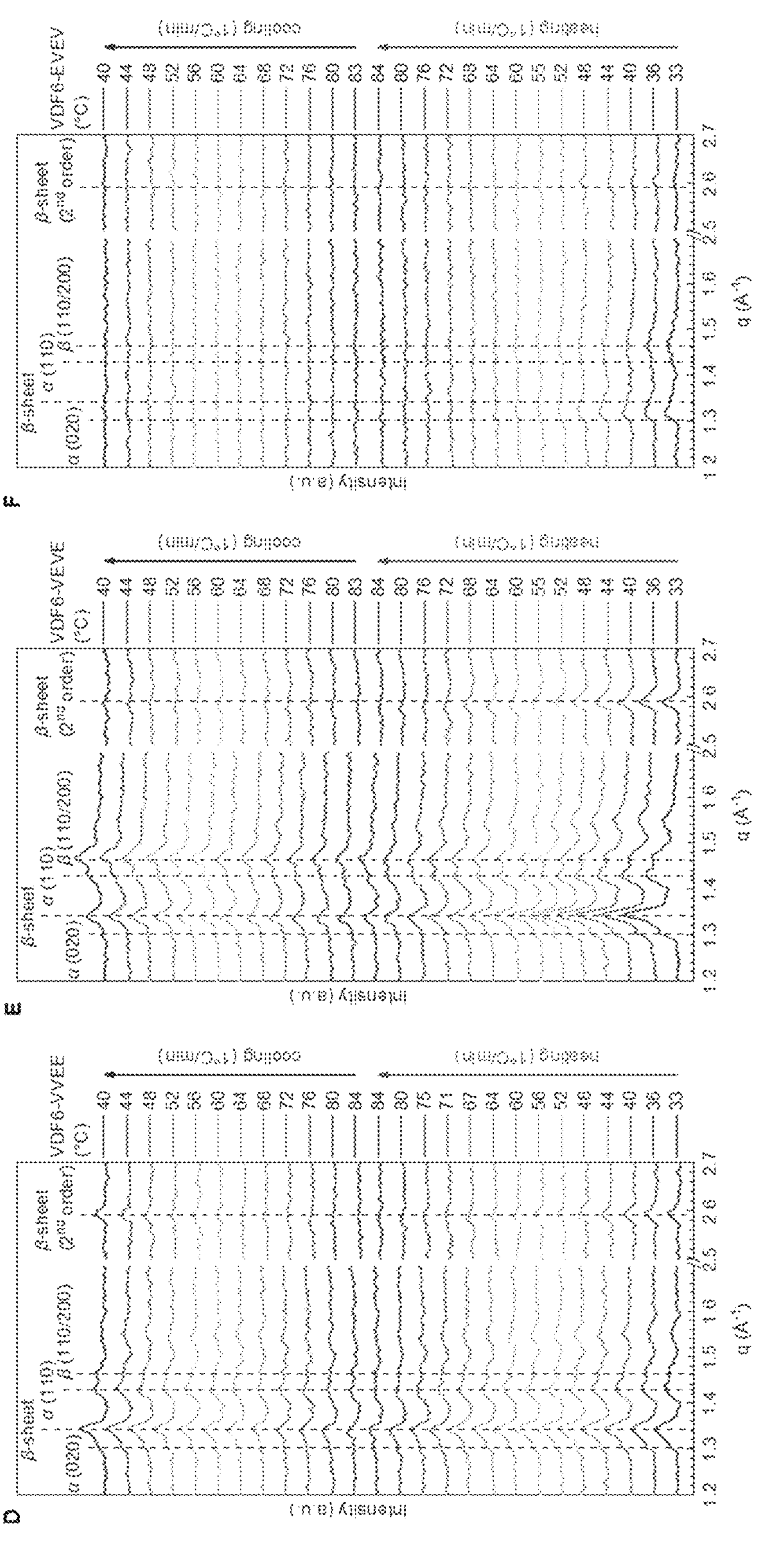
Figures 3G, 3H, 3I:
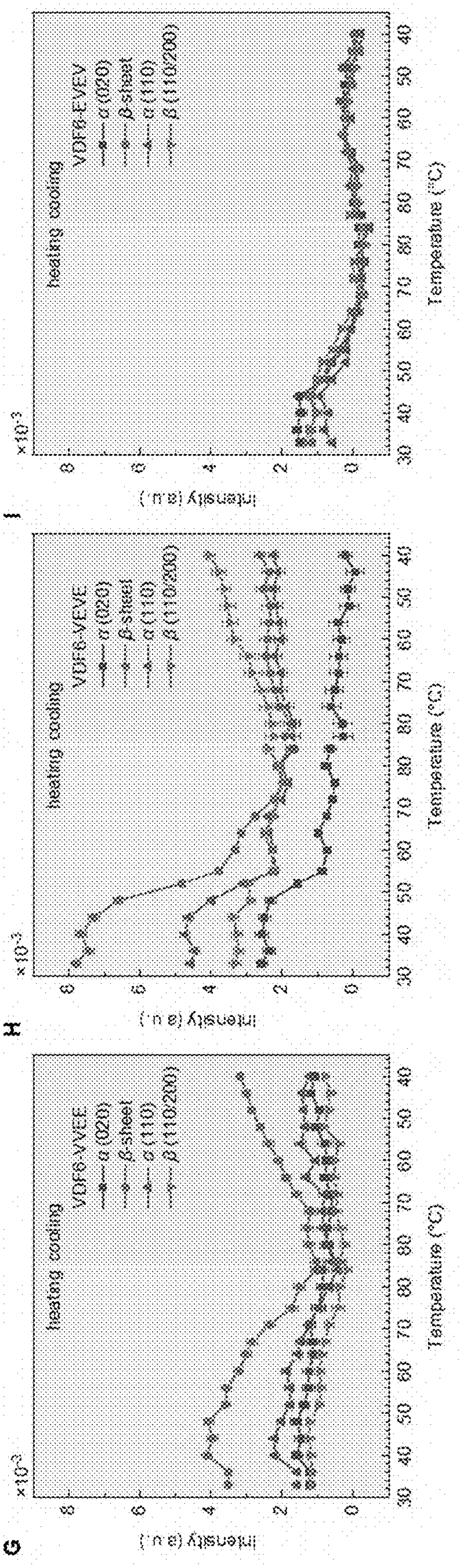
Figures 18A, 18B, 18C:
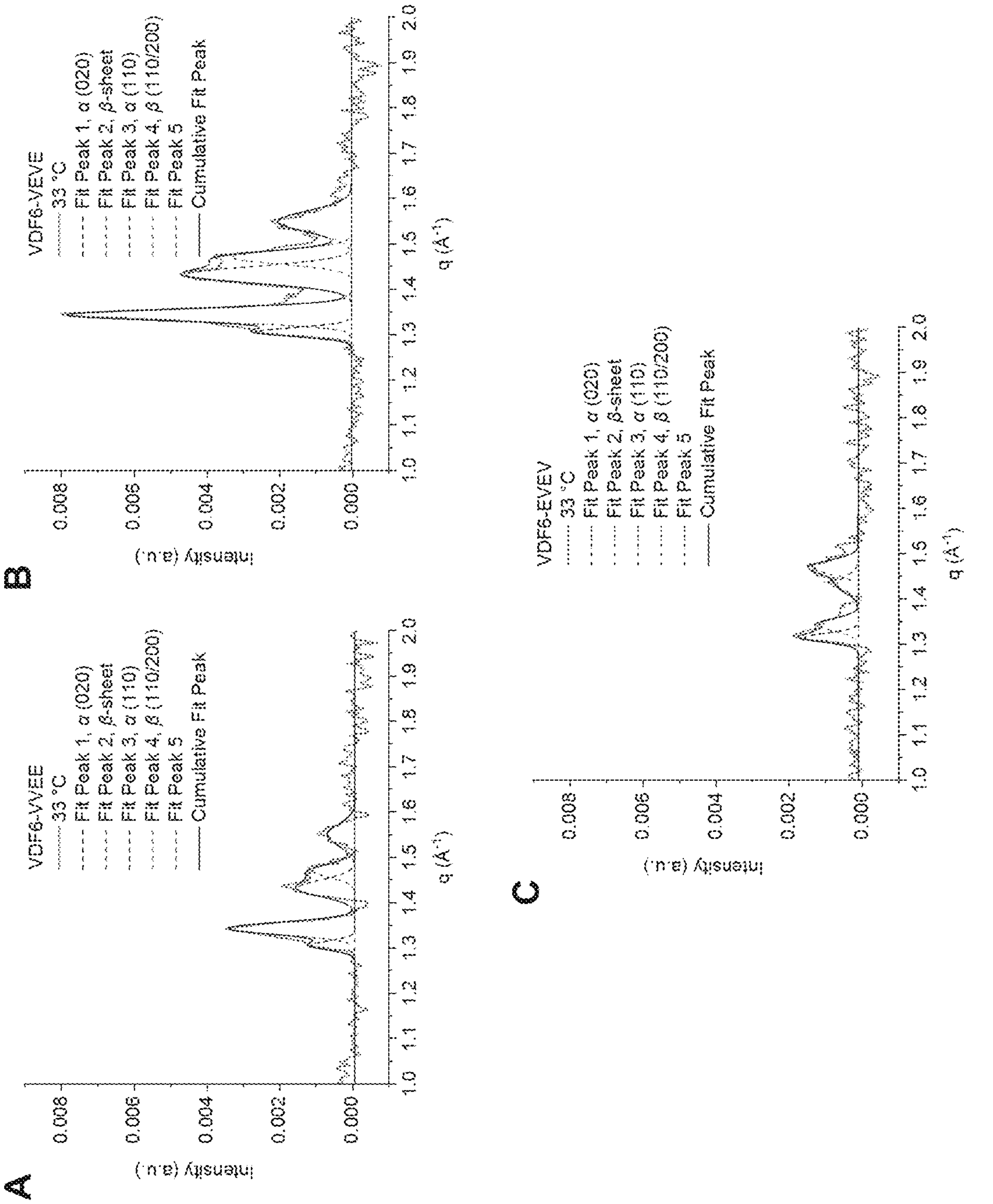
FIG. 18A, FIG. 18B, and FIG. 18C show Gauss fitting of the scattering peaks in VT-WAXS with fixed peak position corresponding to α (020), α (110), β (110/200) VDF and hydrogen bonding spacing in β-sheets and full width at half-maximum (FWHM) determined by the initial WAXS curves at 33° C. for the VDF6-PAs. The peak center and resulting FWHM values are shown in table s1.
Figures 19A, 19B, 19C:
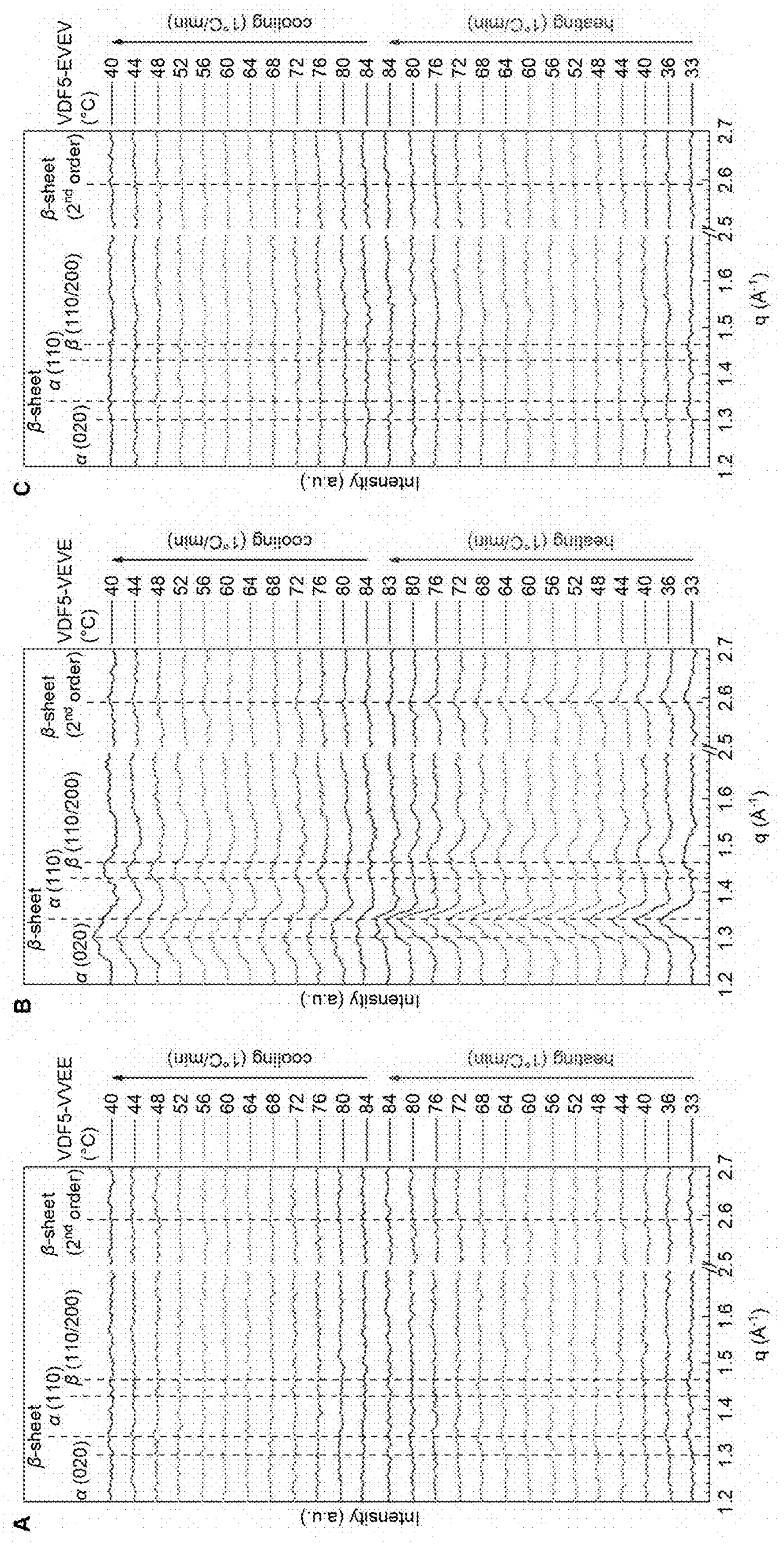
FIGS. 19A-19C show VT-WAXS patterns of 20 mM annealed (FIG. 19A) VDF5-VVEE (SEQ ID NO: 1), (FIG. 19B) VDF5-VEVE (SEQ ID NO: 2) and (FIG. 19C) VDF5-EVEV (SEQ ID NO: 3) with the peak positions indicated: 020 plane at q=1.30 $Å^{-1}$ and 110/200 plane at q=1.43 $Å^{-1}$ for α-phase VDF, 110/200 plane at q=1.46 $Å^{-1}$ for β-phase VDF, q=1.34 $Å^{-1}$ for hydrogen bond spacing of β-sheet peptide and its second order reflection at q=2.59 $Å^{-1}$. The scattering intensities were offset vertically for clarity.

Variable-temperature wide-angle X-ray scattering (VT-WAXS) was performed on the pre-annealed solutions to further investigate the crystallization mechanisms and thermodynamic behavior of the VDF-PAs. Initial WAXS curves at room temperature show the highest crystallinity of VDF in VDF6-VEVE (SEQ ID NO: 2) (FIG. 3E), and VDF6-EVEV (SEQ ID NO: 3) shows the lowest crystallinity with a similar amount of α- and β-phase VDF (FIG. 3F). The β-sheet peaks at q=1.34 $Å^{-1}$ in VDF6-VVEE (SEQ ID NO: 1) and VDF6-VEVE (SEQ ID NO: 2) always exist during the heating-cooling cycle, consistent with their high melting point (>84° C.) as demonstrated by the DSC curves. The peaks of β-sheet and VDF crystals in VDF6-EVEV (SEQ ID NO: 3) gradually vanish around 60° C. and don't recover after cooling which agrees with the DSC results and explains the decreased FTIR peak intensity of α- and β-phase VDF of the samples dried from the solution that was annealed above 80° C. (FIG. 17). Different from the WAXS patterns on 10 mM annealed samples (FIG. 2E), a subpeak at q=1.43 $Å^{-1}$, corresponding to a (110) VDF crystals, is observed in the 20 mM annealed VDF6-VEVE (SEQ ID NO: 2) sample (FIG. 3E). The scattering peaks in VT-WAXS curves were fitted by Gauss function with fixed peak position and full width at half-maximum (FWHM) (FIG. 18) to provide a quantitative analysis of crystal phase composition as shown in FIG. 3, G to I. Interestingly, VDF6-VEVE (SEQ ID NO: 2) shows a decrease of this α-phase VDF peak and an increase of β-phase VDF after the heating-cooling cycle indicating the phase transition of the remanent a phase to the dominant β phase in the VDF regions (FIG. 3H). The high melting temperature (>100° C.) of VEVE β-sheets and increased crystal size of VDF6-VEVE (SEQ ID NO: 2) assemblies formed in high concentration (FIG. 7) enable the growth of β-phase crystal domains in VDF regions during repeated annealing processes. For the VDF5-PAs, only the VDF5-VEVE (SEQ ID NO: 2) shows obvious scattering peaks of β-sheet and VDF crystals and no obvious recovery fast cooling (FIG. 19), consistent with the absorbance intensities in FTIR (FIG. 3, G to I) and its low melting point in DSC. These results demonstrate the favored crystallization of VDF with VEVE (SEQ ID NO: 2) peptide.

Ferroelectricity of the VDF-PA Assemblies

Figures 4A, 4B, 4C, 4D, 4E, 4F:
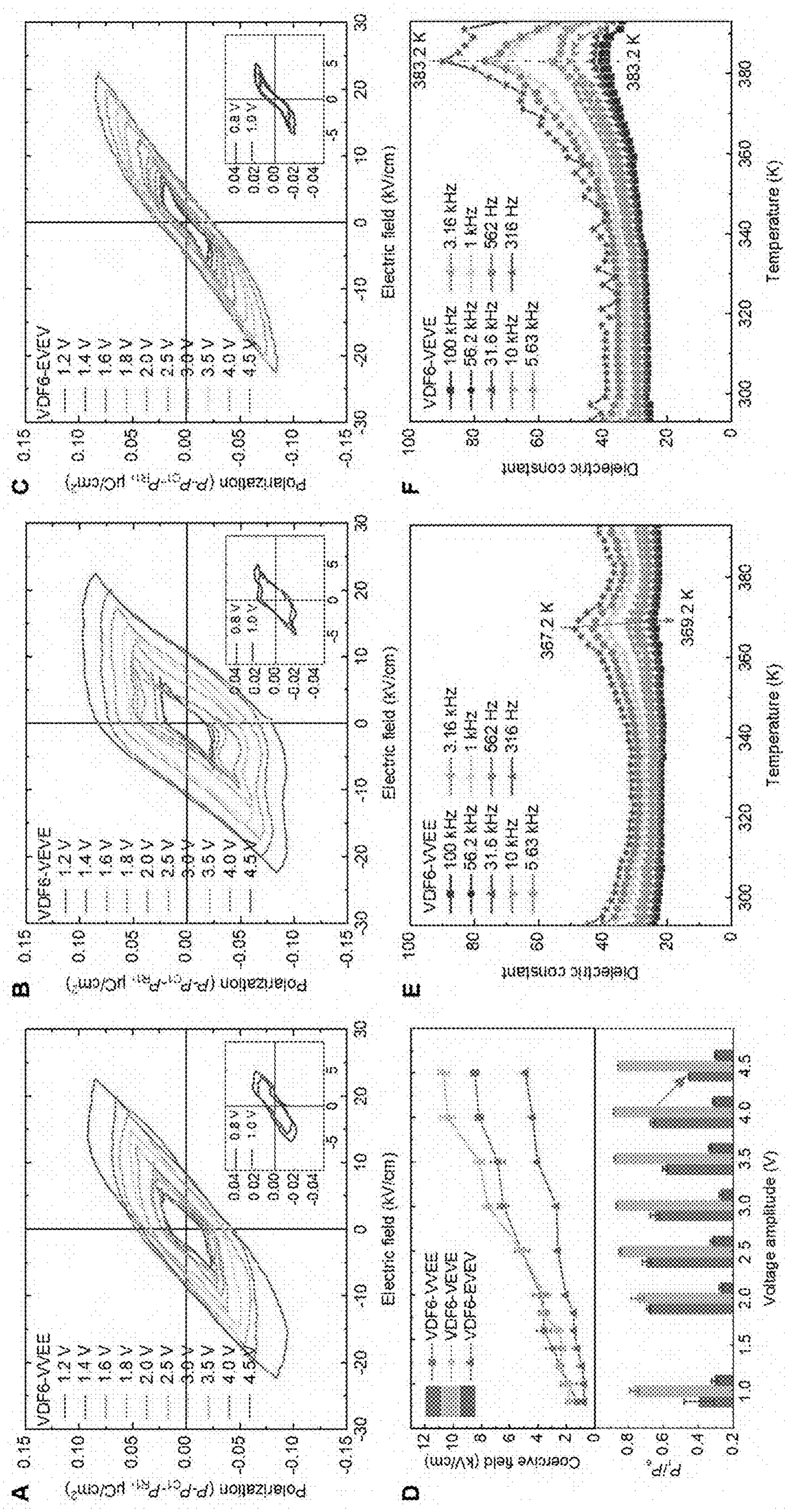
FIGS. 4A-4I show ferroelectricity of the VDF-PA assemblies.
Figures 20A, 20B, 20C, 20D, 20E:
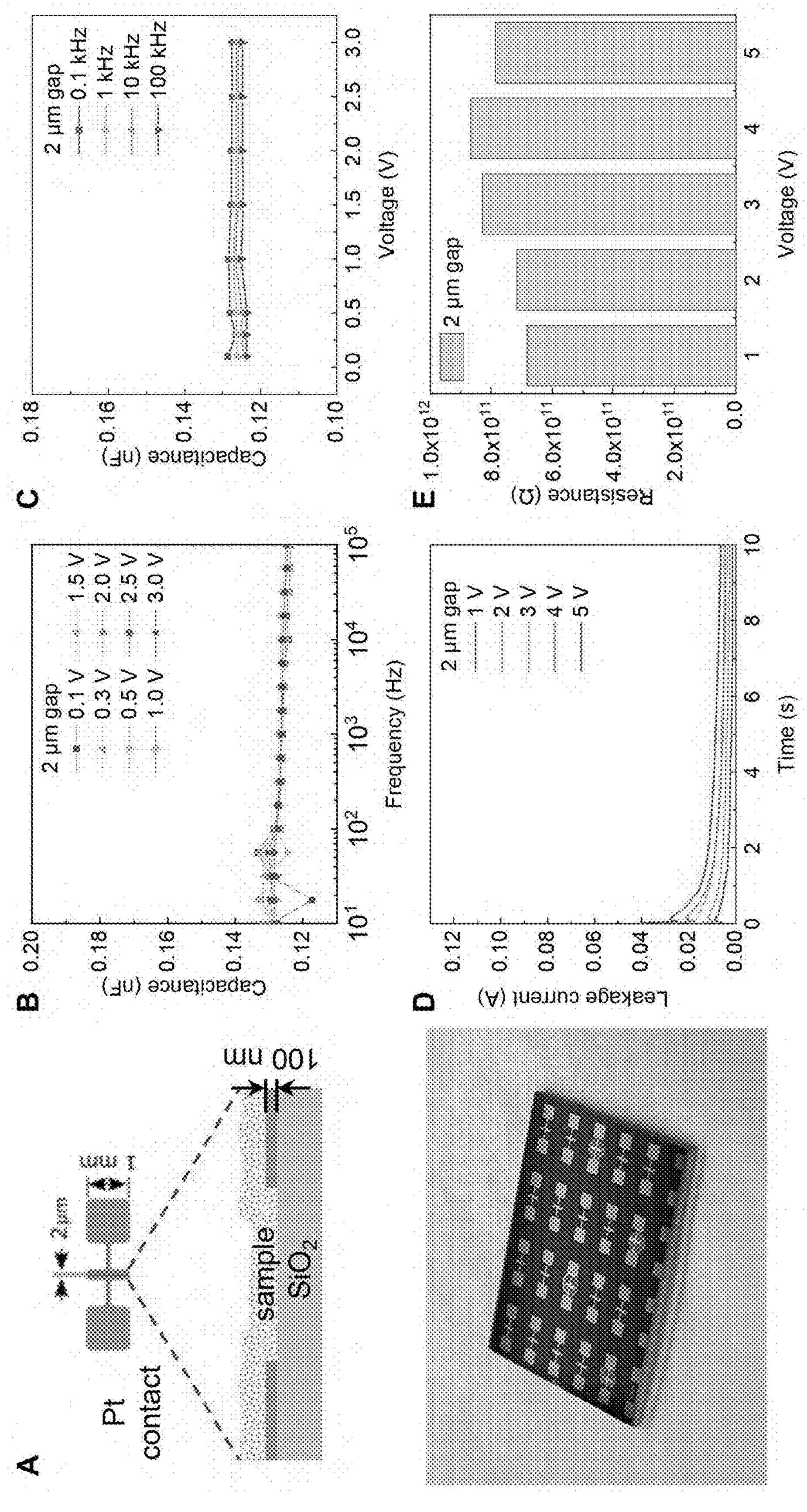
FIGS. 20A-20E show silicon testing chip with 2 μm gaps.
Figures 21A, 21B, 21C, 21D, 21E, 21F:
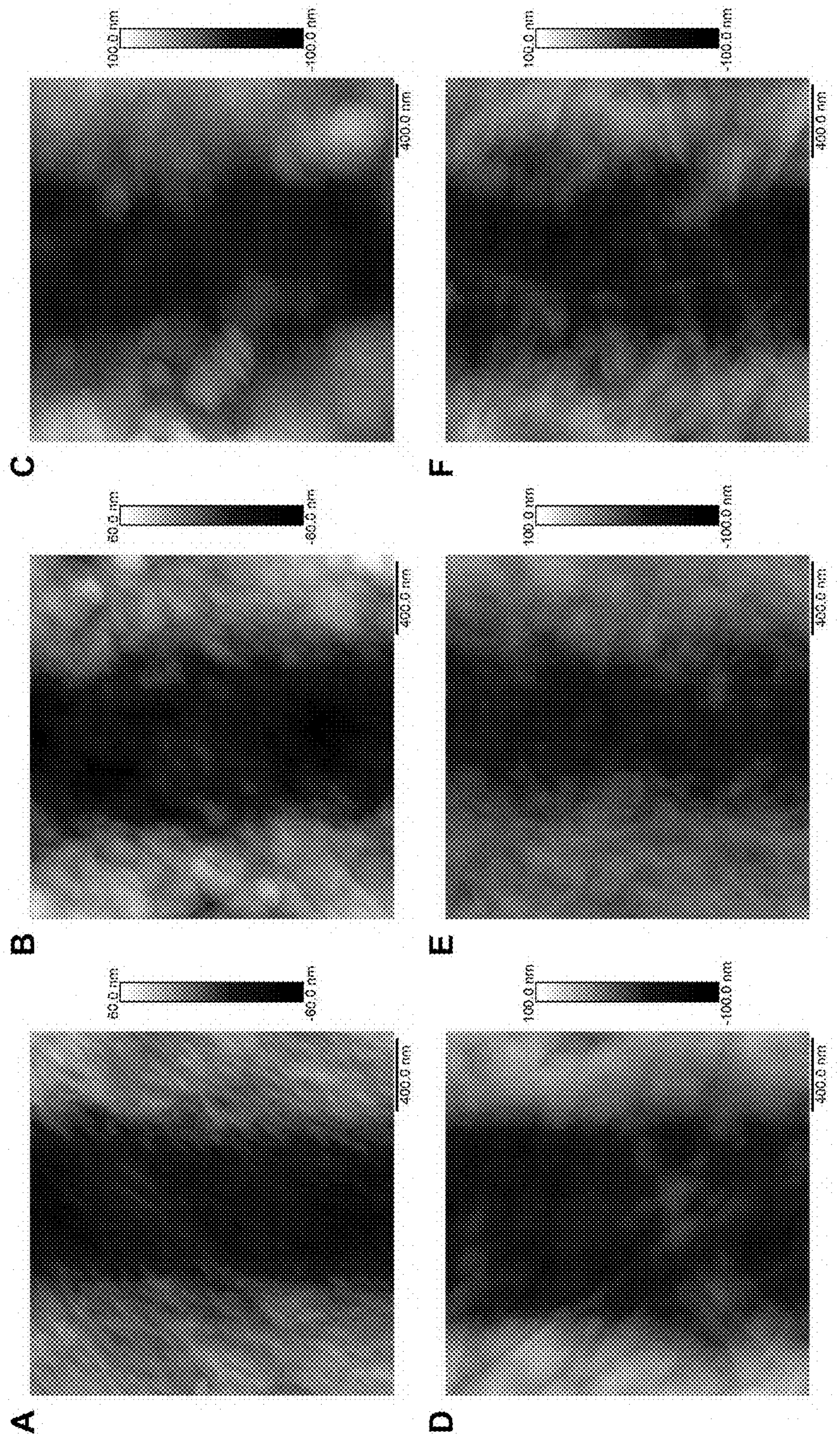
FIGS. 21A-21F show surface AFM morphology of (FIG. 21A) VDF6-VVEE (SEQ ID NO: 1), (FIG. 21B) VDF6-VEVE (SEQ ID NO: 2), (FIG. 21C) VDF6-EVEV (SEQ ID NO: 3), (FIG. 21D) C16-VVEE (SEQ ID NO: 1), (FIG. 21E) C16-VEVE (SEQ ID NO: 2) and (FIG. 21F) C16-EVEV (SEQ ID NO: 3) films on the testing substrates with bottom Platinum electrodes.
Figures 22A, 22B, 22C, 22D, 22E, 22F, 22G, 22H, 22I, 22J, 22K, 22L:
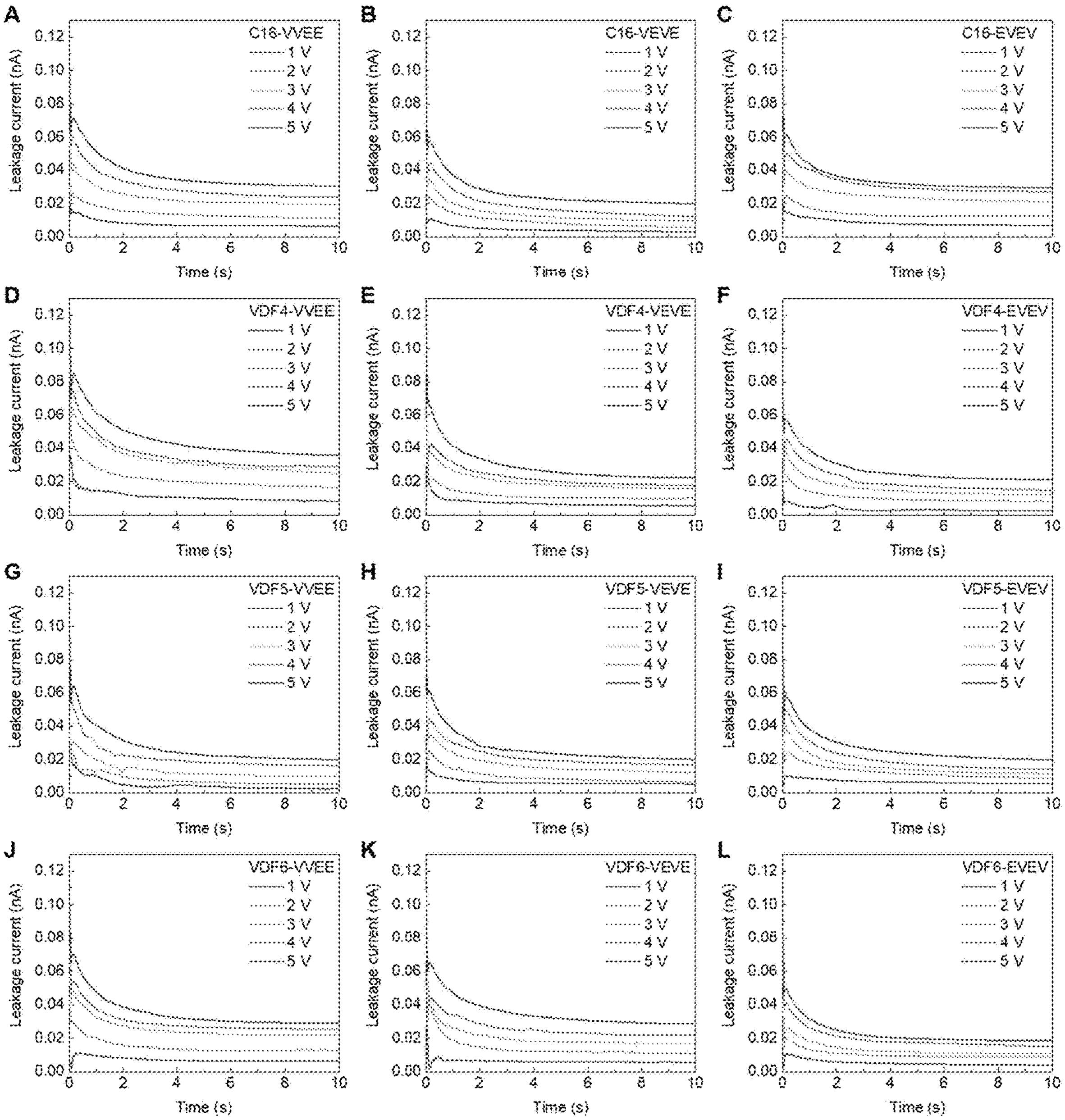
FIGS. 22A-22L show Leakage current of (FIG. 22A) C16-VVEE (SEQ ID NO: 1), (FIG. 22B) C16-VEVE (SEQ ID NO: 2), (FIG. 22C) C16-EVEV (SEQ ID NO: 3), (FIG. 22D) C16-VVEE (SEQ ID NO: 1), (FIG. 22E) VDF4-VEVE (SEQ ID NO: 2), (FIG. 22F) VDF4-EVEV (SEQ ID NO: 3), (FIG. 22G) VDF5-VVEE (SEQ ID NO: 1), (FIG. 22H) VDF5-VEVE (SEQ ID NO: 2), (FIG. 22I) VDF5-EVEV (SEQ ID NO: 3), (FIG. 22J) VDF6-VVEE (SEQ ID NO: 1), (FIG. 22K) VDF6-VEVE (SEQ ID NO: 2) and (FIG. 22L) VDF6-EVEV (SEQ ID NO: 3) samples as a function of time under different DC voltages. The measured current curves show no polarization process after 10 s thus the resistance (R1) values can be calculated.
Figures 23A, 23B, 23C, 23D, 23E, 23F, 23G, 23H, 23I, 23J, 23K, 23L:
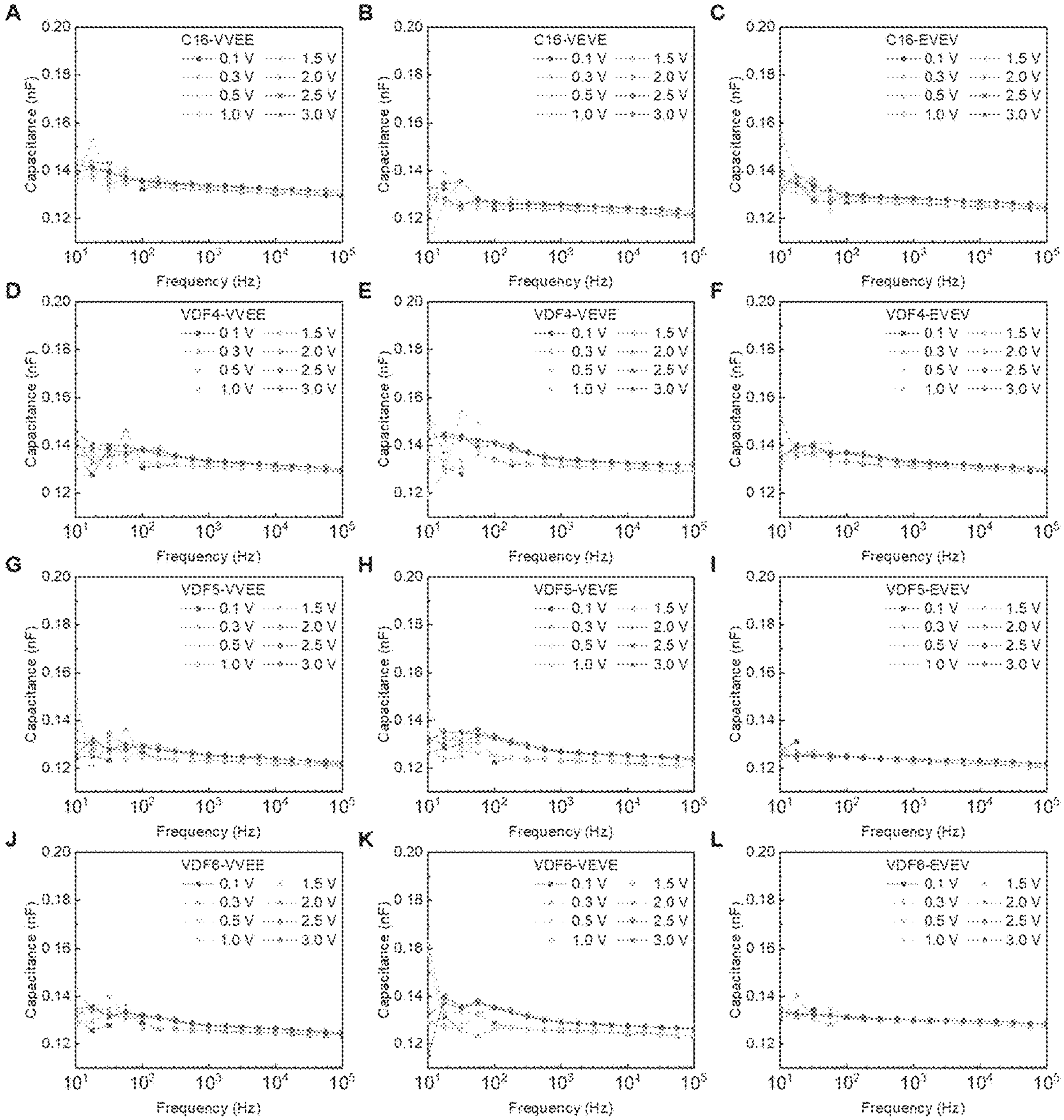
FIGS. 23A-23L show frequency domain capacitance of (FIG. 23A) C16-VVEE (SEQ ID NO: 1), (FIG. 23B) C16-VEVE (SEQ ID NO: 2), (FIG. 23C) C16-EVEV (SEQ ID NO: 3), (FIG. 23D) C16-VVEE (SEQ ID NO: 1), (FIG. 23E) VDF4-VEVE (SEQ ID NO: 2), (FIG. 23F) VDF4-EVEV (SEQ ID NO: 3), (FIG. 23G) VDF5-VVEE (SEQ ID NO: 1), (FIG. 23H) VDF5-VEVE (SEQ ID NO: 2), (FIG. 23I) VDF5-EVEV (SEQ ID NO: 3), (FIG. 23J) VDF6-VVEE (SEQ ID NO: 1), (FIG. 23K) VDF6-VEVE (SEQ ID NO: 2) and (FIG. 23L) VDF6-EVEV (SEQ ID NO: 3) samples under different amplitudes of AC voltage. The capacitance values are mainly contributed by the air gap and substrate in parallel with the PA coatings, as shown in FIG. 20A, which contribute linear polarization in ferroelectricity tests.
Figures 24A, 24B, 24C, 24D:
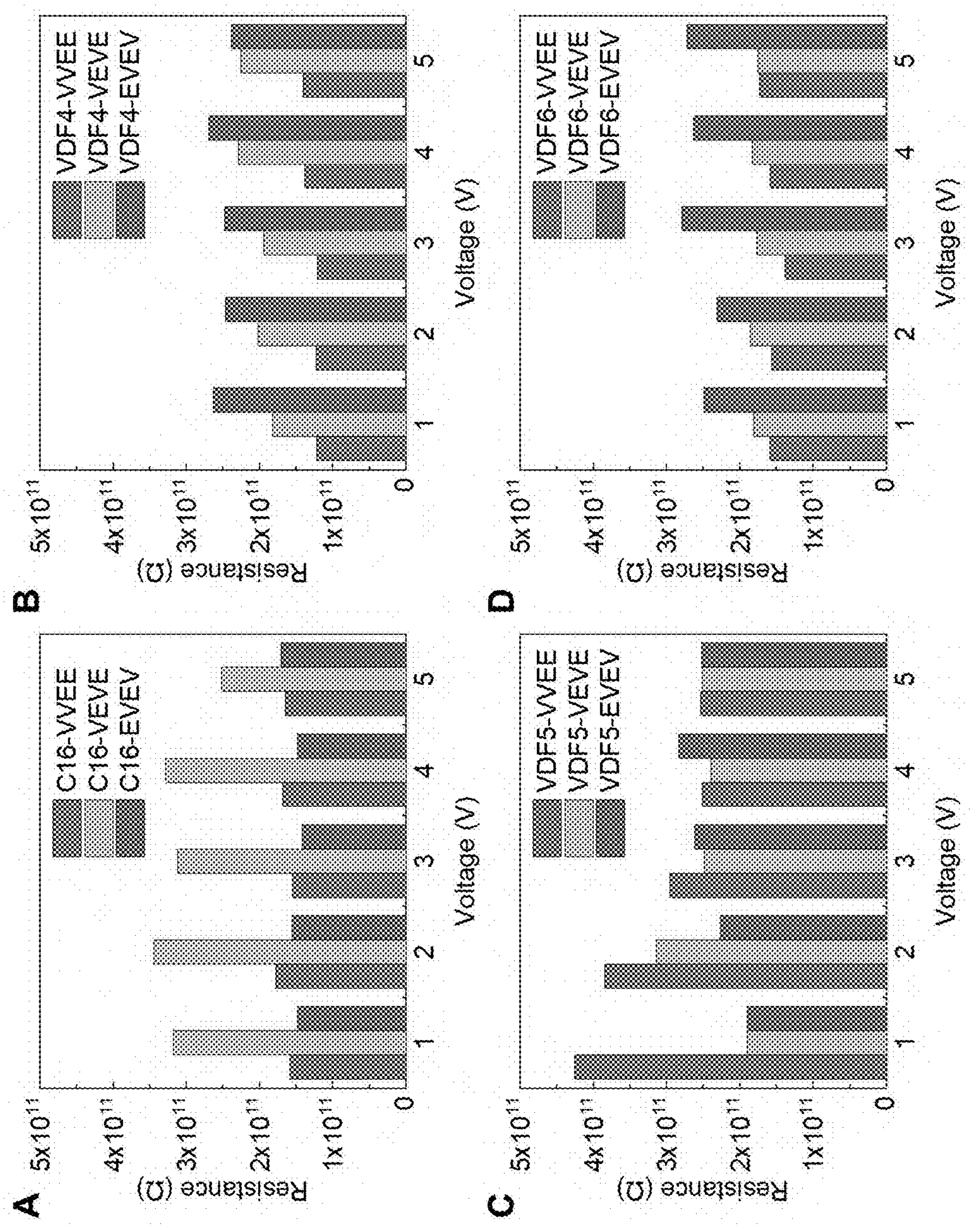
FIGS. 24A-24D show resistance of (FIG. 24A) C16-PA, (FIG. 24B) VDF4-PA, (FIG. 24C) VDF5-PA and (FIG. 24D) VDF6-PA samples according to the leakage current measured under different voltage as shown in FIG. 22.
Figures 25A, 25B, 25C, 25D, 25E, 25F:
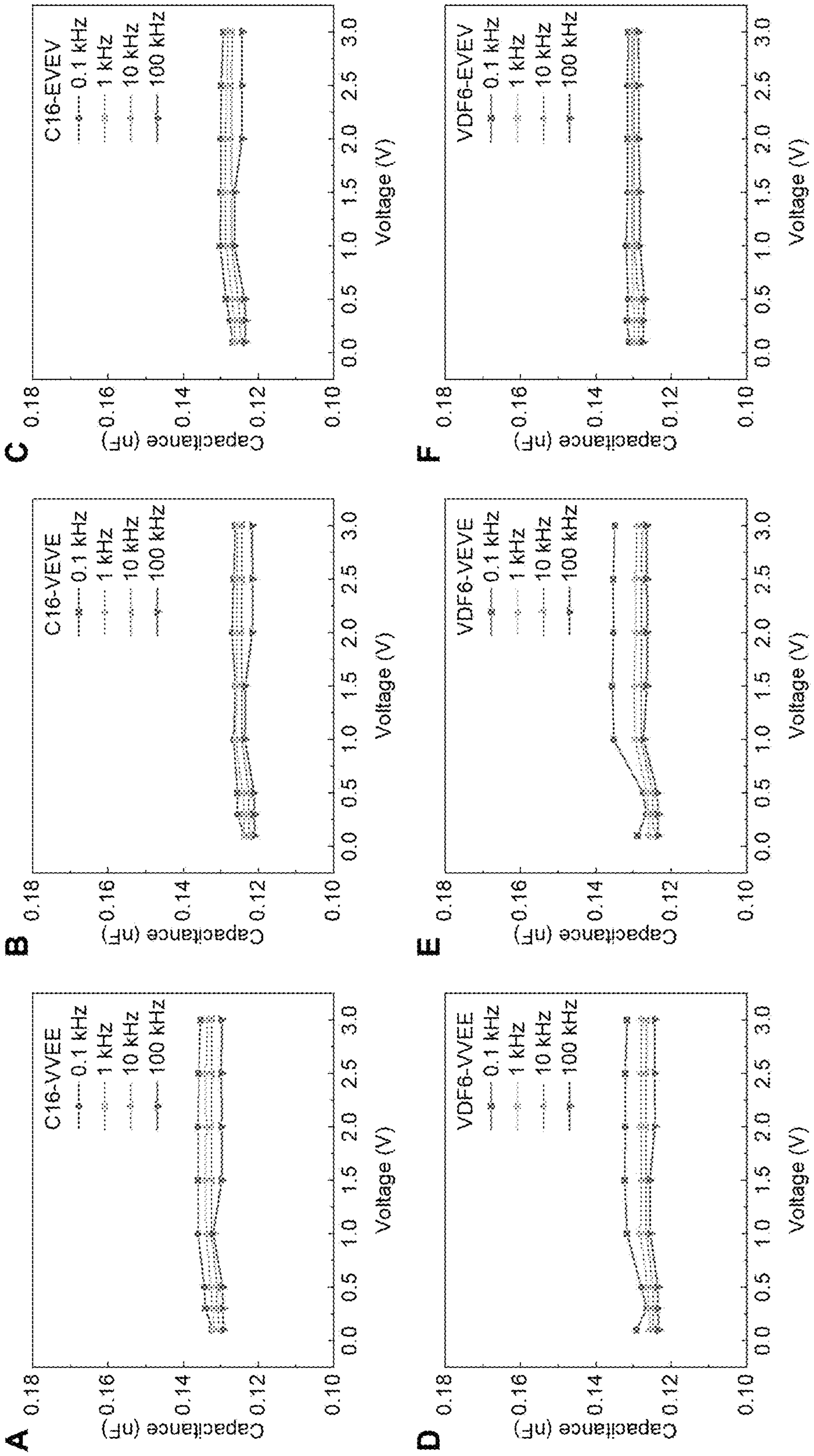
FIGS. 25A-25F show Capacitance of (FIG. 25A) C16-VVEE (SEQ ID NO: 1), (FIG. 25B) C16-VEVE (SEQ ID NO: 2), (FIG. 25C) C16-EVEV (SEQ ID NO: 3), (FIG. 25D) VDF6-VVEE (SEQ ID NO: 1), (FIG. 25E) VDF6-VEVE (SEQ ID NO: 2) and (FIG. 25F) VDF6-EVEV (SEQ ID NO: 3) samples under different frequencies as a function of voltage amplitude. Data collected from FIG. 23.
Figure 26:
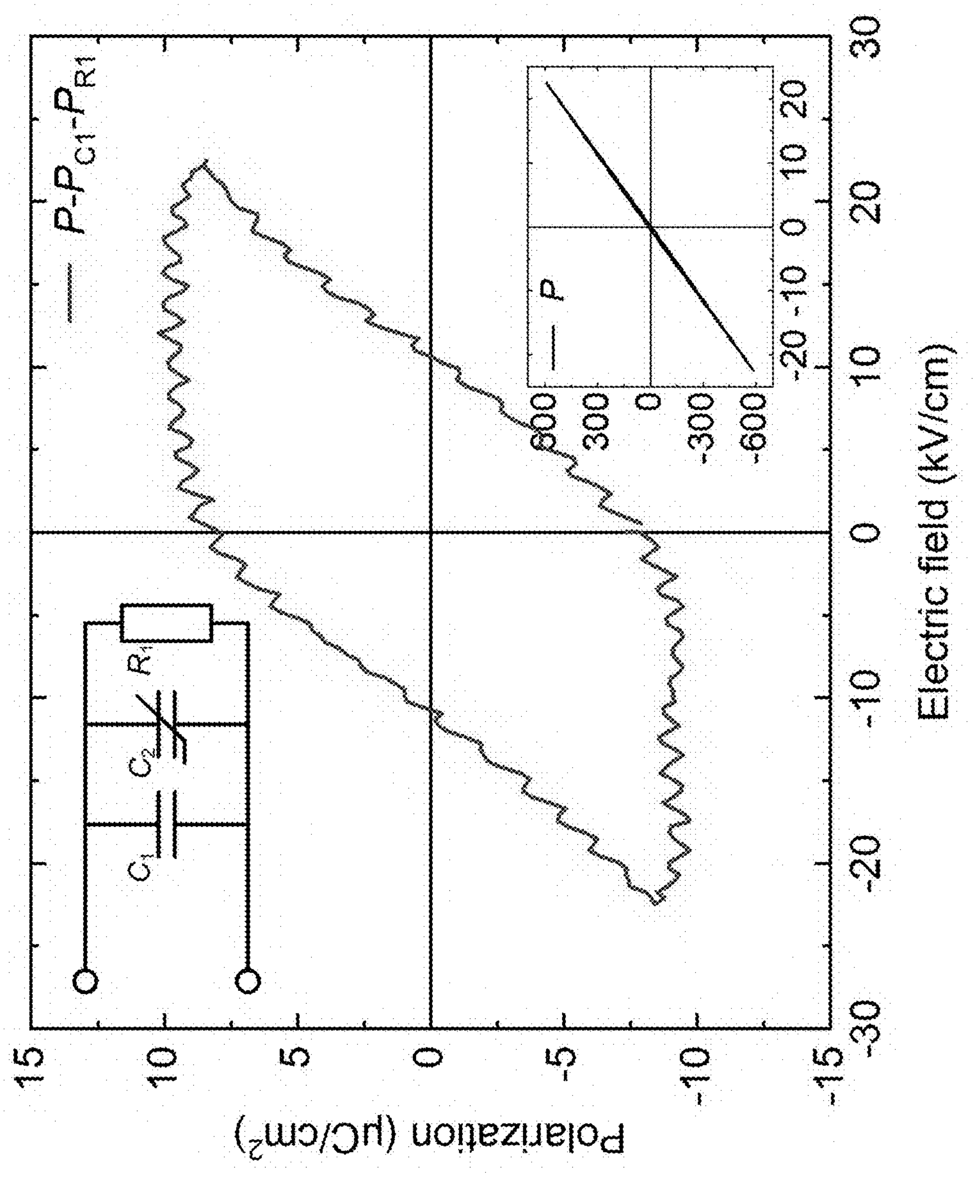
FIG. 26 shows P-E loop processing by subtracting the contribution of resistive loss $P_{R1}$ and linear polarization $P_{C1}$ of the samples from the original data. The top left inset schematic of the equivalent circuit shows the composition of measured polarization including a linear capacitor C1 in parallel with a non-linear capacitor C2 (hysteretic polarization) and a resistor R1. The bottom right inset show the original measured polarization P.
Figure 27:
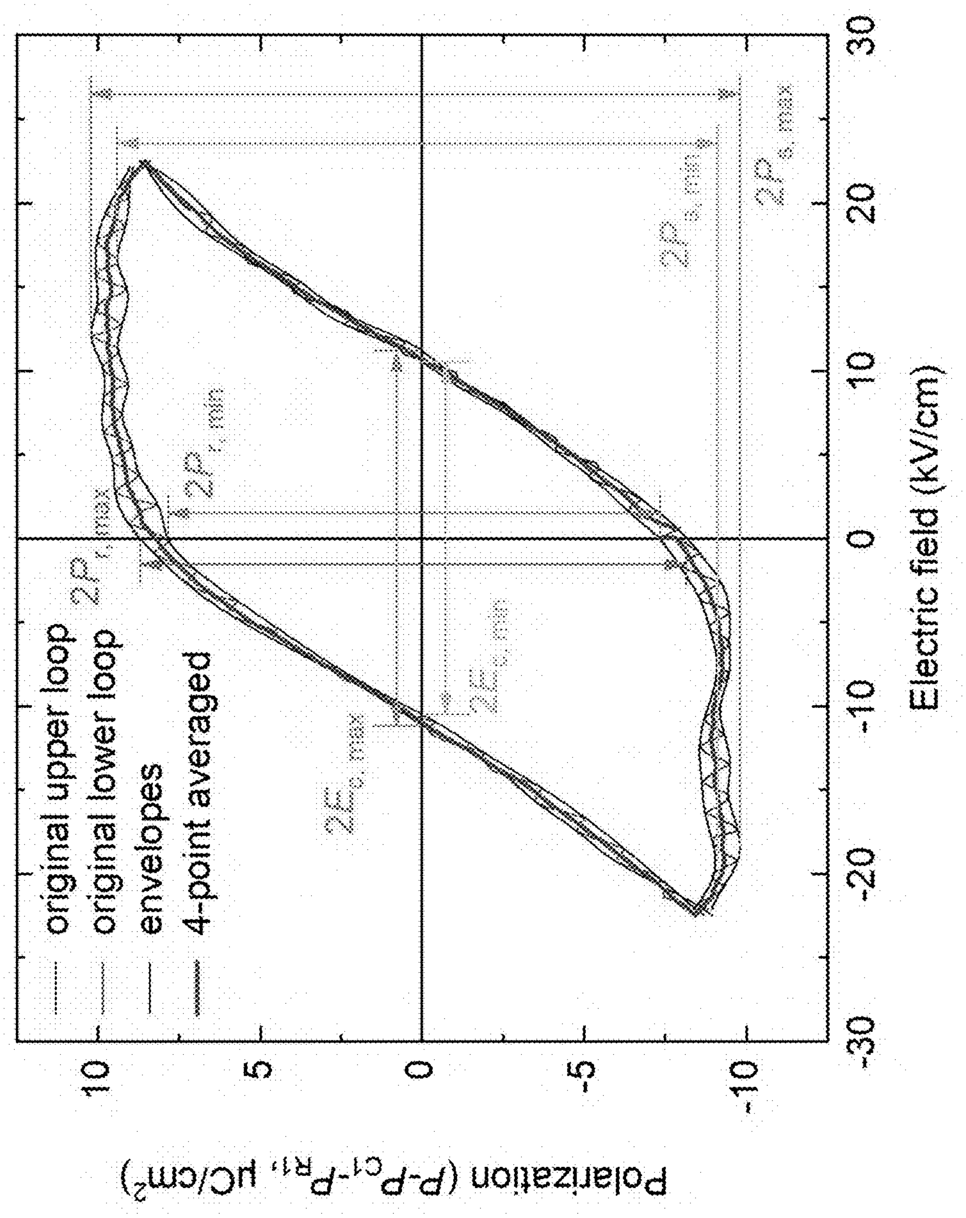
FIG. 27 shows the ferroelectric P-E loop of VDF6-VEVE (SEQ ID NO: 2). The upper and lower envelope curves obtained by applying a local maximum method combined with a cubic spline interpolation in Origin software determine the maximum and minimum values of coercive field $E_{c,max}$ and $E_{c,min}$, remanent polarization $P_{r,max}$ and $P_{r,min}$, saturation polarization $P_{s,max}$ and $P_{s,min}$. The error bar of $E_c$, $P_r$ and $P_s$ are obtained by (max-min)/2. Considering that the noise has a consistent trend of influence on $P_r$ and $P_s$, error bar of the ratio $P_r/P_s$ are obtained by $|P_{r,max}/P_{s,max}-P_{r,min}/$ $P_{s,min}$1/2. The 4-point averaging is also performed in Origin software to eliminate the high frequency noise.
Figures 28A, 28B, 28C:
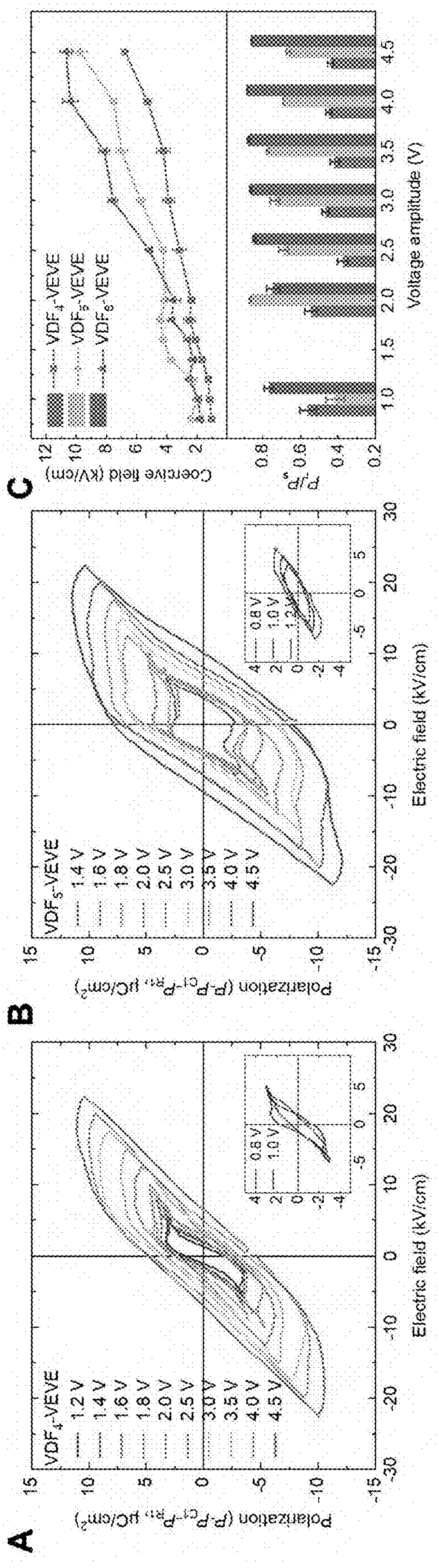
FIGS. 28A-28C show ferroelectricity of VDF-VEVE (SEQ ID NO: 2) PAs. P-E loops of (FIG. 28A) VDF4-VEVE (SEQ ID NO: 2) and (FIG. 28B) VDF5-VEVE (SEQ ID NO: 2) under different applied maximum voltages. The insets show the cigar-shaped lossy loops under low voltages indicating inactivation of the ferroelectric domains.
Figures 29A, 29B, 29C, 29D, 29E:
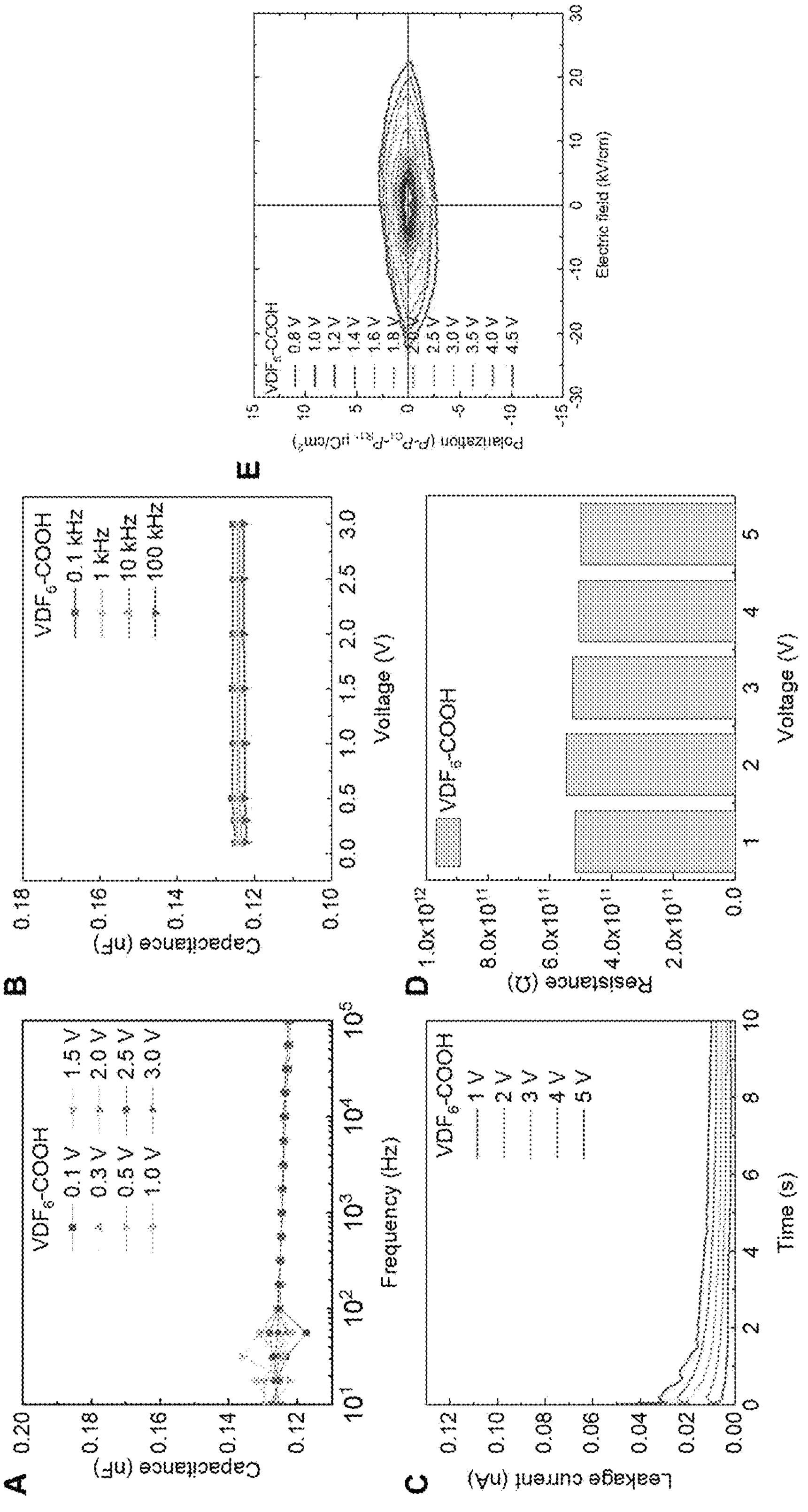
FIGS. 29A-29E show electrical properties of VDF6-COOH samples.
Figures 30A, 30B, 30C:
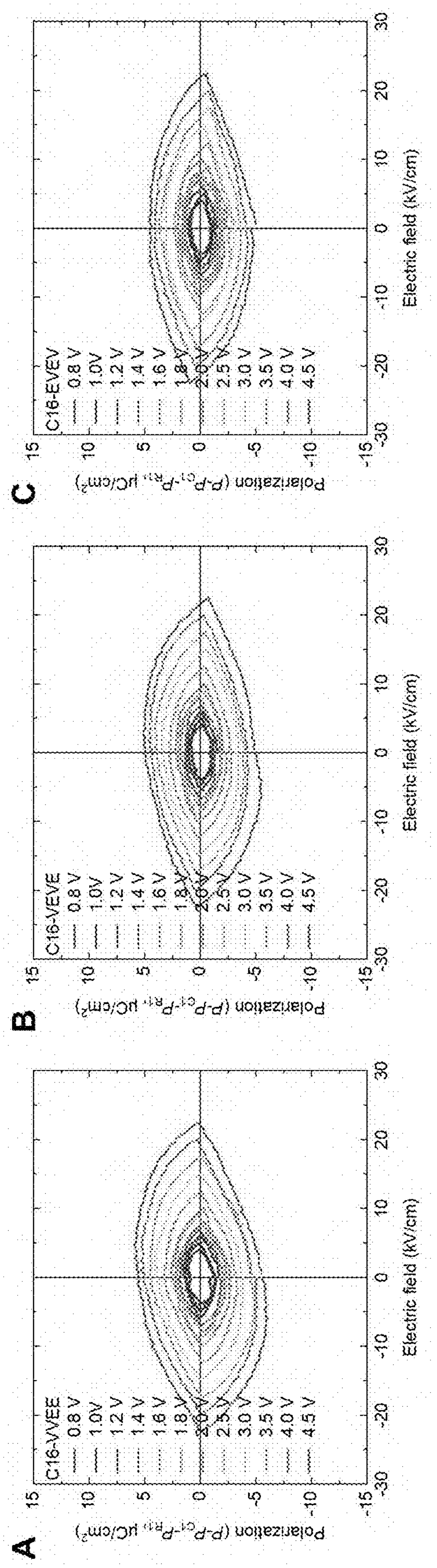
FIGS. 30A-30C show P-E loops of (FIG. 30A) C16-VVEE (SEQ ID NO: 1), (FIG. 30B) C16-VEVE (SEQ ID NO: 2) and (FIG. 30C) C16-EVEV (SEQ ID NO: 3) assembly films under different applied maximum voltages.
Figures 31A, 31B:
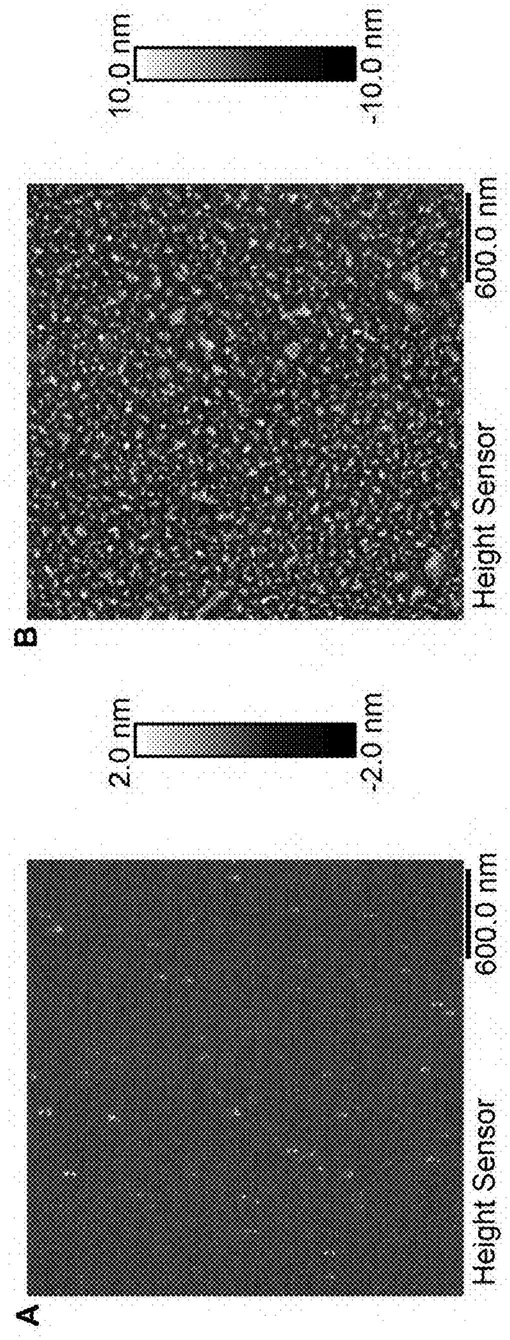
FIGS. 31A-31B show AFM images of VDF6-COOH in (FIG. 31A) liquid and (FIG. 31B) dry state samples prepared from 10 mM annealed solution.

The preferential β-phase VDF formation in the VDF-PAs led to further investigation on the ferroelectric properties of these materials. To measure the in-plane electrical properties of the PA ribbons, dry-state thin films of the VDF-PA assemblies were prepared by casting the 20 mM annealed PA solutions on a $SiO_2$ insulating substrate with photolithographically patterned platinum electrodes (FIG. 20). AFM images of the samples' surface show randomly oriented PA ribbons across the 2 μm gap between the electrodes (FIG. 21). Leakage current measurements of the samples show high resistance $R_1$ above $10^{11}$ Ω (FIG. 24), which is favorable for high-performance ferroelectrics. Frequency domain tests show an abrupt increase of capacitance in VDF6-VVEE (SEQ ID NO: 1) and VDF6-VEVE (SEQ ID NO: 2) samples at low frequency as the voltage amplitude increases from 0.5 V to 1.0 V (FIG. 25), suggesting activation of ferroelectric dipoles above the coercive fields. The linear capacitance $C_1$ of the samples are obtained from the high-frequency measurements to exclude the contribution of ferroelectric polarization. Polarization-electric field (P-E) loops of the samples were obtained by subtracting the contribution of resistive loss $P_{R1}$ and linear polarization $P_{C1}$ of the samples from the original data (FIG. 26 and Table S2). As shown in FIG. 4A, non-axisymmetric ferroelectric hysteresis is observed in VDF6-VVEE (SEQ ID NO: 1) when the maximum applied voltage exceeds 1 V. As the maximum electric field exceeds 20 kV/cm, the saturation polarization $P_s$ of VDF6-VVEE (SEQ ID NO: 1) increases while the remanent polarization $P_r$ remains unchanged, indicating saturated ferroelectric domain reorientation. The loop shows a little decline of polarization as the applied field approaches the maximum, this may be attributed to increased conduction loss under a high field. Through the entire range of tested voltage, VDF6-VEVE (SEQ ID NO: 2) exhibits typical ferroelectric hysteresis with high coercive filed and remanent polarization close to the saturation, and no trend of increased conduction loss is observed (FIG. 4B). To provide a quantitative comparison of ferroelectricity, the ability of retention of polarization strength evaluated by the ratio $P_r/P_s$ and coercive field of the VDF6-PA assembly films are summarized in FIG. 4D. The trend of ferroelectricity VDF6-VEVE (SEQ ID NO: 2)>VDF6-VVEE (SEQ ID NO: 1)>VDF6-EVEV (SEQ ID NO: 3) is consistent with conjectures based on the morphological and crystal structure characterizations that larger ribbon structures and higher β-phase VDF content induced by peptide β-sheets enable more coupled ferroelectric domains and stronger ferroelectricity in PA assemblies. This crystallinity and crystal size effect is also confirmed by the increased ferroelectricity of the VEVE PAs as the VDF tail length increases (FIG. 28). The VDF6-COOH sample, although forming β-phase VDF in dry-state as demonstrated by FTIR, shows cigar-shaped P-E loops (FIG. 29), indicating no ferroelectric polarization but typical lossy dielectrics behavior (*J. Phys. Condens. Matter.* 20, 021001 (2008)) as is also observed in the C16-PA assembly films (FIG. 30). Because of the absence of long-range ordered structures in VDF6-COOH (FIG. 31), the β-phase VDF crystallites are too small to couple with each other and form ferroelectric domains at room temperature.

Figures 4G, 4H, 4I:
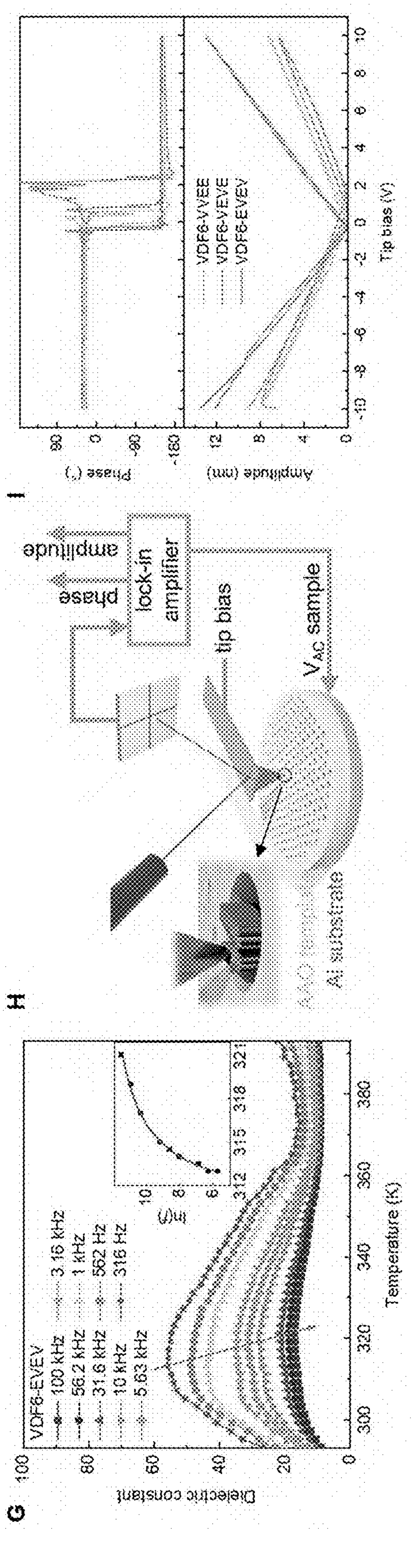
Figures 32A, 32B, 32C, 32D, 32E, 32F:
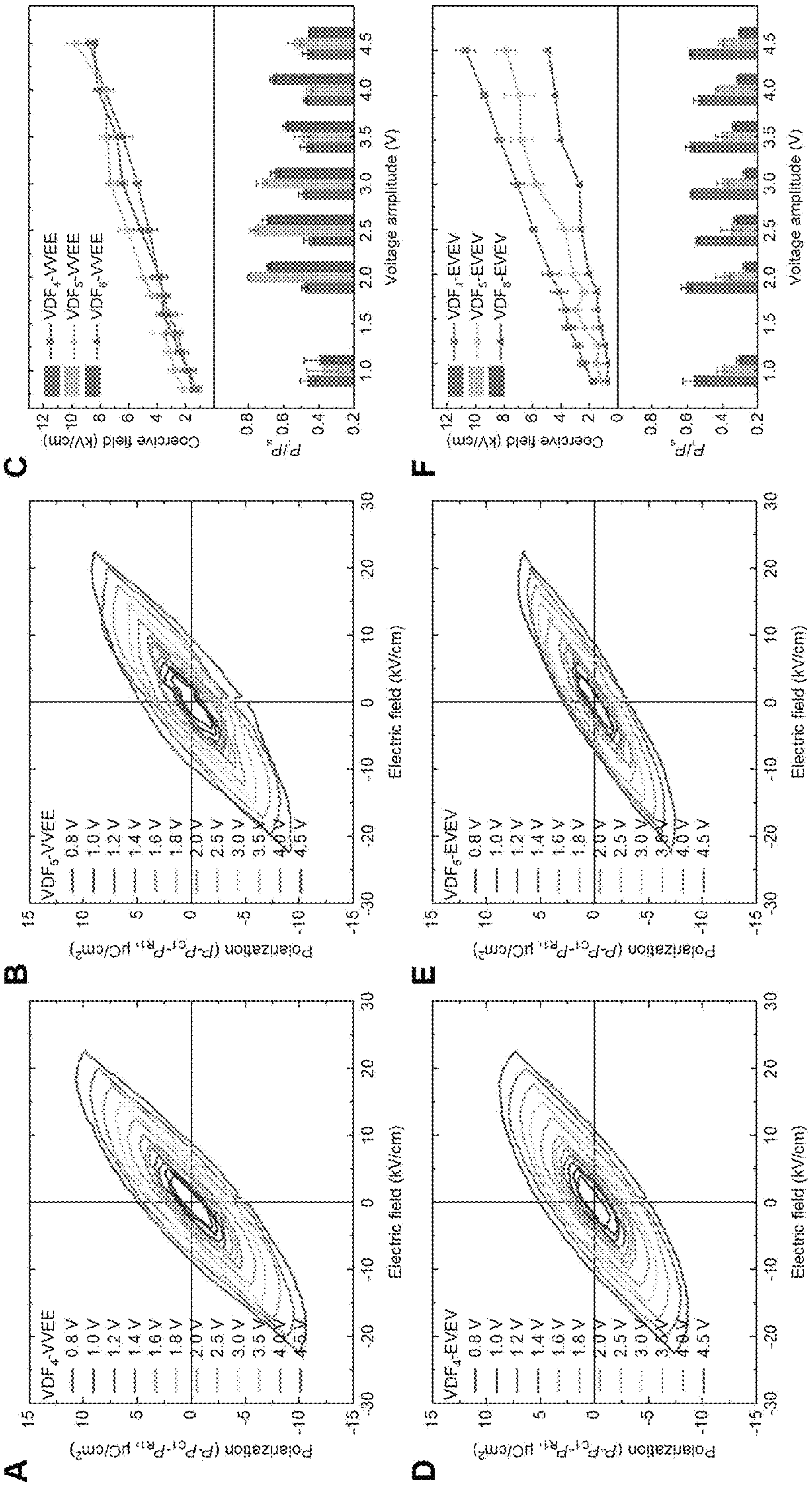
FIGS. 32A-32F show ferroclectricity of VDF PAs. P-E loops of (FIG. 32A) VDF4-VVEE (SEQ ID NO: 1) and (FIG. 32B) VDF5-VVEE (SEQ ID NO: 1) under different applied maximum voltages.
Figures 34A, 34B, 34C, 34D, 34E, 34F, 34G, 34H, 34I:
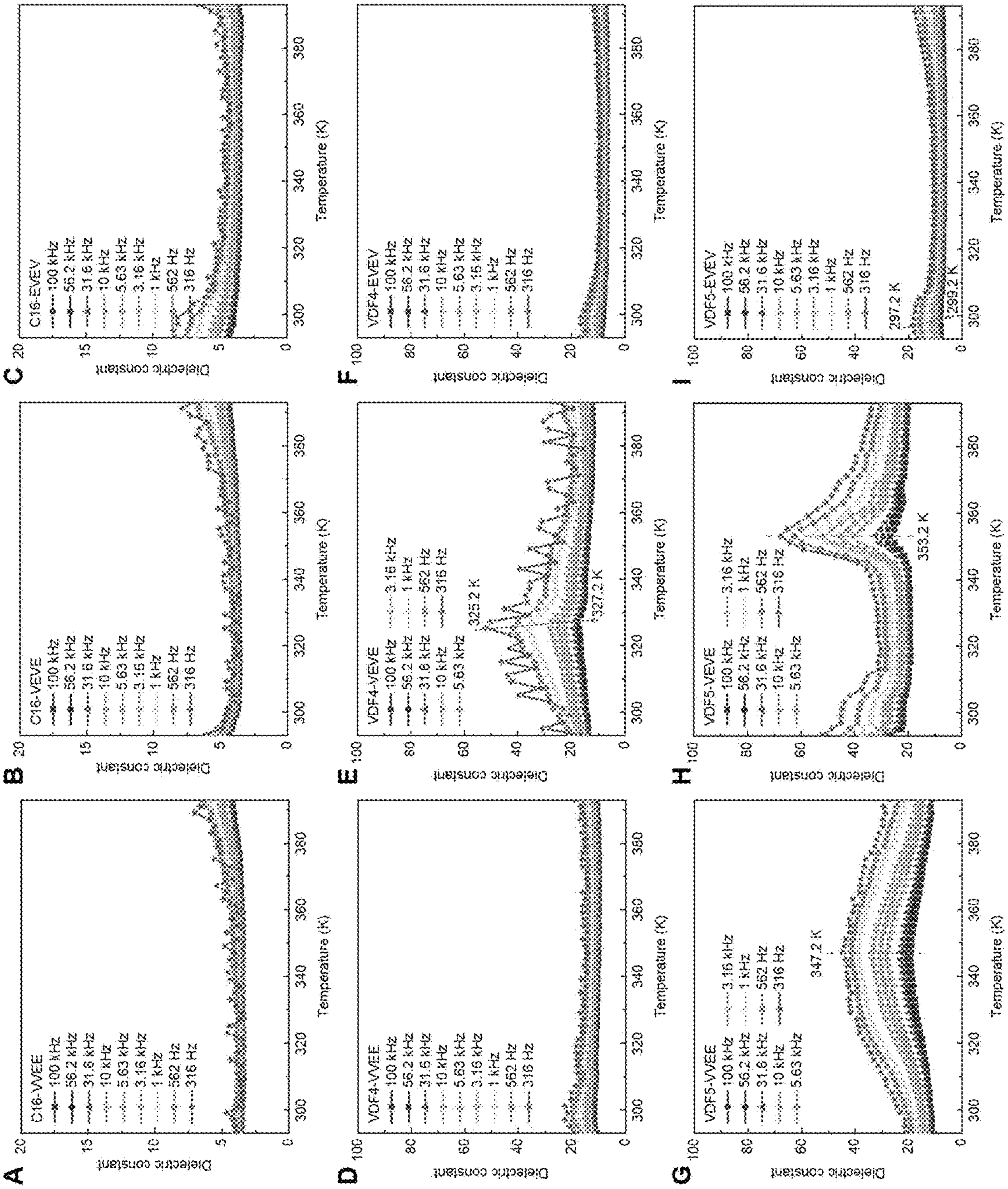
FIGS. 34A-34I show variable-temperature dielectric constant of the PA assembly thin films (FIG. 34A) C16-VVEE (SEQ ID NO: 1), (FIG. 34B) C16-VEVE (SEQ ID NO: 2), (FIG. 34C) C16-EVEV (SEQ ID NO: 3), (FIG. 34D) C16-VVEE (SEQ ID NO: 1), (FIG. 34E) VDF4-VEVE (SEQ ID NO: 2), (FIG. 34F) VDF4-EVEV (SEQ ID NO: 3), (FIG. 34G) VDF5-VVEE (SEQ ID NO: 1), (FIG. 34H) VDF5-VEVE (SEQ ID NO: 2), (FIG. 34I) VDF5-EVEV (SEQ ID NO: 3) under different frequencies.
Figure 35:
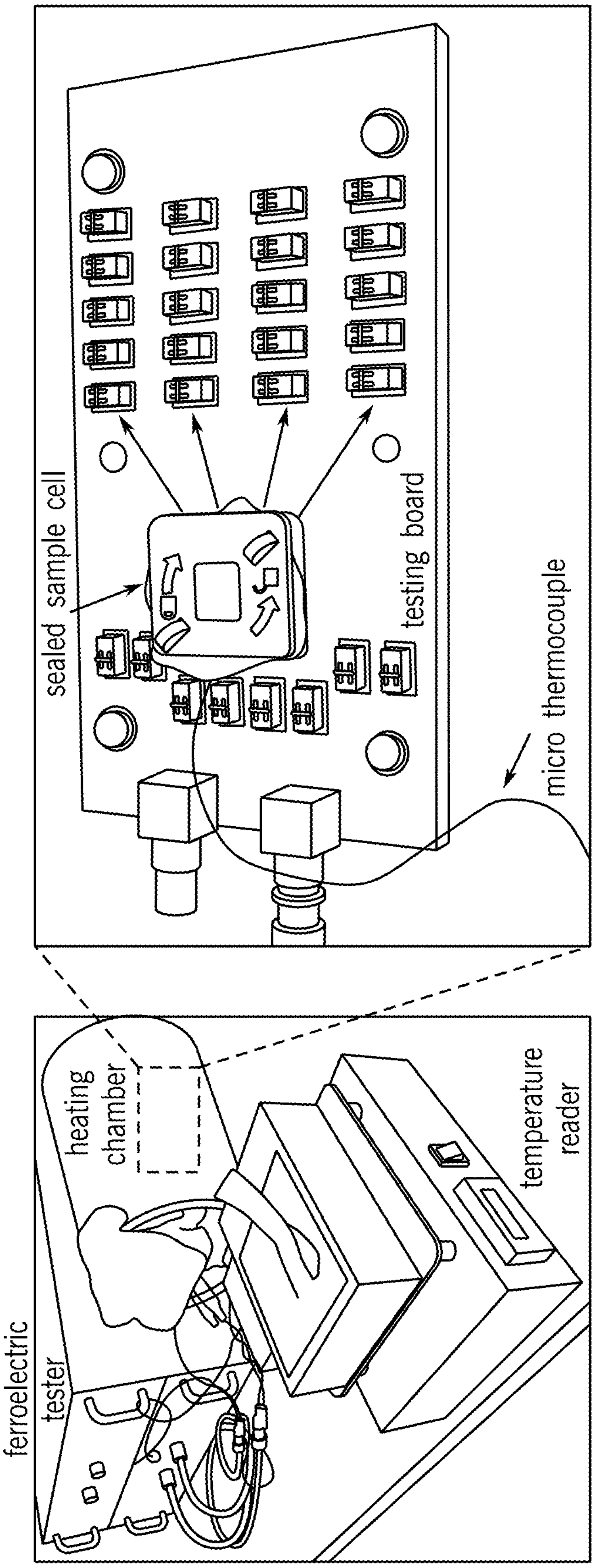
FIG. 35 shows experimental setups for the high-temperature P-E loop measurements of the PA assembly sample. A micro thermocouple is attached to the backside of the testing chip inside the sealed sample cell. The testing board is assembled and sealed in a nitrogen bag before testing.
Figures 36A, 36B, 36C, 36D, 36E, 36F:
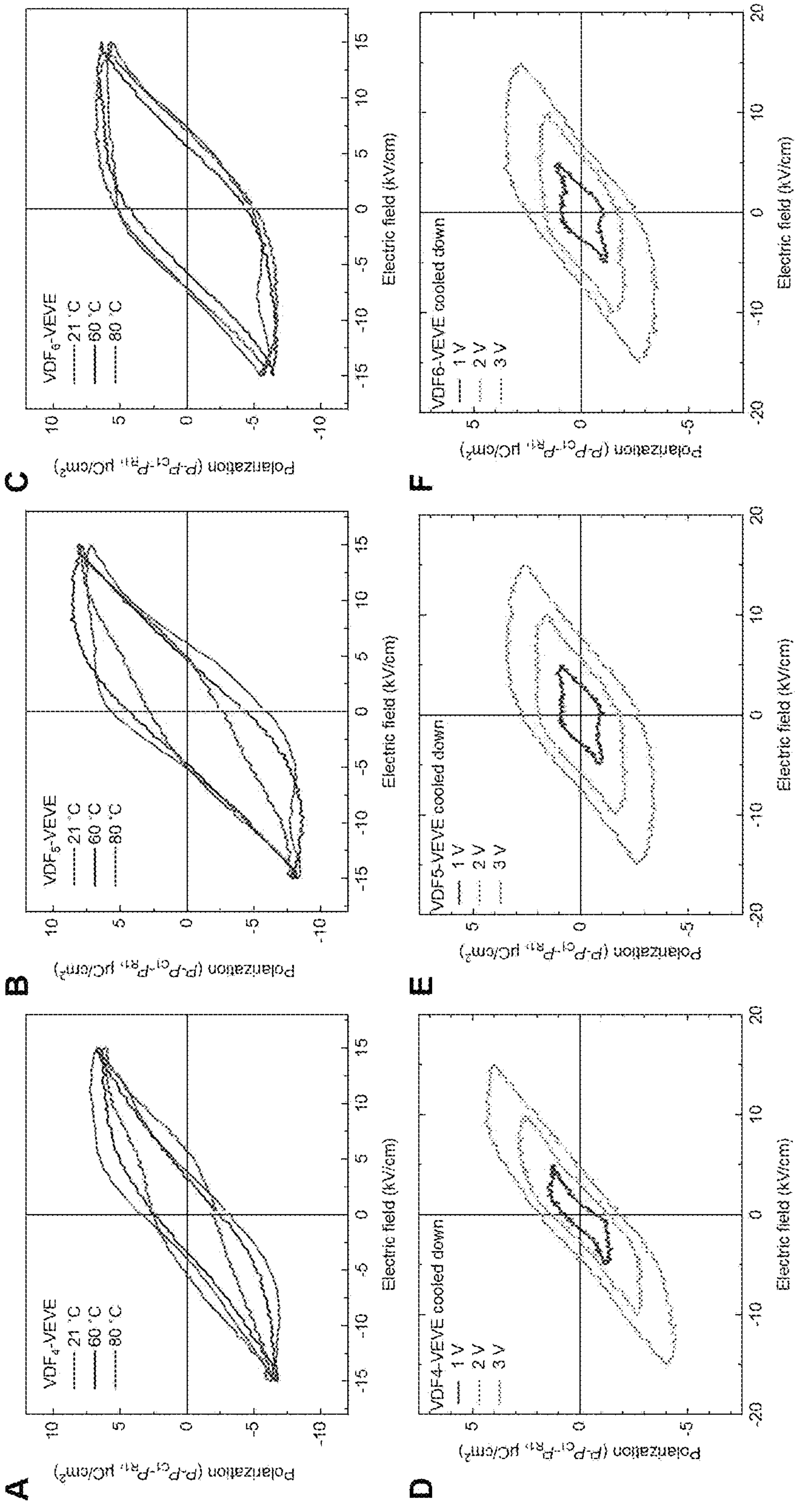
FIGS. 36A-36F show P-E loops of (FIG. 36A) VDF4-VEVE (SEQ ID NO: 2), (FIG. 36B) VDF5-VEVE (SEQ ID NO: 2) and (FIG. 36C) VDF6-VEVE (SEQ ID NO: 2) samples under room temperature (21° C.), 60° C. and 80° C. using the experimental setups shown in FIG. 35. P-E loops of (FIG. 36D) VDF4-VEVE (SEQ ID NO: 2), (FIG. 36E) VDF5-VEVE (SEQ ID NO: 2) and (FIG. 36F) VDF6-VEVE (SEQ ID NO: 2) after the samples are cooled down to room temperature following the high-temperature P-E loop measurements.

Distinguished from the ferroelectric hysteresis in VEVE (SEQ ID NO: 2) PA samples and the typical lossy dielectrics behavior in the short-tail (VDF4/VDFs5) VVEE (SEQ ID NO: 1) and EVEV (SEQ ID NO: 3) PA samples (FIG. 32), the slim non-axisymmetric P-E loops of VDF6-EVEV (SEQ ID NO: 3) inspired us to explore its potential relaxor ferroelectrics properties. The variable-temperature dielectric constant of the PA assembly thin films was measured at different frequencies. Unlike the narrow dielectric peaks of VDF6-VVEE (SEQ ID NO: 1) and VDF6-VEVE (SEQ ID NO: 2) associated with the ferroelectric-paraelectric (F-P) transition near the Curie temperature ($T_C$) (FIGS. 4, E and F), VDF6-EVEV (SEQ ID NO: 3) shows broad dielectric peaks shifting toward higher temperature with increasing frequency, exhibiting typical feature of relaxor ferroelectrics (*Science.* 280, 2101-2104 (1998)) (FIG. 4G). As shown in the inset of FIG. 4G, this frequency-dependent dispersion of dielectric peak temperature can be modeled well with the Vogel-Folcher law $$\ln f = \ln f_0 - U/[k_B(T_m - T_f)] \quad (1)$$

where f is the frequency, $f_0$ is the attempt frequency, U is the activation energy, kB is the Boltzmann constant, $T_m$ is the dielectric peak temperature (or intermediate temperature) and $T_f$ is the freezing temperature. The fitting yields $U=1.55\times10^{-3}$ cV, $f_0$=508 kHz and $T_f$=310.5 K (37.2° C.). The dielectric constant curves of the VDF-VEVE (SEQ ID NO: 2) and VDF-VVEE (SEQ ID NO: 1) PA assemblies also show decreasing $T_c$ as the VDF tail length decreases (FIG. 34), consistent with the domain size dependence of F-P transition (Polymer (Guildf). 54, 1709-1728 (2013)). The VDF6-VEVE (SEQ ID NO: 2) assemblies show the highest curie temperature of 110° C., much higher than the most widely used ferroelectric P(VDF-TrFE) copolymers ($T_c$ around 70° C.) (Phase Transitions. 18, 143-211 (1989)), demonstrating outstanding high temperature organic ferroelectrics. P-E loops measured under high-temperatures demonstrate that the VDV4-VEVE (SEQ ID NO: 2) and VDF5-VEVE (SEQ ID NO: 2) samples show decreased remanent polarization and more lossy behavior as the temperature increases to 80° C. while VDF6-VEVE (SEQ ID NO:2) exhibits stable ferroelectricity over a wide temperature range (FIG. 36).

Figures 37A, 37B, 37C:
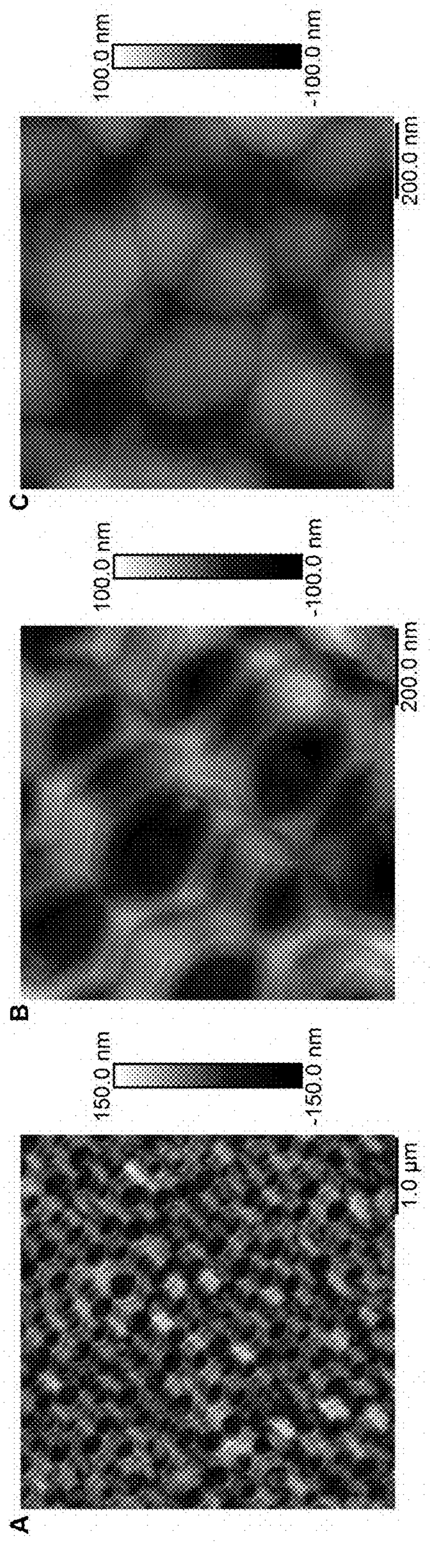
FIGS. 37A-37C show AFM morphologies of (FIG. 37A) porous AAO substrate, (FIG. 37B) zoomed in images showing the hollow channels and (FIG. 37C) AAO filled with annealed VDF6-VEVE (SEQ ID NO: 2) assemblies in dry state.
Figures 38A, 38B, 38C, 38D, 38E:
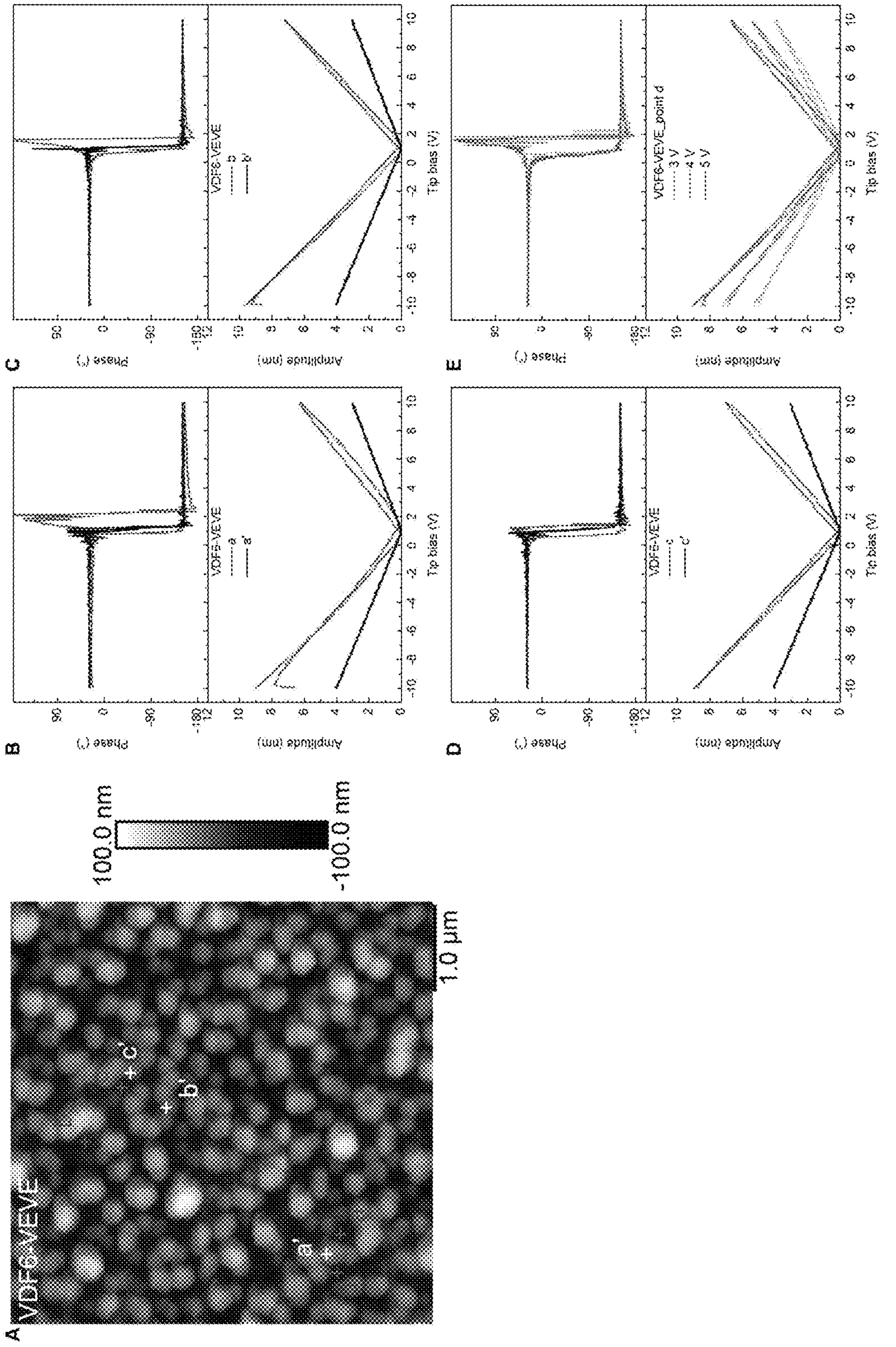
FIGS. 38A-38E show PFM measurement on the VDF6-VEVE (SEQ ID NO: 2) sample.

To investigate the electromechanical properties of the VDF-PA assemblies, piezoresponse force microscopy (PFM) was performed on aligned VDF6-PA assemblies that were prepared by annealing the freshly dissolved solution in porous anodic aluminum oxide (AAO) films with a conductive substrate, so that the electrical field can be applied along the elongation axes of the PA ribbons (FIG. 4H). A quasi-static tip bias voltage was swept on the sample to induce a piezoelectric state (*Science.* 375, 1418-1422 (2022)), while a high-frequency driving voltage was applied to the conductive substrate and the vibration of the sample at the same frequency can be detected by the tip with the electromechanical actuation amplitude and corresponding phase relative to the driving voltage recorded. As shown in FIG. 4I, and FIG. 38-37, VDF6-VEVE (SEQ ID NO: 2) exhibits typical piezoresponse phase hysteresis loops with the highest switching voltage while VDF6-VVEE shows lower hysteresis. VDF6-EVEV (SEQ ID NO: 3) shows the smallest hysteresis loop but the highest actuation amplitude, demonstrating low-hysteresis and high electromechanical performance. This is because the small domain size and weak domain intercoupling in the relaxor VDF6-EVEV (SEQ ID NO: 3) assemblies reduce the energy barrier of ferroelectric switching (*Science*. 374, 100-104 (2021)) and enable fast depolarization when the external electric field becomes zero.

This work shows that the ferroelectric phase of vinylidene fluoride, which is not thermodynamically stable in pure polyvinylidene fluoride (PVDF), can be obtained by templating the crystal structures of the oligomeric VDF chains in water using self-assembling peptide supramolecules. By attaching different peptide sequences, the induced crystallization behavior of the VDF regions and the resulting ferroelectric domain structures can be programmed to generate tunable ferroelectric and relaxor ferroelectric properties. This work provides the first water-processable VDF-based ferroelectric system. The tunable ferroelectric properties of the structures herein can be modified for various applications in minimally invasive biomedical devices, memory, sensor devices and electromechanical energy conversion.

Materials and Methods

Materials

All chemicals were purchased from Sigma-Aldrich, Thermo Fisher Scientific and used directly without any purification unless specified. 1,1-Difluoroethylene (VDF, 99%) gas was purchased from SynQuest Labs, USA. Ethylene (99.9%) gas was purchased from Airgas, Inc. USA. Bis(4-tert-butyl cyclohexyl) peroxydicarbonate (BTBCP) initiator was a gift from United Initiators, Inc., USA used as supplied.

Self-Assembly of Peptide Amphiphiles

Peptide amphiphiles (PA) were first dissolved in 1,1,1,3,3,3-Hexafluoro-2-propanol (HFIP) to disassemble any β-sheet-containing structures in the lyophilized powders thus allow for normalization of the fresh solutions. After evaporation of HFIP, the PA powders were dissolved in DI water at desired concentration followed by the addition of 1 equivalent of sodium hydroxide using a 1 M stock solution and water-bath sonication for 15 min. Then the solution was titrated to neutral (pH=6.8-7.0 by Hydrion pH paper) using 100 mM sodium hydroxide stock solution with about extra 0.2 equivalent of sodium hydroxide added. Solutions were then annealed at 80° C. unless specified otherwise in water bath (approximately 3 L) for 1 h followed by slowly cooling to room temperature.

Atomic Force Microscopy (AFM)

AFM experiments were performed on a Vecco Dimension icon scanning probe microscope (Vecco), Nanoscope V Controller (Bruker), at room temperature. The SNL-10-A probes (nominal tip radius 2 nm, spring constant 0.35 N/m, Bruker) were employed in liquid-state experiments using ScanAsyst in fluid imaging mode (Peakforce Force Tapping) at 2 kHz with an amplitude of 50 nm. The ScanAsyst-air probes (normal tip radius 2 nm, spring constant 0.4 N/m, Bruker) were employed in dry-state experiments using ScanAsyst in air imaging mode (Peakforce Force Tapping) at 2 kHz with an amplitude of 150 nm. Hight measurement on the PA assemblies were performed on Nanoscope Analysis software with the substrate height subtracted.

Transmission Electron Microscopy (TEM) and Selected Area Electron Diffraction (SAED)

TEM and SAED experiments were performed on a JEOL ARM300F field-emission transmission electron microscope equipped with a Gatan One View detector, with the acceleration voltage of 300 kV. Samples for TEM were diluted to 0.5~1 mM with 10 mM $NaCl_{aq}$ and immediately cast on glow-discharged carbon coated TEM grids (CF300-Cu-UL, Electron Microscopy Sciences). The grids were then negatively stained with 2 wt % uranyl acetate solution. For SAED, 10 mM PA solution was directly cast on glow-discharged carbon coated TEM grids, then wicked with filter paper. After drying, the samples were then washed with 5 μL of DI water, followed by wicking and drying.

Wide Angle X-Ray Scattering (WAXS)/Small Angle X-Ray Scattering (SAXS)

Solution X-ray measurements were performed at Beamline 5-ID-D in the DuPont-Northwestern-Dow Collaborative Access team (DND-CAT) Synchrotron Research Center at the Advanced Photon Source, Argonne National Laboratory. X-ray energy of 17 keV for room temperature measurements and 10 keV for variable temperature (VT) measurements were selected using a double-crystal monochromator. The scattering vector q is defined as $q=(4\pi/\lambda)\sin\theta$, where 2θ is the total scattering angle. Samples were oscillated with a syringe pump during exposure to prevent beam damage. Background samples containing 10 mM $NaCl_{aq}$ were also collected to perform background subtraction.

For VT measurements, the annealed solution of VDF-PA (20 mM, 20 mM NaCl) was encapsulated inside the capillary. Starting at 33° C., the solution was heated in 4° C. steps each at 1° C./min. The 1 min heating segment was followed by a 1 min equilibration segment and subsequent data acquisition. During data collecting the sample was oscillated inside the capillary to minimize any beam damage to the sample. Both empty and buffer-filled vacuum capillary scattering data were recorded with the same VT protocol to ensure appropriate background subtraction.

Fourier-Transform Infrared (FTIR) Spectroscopy

Attenuated total reflectance (ATR) FTIR spectroscopy was performed on a Nexus 870 spectrometer (Thermo Nicolet). Liquid samples were measured by adding 0.5 μL PA solution covering the crystal surface of the ATR module and the background signal was collected on 10 mM NaCl solution. Measurements on dry-state samples were performed after the liquid samples were dried in air.

To prepare the aligned VDF6-PA assembly samples for the polarized transmission FTIR, polydimethylsiloxane (PDMS) embossing stamps were prepared using a plane ruled reflective grating (Edmund, 300 grooves/mm, 12.5×25 mm, blaze angle 26.7°) as the template. Then the PDMS stamps were attached on a 0.5 mm thick N type Germanium wafer (MSE Supplies LLC) and forms micro channels on the wafer. The freshly dissolved 10 mM VDF6-PA solutions were prepared after HFIP treatment and immediately added to one edge of the PDMS stamps with the openings of the micro channels. After the solution fulfilled the micro channels by capillary effect, the wafer was sealed in a glass bottle containing some water to keep the high humidity then annealed at 80° C. in water bath (approximately 3 L) for 1 h followed by slowly cooling to room temperature. Finally, the samples were dried in vacuum and aligned PA assemblies were left on the wafer after removing the PDMS stamp. Transmission FTIR were performed with a polarizer inserted in the light path and the electric field of the incident IR laser was fixed parallel (0°) or perpendicular (90°) to the elongation axis of the PA fibers.

Differential Scanning Calorimetry

The annealed 20 mM PA solutions were diluted to 1.25 mM in water to prepare the samples for DSC measurements. DSC thermograms were obtained using a Nano DSC instrument (TA Instruments, model 602001) under constant pressure (6.0 atm) with the sample matched against 1.25 mM NaCl buffer in the reference cell. Samples were cooled down to 5° C. then equilibrated for 600 s, followed by 3 alternating heating and cooling cycles from 5° C. to 120° C. at a scan rate of 1° C./min. A 600 s equilibration period is added before each heating and cooling cycle. Cooling data was analyzed and converted to molar heating capacity using NanoAnalyze Data Analysis, version 3.12.0, from TA Instruments.

P-E Loop and Ferroelectricity Measurements

Annealed 20 mM sample solution was deposited on a silicon testing chip with 100 nm thick $SiO_2$ insulation layer and photolithographically patterned platinum electrodes with 2 μm channel width (Ossila, S403A1), the cross-section of the electrode is 1 mm wide and 100 nm thick. The samples were dried in high vacuum (2×10–7 mbar) overnight before electrical tests. To avoid the influence of air and moisture, the chip was sealed on the testing board (Ossila, E481) and the board was sealed in a nitrogen bag during the measurement. Polarization-electric field (P-E) loops were measured using a ferroelectric tester (Radiant Technologies Precision LC) at room temperature unless specified otherwise. Double bipolar triangle waveforms were applied with a single loop period of 50 ms, a pre-loop delay between the two loops of 10 ms and maximum voltages of 0.8~4.5 V. The final loop was recorded as the original P-E loop data. The resistance of the samples was measured using the same setup. DC voltage of 1~5 V was applied while the leakage current was recorded for 10 s until the polarization process was complete. The frequency-domain impedance spectrum was measured using AutoLab PGSTAT-128N (voltage amplitude of 0.1 to 0.3 V) and Solartron 1260 (voltage amplitude of 0.2 to 1.0 V) at room temperature. The ferroelectric component was obtained after subtracting the contribution of $C_1$ and $R_1$ from the original P-E loop (FIG. 26). High temperature P-E loop measurements were performed with a micro thermocoupler. The linear capacitor $C_1$, corresponding to the linear polarization mechanisms including electrons/ions elastic displacement, dipole reorientation, etc. (1), contributes to polarization $P_{C1}$ $$P_{C1} = C_1 Ed/S \quad \text{(S1)}$$

where E is the applied electric field, d is electrode spacing, S is the cross-sectional area of the electrode. The resistor $R_1$ represents the conduction loss of the sample, contributing to elliptic polarization curves $P_{R1}$ in P-E loops under sine waveform (1):

$$(SR_1\omega/U_0)^2 P_{R1}^2 + (d/U_0)^2 E^2 = 1 \quad \text{(S2)}$$

where ω is the angular frequency of the applied voltage, $U_0$ is the voltage amplitude. For the applied triangle waveform, the base frequency component of the waveform is considered to perform the subtraction of the resistor.

Variable-Temperature Dielectric Constant Measurements

Figures 33A, 33B:
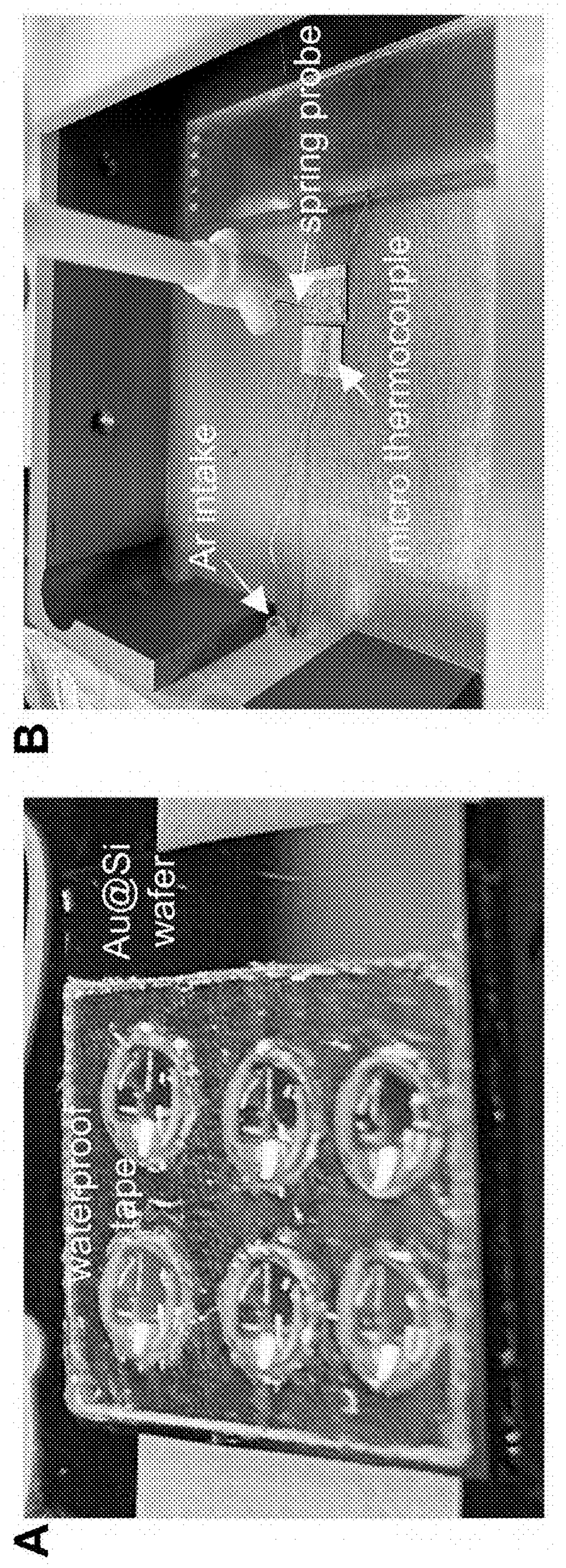
FIGS. 33A-33B show sample preparation and measurement setup for variable-temperature dielectric constant tests.

Thin films of the PA samples with the thickness of 20-40 μm measured by a thickness gauge (Mitutoyo) were prepared by casting each 20 mM annealed solution on a gold-plated silicon wafer (FIG. 33) followed by evaporation of water and dried in vacuum at room temperature. The variable-temperature frequency domain impedance measurements were performed using AutoLab PGSTAT-128N under voltage amplitude of 0.5 V. Due to the fragile nature of dry PA assembly films, a spring test probe with spherical tip (0.6 mm diameter) was applied as the top electrode with the equivalent electrode area calibrated by a 25 μm polyimide standard film (Dupont, Kapton) (FIG. 33). The samples were mounted on a heating stage with a micro thermocouple nearby and the sample cell was blown with Ar gas during experiments. Before the measurements, the samples were heated to 40° C. for 30 min to remove moisture, then a temperature sweep from 22 to 120° C. was applied at a scanning rate of 1° C./min and the impedance was measured from 1 Hz to 100 kHz at every step of 2° C. Then the complex impedance data was converted to complex capacitance and dielectric constant of the samples were calculated according to the real part of the complex capacitance.

Piezoresponse Force Microscopy (PFM)

Porous anodic aluminum oxide (AAO) films with conductive Al substrate (InRedox), 300 nm pore diameter and 2 μm thickness were used as the template to assemble the VDF-PA nanostructures in perpendicular to the conductive substrate. Freshly dissolved 20 mM VDF-PA aqueous solution after HFIP treatment was added to the AAO substrate. The AAO substrate immersed in PA solution was sealed in a glass bottle containing some water to keep the high humidity then annealed at 80° C. in water bath (approximately 3 L) for 1 h followed by slowly cooling to room temperature. The extra annealed PA solution on the surface of the substrate was blown off by $N_2$ and the above steps were repeated once. Finally, the samples were dried in vacuum and aligned PA assemblies were left inside the pore channels with the elongation axes aligned in the out-of-plan direction. AFM morphology measurements were performed to confirm the fulfill of the pore channels and removal of stacked extra PA assemblies on the surface of the samples.

Figures 39A, 39B, 39C, 39D, 39E:
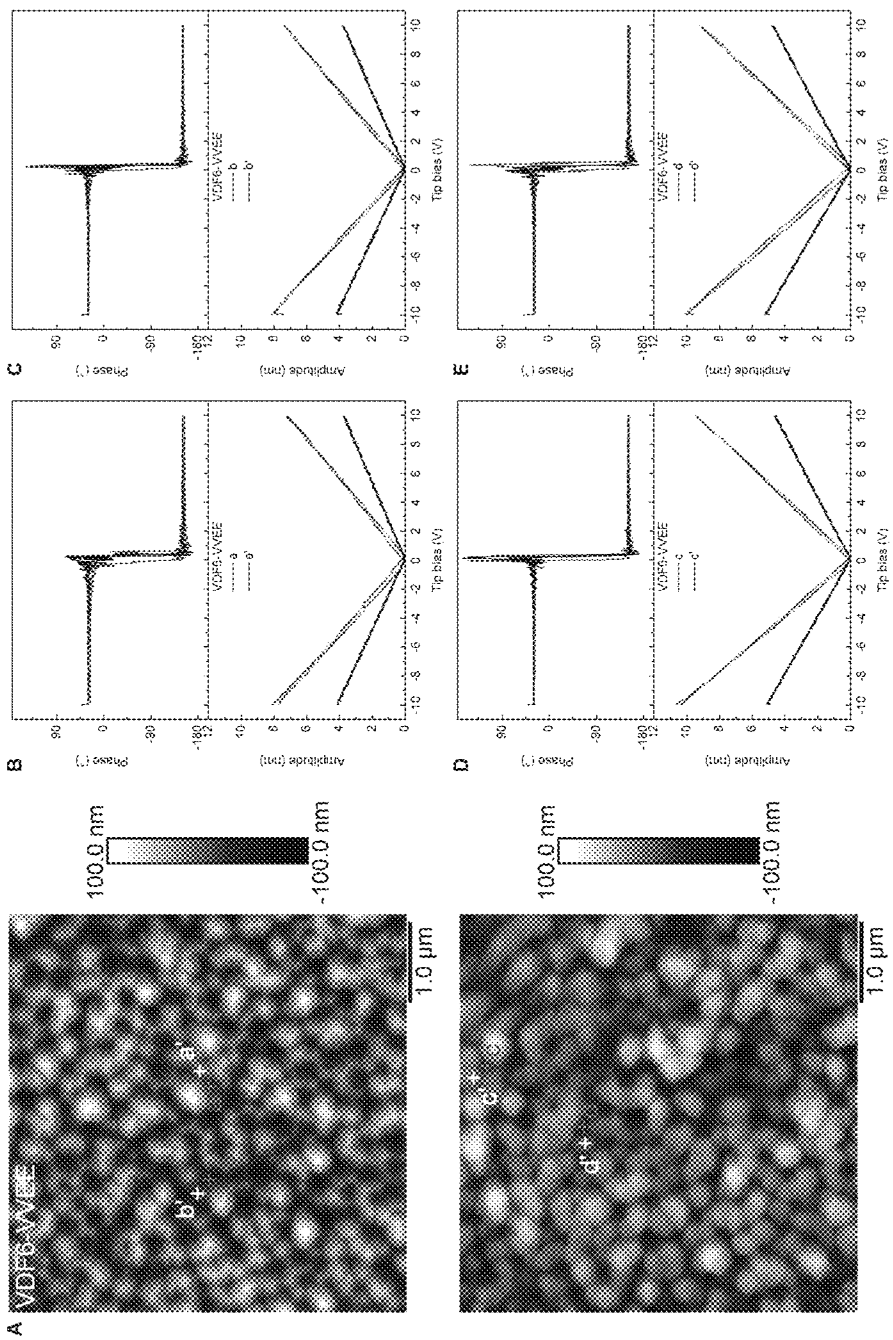
FIGS. 39A-39E show PFM measurement on the VDF6-VVEE (SEQ ID NO: 1) sample.
Figures 40A, 40B, 40C, 40D, 40E:
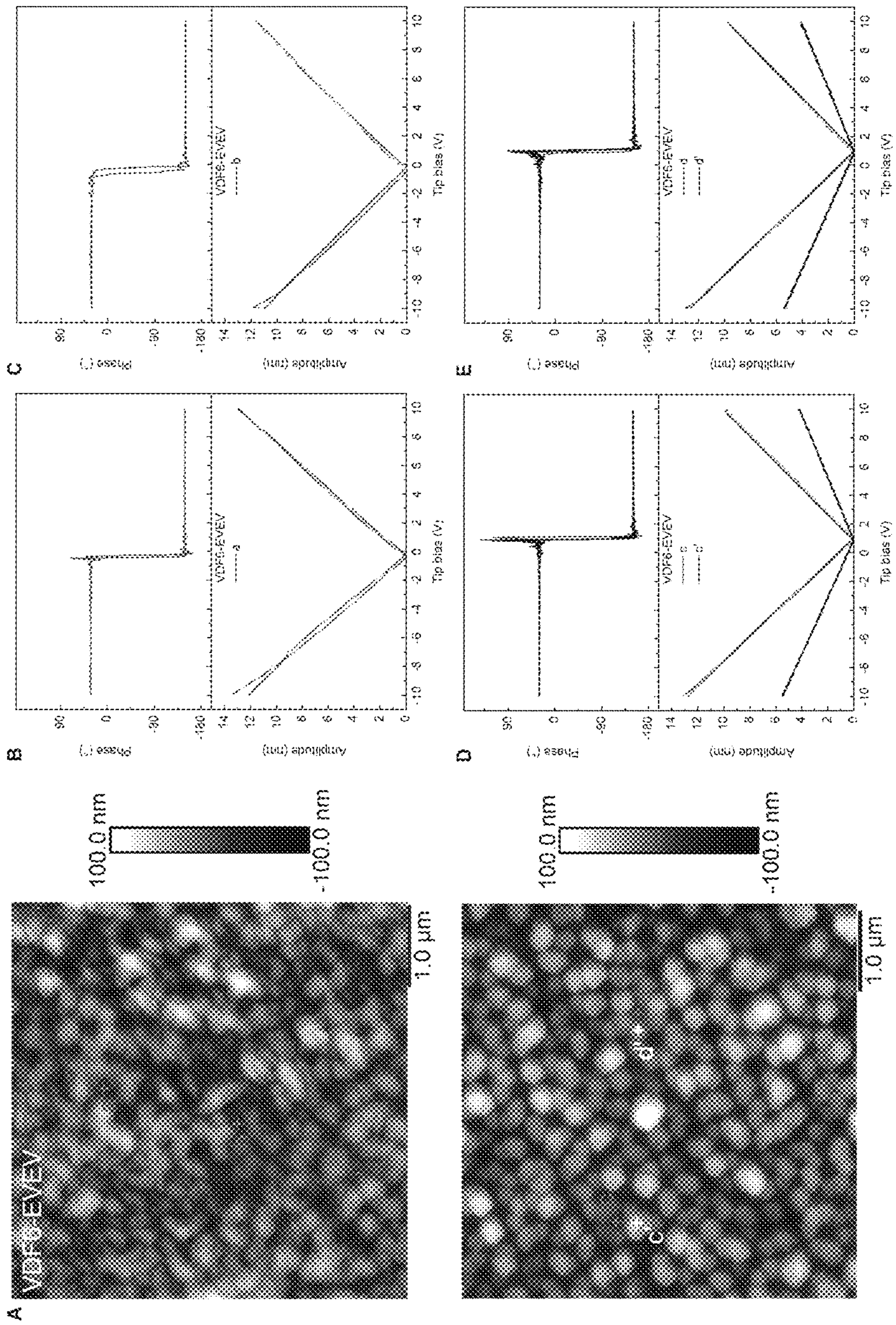
FIGS. 40A-40E show PFM measurement on the VDF6-EVEV (SEQ ID NO: 3) sample.
Figures 41A, 41B, 41C:
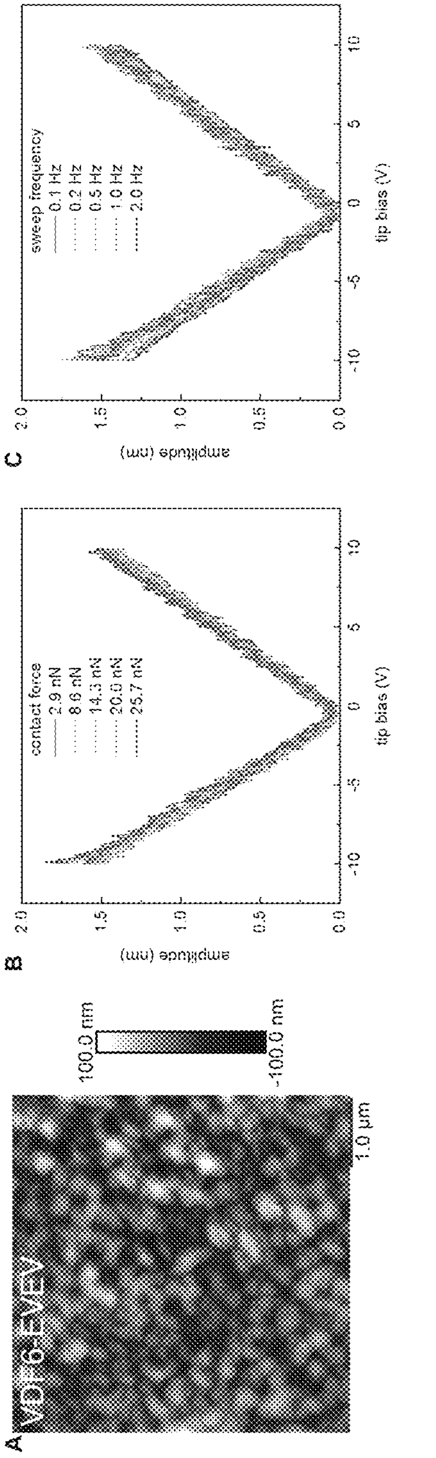
FIGS. 41A-41C show verification PFM measurement on the VDF6-EVEV (SEQ ID NO: 3) sample.

PFM measurements were performed on the same AFM instrument. The conductive PFTUNA probes (Pt/Ir coating, nominal tip radius 25 nm, spring constant 0.4 N/m, Bruker) were employed to perform high resolution morphology measurements using ScanAsyst in air imaging mode (Peakforce Force Tapping) and electromechanical measurements using ramp mode in PFM Optimized Vertical Domains Operation workspace on the dry-state samples in AAO films. The deflection sensitivity of the probe was measured against a sapphire standard in air as 41.61 nm/V). PFM loops were measured with the contact force of 8.6 nN, tip bias voltage swept between +10 V at 20 V/s (0.5 Hz) to polarize the sample and a 50 kHz oscillating driving voltage with the amplitude of 1 to 5 V (5 V if not specified) applied to the conductive substrate to induce electromechanical actuation without disturbing the orientation of ferroelectric domains. The PFM loops were measured in the fulfilled pores and neighboring AAO walls (FIG. 38, FIG. 39, FIG. 40) to validate the measured properties on the PA samples in the pores. Verification tests were performed on the AAO wall areas on VDF6-EVEV (SEQ ID NO: 3) samples using different contact forces (2.9, 8.6, 14.3, 20.0 and 25.7 nN) and sweeping frequencies of tip bias (0.1, 0.2, 0.5, 1.0 and 2.0 Hz) ruling out the effects of sample surface charge and electromigration of ions respectively (FIG. 41).

Synthesis of Vinylidene Fluoride (VDF) Oligomer Acid and Peptide Amphiphile (PA)

VDF oligomer acid and PA was synthesized as shown in FIG. XX.

Telomerization of VDF with $CF_{31}$ (a).

Radical telomerizations of VDF were performed in a 50-mL high-pressure autoclave (Parr Instruments, USA, 2430HC2) with trifluoroiodomethane as the chain transfer agent (CTA) and initiated by bis(4-tert-butyl cyclohexyl) peroxydicarbonate (BTBCP) at 60° C. with the molar feed of [VDF]/[CTA]/[BTBCP]=1/0.5/0.13. The autoclave was first filled with a suspension of BTBCP (2.65 g, 6.65 mmol) in a mixture solvent of 16 mL 1,1,1,3,3-pentafluorobutanc (PFB). Then it was pressurized with 30 bar of $N_2$ to check for leaks and cooled down to <−60° C. in liquid nitrogen bath under a vacuum with the gauge pressure of −12 psi. Utilizing a 500 mL exchange tank, 0.025 mmol (pressure drop 16.5 psi) of trifluoroiodomethane gas and 0.05 mmol (pressure drop 33 psi) of vinylidene fluoride gas were condensed into the autoclave. Then the reactor was warmed up, stirred at 250 rpm and slowly heated to 60° C. After 7 h-reaction, the gauge pressure of the reactor dropped from 140 psi to 80 psi, the autoclave was placed in an ice bath for 30 min and unreacted gas was progressively released. Finally, a light-yellow color liquid was obtained, the solvent and traces of monomers and CTA were removed by evaporation at 40° C. under reduced pressure (100 mmHg) to obtain a viscous and yellow product. The telomers with the polymerization degree x=3-6 was purified via a Combi-flash RF 200 auto column system (Teledyne Isco, Inc.) equipped with a RediSep Rf Gold normal phase silica flash column using hexanes/ethyl acetate as eluent. After evaporation at 40° C. under reduced pressure (100 mmHg), yellow liquids (x=3, 4) and viscous (x=5, 6) products with yields of 13.3% (x=3, VDF3-I), 15.6% (x=4, VDF4-I), 13.4% (n=5, VDF5-1) and 8% (n=6, VDF6-I). The negligible signals between −113 and −116 ppm, assigned to the $CF_2$ groups of reversed VDF units (—$CH_2$—$CF_2$—$CF_2$—$CH_2$—), demonstrate a controlled behavior of the telomerization. $^{19}$F-NMR (400 MHZ, $CDCl_3$) δ (ppm): −38.3 (—$CF_2$—I, 2F), −61.7 ($CF_3$—, 3F), −90 to −91.5 (—$CH_2$—$CF_2$—$CH_2$—, 2F), negligible signals from −113 to −116 (—$CH_2$—$CF_2$—$CF_2$—$CH_2$—).

$^1$H-NMR (400 MHZ, $CDCl_3$) δ (ppm): 2.66 to 2.98 (m, —$CF_2$—$CH_2$—$CF_2$—, 2H), 3.28 to 3.43 (m, $CF_3$—$CH_2$—, 2H), 3.55 to 3.67 (m, —$CH_2$—$CF_2$-1, 2H).

Ethylenation of VDF Telomers (b).

Take the VDF4-I telomer as the main product of the previous step, 12.5 mmol (5.65 g) of the VDF telomer, BTBCP (1.325 g, 3.325 mmol) and 16 mL of tert-butanol were filled into the autoclave followed by the same procedure of leak check and cooling down. By using the 500 mL exchange tank, 0.03 mmol (pressure drop 19.8 psi) of ethylene (E) gas were transferred into the reactor. Then the reactor was warmed up, stirred at 250 rpm and slowly heated to 60° C. After 8 h-reaction, the autoclave was placed in an ice bath for 30 min and unreacted gas was progressively released. Finally, a yellow-to-orange color liquid was obtained. Deionized (DI) water (20 mL) and 5 mL PFB were added to the liquid then shaken in a centrifuge tube to obtain separated two phases: aqueous solution of tert-butanol (upper) and organofluorinated products in PFB (lower). This operation was repeated twice, then the organofluorinated phase was dried over $MgSO_4$ and filtered. The PFB solvent was removed by evaporation at 40° C. under reduced pressure (100 mmHg) to obtain the viscous yellow ethylene end-capped product VDF4-E-I (5.1 g, 10.6 mmol, 84.8%).

$^{19}$F-NMR (400 MHZ, $CDCl_3$) δ (ppm): absence of signal around −38, −61.6 ($CF_3$—, 3F), −90 to −91.5 (—$CH_2$—$CF_2$—$CH_2$—, 2F).

$^1$H-NMR (400 MHz, $CDCl_3$) δ (ppm): 2.52 to 2.65 (m, —$CH_2$—$CH_2$—I), 2.67 to 2.98 (m, —$CF_2$—$CH_2$—$CF_2$—, 2H), 3.15 to 3.25 (m, $CF_3$—$CH_2$—, 2H), 3.45 to 3.53 (m, —$CH_2$—$CH_2$-1, 2H), eliminated signal from 3.55 to 3.67.

Hydrolysis of Ethylenated VDF Telomers (c).

Take the VDF4-E-I as the main product of the previous step, VDF4-E-I (8 g, 0.017 mol) were dissolved in a mixture of N,N-Dimethylformamide (DMF, 18.4 mL, 0.24 mol) and DI water (0.72 mL, 0.04 mol). The liquid was purged by argon for 15 min followed by stirring for 6 h at 120° C. under reflux and the liquid turned dark brown. Then the reaction mixture was washed up 3 times with hot DI water (ca. 80° C.) to remove DMF and the organofluorinated phase (lower) was dissolved in ethyl acetate and dried over $MgSO_4$ and filtered. After evaporation of ethyl acetate, the waxy mixture of two products was obtained: the fluorinated alcohol VDF4-E-OH and the formiate VDF4-$CH_2$—OCHO with the total yield of about 60 wt. %. Both products were characterized by $^1$H NMR spectroscopy which confirmed the produced alcohol (3.63 ppm assigned to $CH_2OH$) and the formiate (4.01 and 8.03 ppm assigned to the methylene group and H end atom in-$CH_2OCHO$, respectively).

The $^{19}$F NMR spectra of VDF4-E-OH and VDF4-E-OCHO are similar as the VDF-E-I.

$^1$H-NMR (400 MHZ, $CDCl_3$) δ (ppm): 2.55 to 2.65 (m, —$CH_2$—$CF_2$—($CH_2$) 2-OH, 2H), 2.65 to 2.95 (m, —$CF_2$—$CH_2$—$CF_2$—, 2H), 3.15 to 3.25 (m, $CF_3$—$CH_2$—, 2H), 3.45 (m, —$CH_2$—OH, 1H), 3.63 (m, —$CH_2$—$CH_2$—OH), 4.01 (m, —$CH_2$—OCHO), 8.03 (s, —OCHO, 1H).

Saponification of the Fluorinated Formiate (d).

The hydrolyzed derivative produced above (4.8 g, about 0.01 mol) were dissolved in 20 mL $CH_3OH$ then a mixture of $H_2SO_4$ (1.07 mL, 0.02 mol) and DI water (2.14 mL) weas added to the solution dropwise while stirring. The mixture was purged by argon for 15 min followed by stirring for 5 h at 80° C. under reflux. Then the reaction mixture was washed up 3 times with hot DI water (ca. 80° C.) and the organofluorinated phase (lower) was dissolved in ethyl acetate and dried over $MgSO_4$ and filtered. After evaporation of ethyl acetate, yellow waxy product of VDF4-E-OH (yield 83 wt. %) was obtained. Complete saponification of the formiate was confirmed by the absence of the peak centered at 8.03 ppm in $^1$H NMR spectrum.

The $^{19}$F NMR spectra of VDF4-E-OH is similar as the VDF4-E-I.

$^1$H-NMR (400 MHZ, $CDCl_3$) δ (ppm): similar as the above mixtures except for the absence of signal around 8, 3.33 (m, —$CH_2$—OH, shifted with dilution, 1H).

Oxidation of the VDFx-E-OH Alcohol into VDFx-COOH Acid (e).

Take the VDF4-E-OH as an example, the fluorinated alcohol VDF4-E-OH (1.25 g, 2.9 mmol) was dissolved in a mixture of 9 mL acetone and 3 mL diethyl ether. Jones catalyst, prepared by adding $CrO_3$ (1.16 g, 11.6 mmol) then $H_2SO_4$ (1.16 mL) into DI water (3.248 mL), was dropwise added into the solution with stirring until a brown color of the mixture became persistent. After 2-hour stirring, the solid by-product was removed, the product mixture was washed by DI water twice and the fluorinated organic phase was extracted with diethyl ether and dried over $MgSO_4$ and filtered. The final product VDF4-COOH was obtained as light-yellow solid by drying in vacuum overnight (yield 75%). Complete oxidation of the alcohol was confirmed by the absence of the peak centered at 3.4 ppm (assigned to —$CH_2OH$) and the presence of a peak centered at 2.04 ppm assigned to the methylene group adjacent to the carboxylic acid in $^1$H NMR spectrum.

The $^{19}$F NMR spectra of VDF4-COOH is similar as the VDF4-E-OH.

$^1$H-NMR (400 MHZ, $CDCl_3$) δ (ppm): 2.04 (s, —$CH_2$—COOH, 2H), 2.65 to 2.95 (m, —$CF_2$—$CH_2$—$CF_2$—, 2H), absence of signal around 3.4, 9.75 to 9.85 (broad signal, —COOH, 1H).

Solid-Phase Synthesis of VDF-PA

Peptide amphiphiles were synthesized using standard 9-fluorenylmethoxycarbonyl (Fmoc) solid-phase peptide synthesis (0.25 mmol scale) using Fmoc-Rink amide 4-methyl benzhydrylamine hydrochloride (MBHA) resin as shown in FIG. XX.

Fmoc deprotections were performed with 20% 4-methylpiperidine in DMF solution for 10 min. Amino acid coupling reactions were carried out using a coupling mixture of amino acid/HBTU/DIEA (4:3.95:6 relative to the resin) in DMF. Cleavage of the peptides from the resin was carried out with a mixture of trifluoroacetic acid (TFA)/water/triisopropylsilane (TIPS)/dichloromethane (DCM) in a ratio of 95:1:1:3 for 2 hours. After removal of excess TFA by rotary evaporation, the remaining peptide solution was triturated with cold diethyl ether to obtain a slightly yellow precipitate solid, followed by drying under nitrogen purge overnight. The peptides were purified by preparative reverse phase HPLC using a Phenomenex Gemini column (NX-C18, 5 μm, 110 Å, 150×30 mm) at 25° C. on a Shimadzu Prominence Preparative HPLC system. Water/acetonitrile gradient containing 0.1 vol % $NH_4OH$ was used as an eluent at a flow rate of 25 mL/min. The purified fractions were collected and concentrated by rotary evaporation to remove acetonitrile, then lyophilized and stored at −20° C. Products were characterized by electrospray ionization mass spectrometry (ESI-MS) using a Bruker AmaZon-SL instrument, with 0.1% $NH_4OH$ in a water/acetonitrile mix (50:50) as eluent.

In total, 15 peptide amphiphiles were synthesized and characterized:

C16-VVEE (SEQ ID NO: 1), C16-VEVE (SEQ ID NO: 2) and C16-EVEV (SEQ ID NO: 3): Calc. 711.48, found $[M-H]^-$ 710.6, $[M-2H]^{2-}$ 354.6 and $[M-2H+Na]^-$ 732.6.

VDF3-VVEE (SEQ ID NO: 1), VDF3-VEVE (SEQ ID NO: 2), and VDF3-EVEV (SEQ ID NO: 3): Calc. 775.28, found $[M+H]^+$ 774.4, and $[M-2H]^{2-}$ 386.5.

VDF4-VVEE (SEQ ID NO: 1), VDF4-VEVE (SEQ ID NO: 2), and VDF4-EVEV (SEQ ID NO: 3): Calc. 839.30, found $[M-H]^-$ 838.4, and $[M-2H]^{2-}$ 418.5.

VDF5-VVEE (SEQ ID NO: 1), VDF5-VEVE (SEQ ID NO: 2), and VDF5-EVEV (SEQ ID NO: 3): Calc. 903.31, found $[M-H]^-$ 902.4, and $[M-2H]^{2-}$ 450.5.

VDF6-VVEE (SEQ ID NO: 1), VDF6-VEVE (SEQ ID NO: 2), and VDF6-EVEV (SEQ ID NO: 3): Calc. 967.32, found $[M-H]^-$ 966.5, and $[M-2H]^{2-}$ 482.6.

It is understood that the foregoing detailed description and accompanying examples are merely illustrative and are not to be taken as limitations upon the scope of the disclosure, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the disclosure, may be made without departing from the spirit and scope thereof.

Any patents and publications referenced herein are herein incorporated by reference in their entireties.

SEQUENCE LISTING

```
Sequence total quantity: 9
SEQ ID NO: 1            moltype = AA  length = 4
FEATURE                 Location/Qualifiers
source                  1..4
                        mol_type = protein
                        organism = synthetic construct
SEQUENCE: 1
VVEE                                                                4

SEQ ID NO: 2            moltype = AA  length = 4
FEATURE                 Location/Qualifiers
source                  1..4
                        mol_type = protein
                        organism = synthetic construct
SEQUENCE: 2
VEVE                                                                4

SEQ ID NO: 3            moltype = AA  length = 4
FEATURE                 Location/Qualifiers
source                  1..4
                        mol_type = protein
                        organism = synthetic construct
SEQUENCE: 3
EVEV                                                                4

SEQ ID NO: 4            moltype = AA  length = 6
FEATURE                 Location/Qualifiers
source                  1..6
                        mol_type = protein
                        organism = synthetic construct
SEQUENCE: 4
VVVEEE                                                              6

SEQ ID NO: 5            moltype = AA  length = 6
FEATURE                 Location/Qualifiers
source                  1..6
                        mol_type = protein
                        organism = synthetic construct
SEQUENCE: 5
VEVEVE                                                              6
```

-continued

```
SEQ ID NO: 6              moltype = AA  length = 6
FEATURE                   Location/Qualifiers
source                    1..6
                          mol_type = protein
                          organism = synthetic construct
SEQUENCE: 6
EVEVEV                                                          6

SEQ ID NO: 7              moltype = AA  length = 8
FEATURE                   Location/Qualifiers
source                    1..8
                          mol_type = protein
                          organism = synthetic construct
SEQUENCE: 7
VVVVEEEE                                                        8

SEQ ID NO: 8              moltype = AA  length = 8
FEATURE                   Location/Qualifiers
source                    1..8
                          mol_type = protein
                          organism = synthetic construct
SEQUENCE: 8
VEVEVEVE                                                        8

SEQ ID NO: 9              moltype = AA  length = 8
FEATURE                   Location/Qualifiers
source                    1..8
                          mol_type = protein
                          organism = synthetic construct
SEQUENCE: 9
EVEVEVEV                                                        8
```

The invention claimed is:

1. A peptide amphiphile comprising a β-sheet forming peptide sequence conjugated to a poly(vinylidene) fluoride (PVDF) comprising two or more vinylidene fluoride (VDF) monomers.

2. The peptide amphiphile of claim 1, wherein the β-sheet forming peptide sequence has a total propensity for forming β-sheets of at least 5.

3. The peptide amphiphile of claim 1, wherein the β-sheet forming peptide sequence is 4-10 amino acid residues in length.

4. The peptide amphiphile of claim 3, wherein each of the 4-10 amino acid residues is independently selected from valine (V), glutamic acid (E), and aspartic acid (D).

5. The peptide amphiphile of claim 3, wherein at least 50% of the 4 to 10 amino acid residues are valine residues.

6. The peptide amphiphile of claim 1, wherein the β-sheet forming peptide sequence is at least 4 amino acids in length and has a total propensity for forming β-sheets of at least 5.

7. The peptide amphiphile of claim 1, wherein the β-sheet forming peptide sequence comprises VVEE (SEQ ID NO: 1), VEVE (SEQ ID NO: 2), or EVEV (SEQ ID NO: 3).

8. The peptide amphiphile of claim 1, wherein the PVDF of 3 to 10 VDF monomers.

9. The peptide amphiphile of claim 1, wherein the PVDF consists of three VDF monomers (VDF3), four VDF monomers (VDF4), five VDF monomers (VDF5), or six VDF monomers (VDF6).

10. The peptide amphiphile of claim 9, comprising VDF6-EVEV (SEQ ID NO: 3), VDF6-VEVE (SEQ ID NO: 2), or VDF6-VVEE (SEQ ID NO: 1).

11. A nanoscale ferroelectric structure comprising a plurality of self-assembled peptide amphiphiles, wherein each peptide amphiphile independently comprises a β-sheet forming peptide sequence conjugated to a poly(vinylidene) fluoride comprising two or more vinylidene fluoride (VDF) monomers.

12. The structure of claim 11, wherein the β-sheet forming peptide sequence of each peptide amphiphile has a total propensity for forming β-sheets of at least 5.

13. The structure of claim 11, wherein the β-sheet forming peptide sequence of each peptide amphiphile is 4-10 amino acid residues in length.

14. The structure of claim 13, wherein each of the 4-10 amino acid residues is independently selected from valine (V), glutamic acid (E), and aspartic acid (D).

15. The structure of claim 13, wherein at least 50% of the 4 to 10 amino acid residues are valine residues.

16. The structure of claim 11, wherein the β-sheet forming peptide sequence of each peptide amphiphile is at least 4 amino acids in length and has a total propensity for forming β-sheets of at least 5.

17. The structure of claim 11, wherein the β-sheet forming peptide sequence of each peptide amphiphile comprises VVEE (SEQ ID NO: 1), VEVE (SEQ ID NO: 2), or EVEV (SEQ ID NO: 3).

18. The structure of claim 11, wherein the PVDF consists of 3 to 10 VDF monomers.

19. The structure of claim 11, wherein the PVDF consists of three VDF monomers (VDF3), four VDF monomers (VDF4), five VDF monomers (VDF5), or six VDF monomers (VDF6).

20. The structure of claim 19, wherein each peptide amphiphile is independently selected from VDF6-EVEV (SEQ ID NO: 3), VDF6-VEVE (SEQ ID NO: 2), or VDF6-VVEE (SEQ ID NO: 1).

* * * * *